US012584920B2

(12) United States Patent (10) Patent No.: US 12,584,920 B2
Pantel et al. (45) Date of Patent: Mar. 24, 2026

(54) METHOD OF DETECTING CANCER OR CANCER CELLS

(71) Applicant: Panka Cancer Research AG, Grünwald (DE)

(72) Inventors: Klaus Pantel, Hamburg (DE); Kai Bartkowiak, Hamburg (DE)

(73) Assignee: Panka Cancer Research AG, Grünwald (DE)

( * ) Notice: Subject to any disclaimer, the term of this patent is extended or adjusted under 35 U.S.C. 154(b) by 61 days.

(21) Appl. No.: 16/486,913

(22) PCT Filed: Feb. 19, 2018

(86) PCT No.: PCT/EP2018/054052
§ 371 (c)(1),
(2) Date: Aug. 19, 2019

(87) PCT Pub. No.: WO2018/150031
PCT Pub. Date: Aug. 23, 2018

(65) Prior Publication Data
US 2020/0057067 A1 Feb. 20, 2020

(30) Foreign Application Priority Data
Feb. 20, 2017 (EP) .................................... 17157020

(51) Int. Cl.
*G01N 33/574* (2006.01)

(52) U.S. Cl.
CPC . *G01N 33/57415* (2013.01); *G01N 33/57484* (2013.01)

(58) Field of Classification Search
CPC .................. G01N 33/57415; G01N 33/57484
See application file for complete search history.

(56) References Cited

U.S. PATENT DOCUMENTS

| | | | | |
|---|---|---|---|---|
| 9,567,399 | B1 * | 2/2017 | Campbell | .......... C07K 16/2827 |
| 2004/0086504 | A1 * | 5/2004 | Sampath | ................ C07K 16/18 |
| | | | | 424/143.1 |
| 2011/0189700 | A1 | 8/2011 | Moses et al. | |
| 2016/0009805 | A1 * | 1/2016 | Kowanetz | ............... A61P 35/00 |
| | | | | 424/134.1 |
| 2018/0149653 | A1 * | 5/2018 | Walt | ................. G01N 33/57415 |

FOREIGN PATENT DOCUMENTS

| | | | | | |
|---|---|---|---|---|---|
| CN | 103940997 | A | * | 7/2014 | ......... G01N 33/5005 |
| EP | 3364190 | | | 8/2018 | |
| WO | WO-2012115885 | A1 | * | 8/2012 | .......... C12Q 1/6886 |
| WO | 2018150031 | | | 8/2018 | |

OTHER PUBLICATIONS

Luo et al, PD-L1-expressing neutrophils as a novel indicator to assess disease activity and severity of systemic lupus erythematosus, 2016, Arthritis Research & Therapy, 18:47, 11 pages (Year: 2016).*
Lin et al, Serum CYR61 is Associated With Clinical Disease Activity and Inflammation in Patients With Systemic Lupus Erythematosus, May 2015, Medicine, vol. 94, No. 19, 8 pages (Year: 2015).*
Terada et al, CYR61 is a potential prognostic marker for prostate cancer, 2012, Asian Journal of Andrology, 14, p. 405-408 (Year: 2012).*
ELISA Technical Guide and Protocols, 2010, Tech Tip#65, 14 pages (Year: 2010).*
R&D Systems, Inc., Quantikine ELISA Human CYR61/CCN1 Immunoassay, 2014, 16 pages (Year: 2014).*
Song et al, Serum CYR61 as a Potential Biomarker for Diagnosis of Colorectal Cancer, 2016, vol. 29, p. 519-524 (Year: 2016).*
Zhu et al, CYR61 participates in the pathogenesis of acute lymphoblastic leukemia by enhancing cellular survival via the AKT/NF-κB Signaling Pathway, 6:34018, 9 pages (Year: 2016).*
Etzioni et al, The Case for Early Detection, 2003, Nature Publishing Group, vol. 3, April, p. 1-10 (Year: 2003).*
Mercer, Use of Multiple Markers to Enhance Clinical Utility, 1990, p. 39-54 (Year: 1990).*
Tsai et al (CYR61 Promotes Breast tumorigenesis and Cancer Progression, Oncogene, 2002, 21, pp. 8178-8185) (Year: 2002).*
Chen et al (Function of CYR61 and CTGF in Cell Adhesive Signaling, Gene Expression, Wound Healing and Breast Cancer, Thesis, Univ. of Illinois, 2001). (Year: 2001).*
Huang et al (The matricellular protein CYR61 promotes breast cancer lung metastasis by facilitating tumor cell extravasation and suppressing anoikis, Oncotarget, 2017, vol. 8, (No. 6), pp. 9200-9215) (Year: 2017).*
International Search Report in corresponding PCT Application No. PCT/EP2018/054052, dated May 11, 2018.
Sánchez-Bailón, et al., "Cyr61 as mediator of Src signaling in triple negative breast cancer cells", Oncotarget, May 30, 2015, vol. 6, No. 15, pp. 13520-13538.
Song, et al., "Serum Cyr61 as a potential biomarker for diagnosis of colorectal cancer", Clin Transl Oncol (2017) 19: 519.
Zhao, et al., "Expression and prognostic significance of CEACAM6, ITGB1, and CYR61 in peripheral blood of patients with gastric cancer", J Surg Oncol., Oct. 2011;104(5):525-9.
Johnson, et al., "CYR61/CCN1 overexpression in the myeloma microenvironment is associated with superior survival and reduced bone disease", Blood, Sep. 25, 2014, vol. 124, issue 13, 2051-2060.
Aminololama-Shakeri, et al., "Can Radiologists Predict the Presence of Ductal Carcinoma In Situ and Invasive Breast Cancer?", AJR AM J, vol. 208, Apr. 2017, 933-939.
Mazel, et al. "Frequent expression of PD-L1 on circulating breast cancer cells", Mol Oncol., Jun. 9, 2015.

(Continued)

*Primary Examiner* — Samira J Jean-Louis
*Assistant Examiner* — Dennis J Sullivan
(74) *Attorney, Agent, or Firm* — Hovey Williams LLP; Crissa A. Cook

(57) ABSTRACT

The present invention provides methods of detecting breast cancer or breast cancer cells comprising: (a) obtaining a liquid sample from a subject which sample comprises cells, microvesicles and/or exosomes; and (b) determining the presence of soluble or cell surface associated Cyr61 in the sample; wherein the liquid sample is selected from blood, and/or bone marrow aspirate and wherein the determination of the presence of Cyr61 comprises detection via ELISA.

14 Claims, 33 Drawing Sheets

(56)                    References Cited

OTHER PUBLICATIONS

Barsoum, et al., "A Mechanism of Hypoxia-Mediated Escape from Adaptive Immunity in Cancer Cells", Cancer Res., 2014, vol. 74, 665-674.

Yachida, et al., "The Pathology and Genetics of Metastatic Pancreatic Cancer", Arch Pathol Lab Med, vol. 133, Mar. 2009, 413-422.

Rhim, et al., "EMT and Dissemination Precede Pancreatic Tumor Formation", Cell, Jan. 20, 2012, vol. 148, 349-361.

Effenberger, et al., "Detection and clinical relevance of early disseminated breast cancer cells depend on their cytokeratin expression pattern", Breast Cancer Res Treat, 2011, vol. 125 (3), 729-738.

Déry, et al., "Endoplasmic reticulum stress induces PRNP prion protein gene expression in breast cancer", Breast Cancer Research, 2013, vol. 15.

Braun, et al., "A Pooled Analysis of Bone Marrow Micrometastasis in Breast Cancer", N Engl J Med, vol. 353, issue 8, Aug. 25, 2005, 793-802.

Willipinski-Stapelfeldt, et al., "Changes in Cytoskeletal Protein Composition Indicative of an Epithelial-Mesenchymal Transition in Human Micrometastatic and Primary Breast Carcinoma Cells", Clin Cancer Res, Nov. 15, 2005, vol. 11, issue 22, 8006-8014.

Bartkowiak, et al., "Disseminated Tumor Cells Persist in the Bone Marrow of Breast Cancer Patients through Sustained Activation of the Unfolded Protein Response", Can Res, Dec. 14, 2015, vol. 75, issue 24, 5367-5378.

Vellon, et al., "aVb3 integrin regulates heregulin (HRG)-induced cell proliferation and survival in breast cancer", Oncogene, Mar. 14, 2005, vol. 24, 3759-3773.

Meng, et al., "Circulating Tumor Cells in Patients with Breast Cancer Dormancy", Clin Can Res, Dec. 15, 2004, vol. 10, 8152-8162.

Bidard, et al., "Clinical validity of circulating tumour cells in patients with metastatic breast cancer: a pooled analysis of individual patient data", Lancet Oncol, Apr. 2014, vol. 15, 406-414.

Bardelli, et al., "Liquid Biopsies, What We Do Not Know (Yet)", Cancer Cell, Feb. 13, 2017, vol. 31, 172-179.

Cohen, et al., "Detection and localization of surgically resectable cancers with a multi-analyte blood test", Science, Jan. 18, 2018 (10 pages).

Ledford, "Simple blood test detects eight different kinds of cancer", Nature, Jan. 18, 2018.

Bartkowiak, et al., "Discovery of a Novel Unfolded Protein Response Phenotype of Cancer Stem/Progenitor Cells from the Bone Marrow of Breast Cancer Patients", J Proteome Res, 2010, vol. 9, 3158-3168.

Pollari, et al., "Enhanced serine production by bone metastatic breast cancer cells stimulates osteoclastogenesis", Breast Cancer Res Treat, 2011, vol. 125, 421-430.

Peyruchaud, et al., "Early Detection of Bone Metastases in a Murine Model Using Fluorescent Human Breast Cancer Cells: Application to the Use of the Bisphosphonate Zoledronic Acid in the Treatment of Osteolytic Lesions", J Bone Min Res, Nov. 11, 2001, vol. 16, 2027-2034.

Dittmar, et al., "Induction of cancer cell migration by epidermal growth factor is initiated by specific phosphorylation of tyrosine 1248 of c-erbB-2 receptor via epidermal growth factor receptor", FASEB J, Sep. 19, 2002, vol. 16, ssue 13.

Lehtinen, et al., "15-Hydroxyprostaglandin dehydrogenase associates with poor prognosis in breast cancer, induces epithelial-mesenchymal transition, and promotes cell migration in cultured breast cancer cells", J Pathol, 2012, vol. 226, 674-686.

Bartkowiak, et al., "Two-Dimensional Differential Gel Electrophoresis of a Cell Line Derived from a Breast Cancer Micrometastasis Revealed a Stem/Progenitor Cell Protein Profile", J Proteome Res, Feb. 12, 2009, vol. 8, issue 4, 2004-2014.

Neuhoff, et al., "Improved staining of proteins in polyacrylamide gels including isoelectric focusing gels with clear background at nanogram sensitivity using Coomassie Brilliant Blue G-250 and R-250", Electrophoresis, 1988, vol. 9, 255-262.

Kohlbacher, et al., "TOPP—the OpenMS proteomics pipeline", Bioinformatics, 2006, vol. 23, e191-e197.

Sturm, et al., "OpenMS—An open-source software framework for mass spectrometry", BMC Bioinformatics, Mar. 26, 2008, vol. 9, 163-174.

Geer, et al., "Open Mass Spectrometry Search Algorithm", J Proteome Res, Feb. 23, 2004, vol. 3, 958-964.

Fenyo, et al., "A Method for Assessing the Statistical Significance of Mass Spectrometry-Based Protein Identifications Using General Scoring Schemes", Anal Chem, 2003, vol. 75, 768-774.

Nahnsen, et al., "Probabilistic Consensus Scoring Improves Tandem Mass Spectrometry Peptide Identification", J Proteome Res, 2011, vol. 10, 3332-3343.

Yuan, et al., "Cobalt Inhibits the Interaction between Hypoxia-inducible Factor-a and von Hippel-Lindau Protein by Direct Binding to Hypoxia-inducible Factor-a*", J Biol Chem, 2003, May 2, 2003, vol. 278, issue 18, 15911-15916.

Extended European Search Report in corresponding European Application Serial No. EP 17157020.3, dated Jun. 13, 2017.

Partial International Search Report in corresponding PCT Application No. PCT/EP2018/054052, dated Mar. 14, 2018.

Pantel, et al., "Dissecting the Metastatic Cascade", Nature, Jun. 2004, vol. 4, 448-456.

Pantel, et al., "Cancer micrometastases", Nat Rev Clin Oncol, 2009, vol. 6, 339-351.

Janni, et al., "Persistence of Disseminated Tumor Cells in the Bone Marrow of Breast Cancer Patients Predicts Increased Risk for Relapse—A European Pooled Analysis", Clin Cancer Res, Mar. 17, 2011, vol. 17, 2967-2976.

Yu, et al., "Circulating Breast Tumor Cells Exhibit Dynamic Changes in Epithelial and Mesenchymal Composition", Science, Feb. 1, 2013, vol. 339, 580-584.

Alix-Panabières, et al., "Challenges in circulating tumour cell research", Nat Rev, Sep. 2014, vol. 14, 623-631.

Sun, et al., "Involvement of Cyr61 in growth, migration, and metastasis of prostate cancer cells", British J Can, 2008, vol. 99, 1656-1667.

Lin, et al., "Elevated Expression of Cyr61 Enhances Peritoneal Dissemination of Gastric Cancer Cells through Integrin a2B1*", J Biolo Chem, Nov. 23, 2007, vol. 282, issue 47, 34594-34604.

Bendas, et al., "Cancer Cell Adhesion andMetastasis: Selectins, Integrins, and the Inhibitory Potential of Heparins", Inter J Cell Biol, Nov. 21, 2011, vol. 2012 (10 pages).

Pantel, et al., "Establishment of Micrometastatic Carcinoma Cell Lines: a Novel Source of Tumor Cell Vaccines", J Nat Can Inst, Aug. 2, 1995, vol. 87, issue 15, 1162-1168.

* cited by examiner

Table 1

| Swiss-Prot acc no. | recommended protein name by UniProtKB/Swiss-Prot (short name) | total number of peptides analyzed | number of different peptides analyzed | number of biological replicates | average value[a] | standard deviation | p-Value[c] |
|---|---|---|---|---|---|---|---|
| O00622 | Protein CYR61 / Cysteine-rich angiogenic inducer 61 (Cyr61) | 6 | 2 | 4 | 5.23[b] | 1.66 | $8.46 \times 10^{-7}$ |
| P02545 | Lamin-A/C | 112 | 20 | 4 | -1.05 | 0.21 | 0.003 |

Figure 2

Table 2

| Breast cancer | Cyr61 weak (score 0) | | Cyr61 moderate (score 1) | | Cyr61 strong (score 2) | | p-value[a] |
|---|---|---|---|---|---|---|---|
| | n | % | n Primary tumors | % | n | % | |
| All[b] | 83 | 56 | 29 | 20 | 35 | 24 | - |
| Histology | | | | | | | 0.242 |
| Infiltrating ductal | 67 | 79 | 23 | 79 | 23 | 62 | |
| Infiltrating lobular | 11 | 13 | 3 | 10 | 9 | 24 | |
| others | 7 | 8 | 3 | 10 | 5 | 14 | |
| DTC status (bone marrow) | | | | | | | 0.157 |
| positive | 19 | 23 | 9 | 31 | 14 | 40 | |
| negative | 64 | 77 | 20 | 69 | 21 | 60 | |
| Menopause status | | | | | | | 0.942 |
| post menopausal | 54 | 64 | 19 | 66 | 28 | 76 | |
| pre menopausal | 25 | 30 | 10 | 34 | 9 | 24 | |
| others | 5 | 6 | 0 | 0 | 0 | 0 | |
| Stage | | | | | | | 0.323 |
| $T_1$ | 40 | 48 | 18 | 62 | 24 | 65 | |
| $T_2$ | 34 | 40 | 10 | 34 | 13 | 35 | |
| $T_3$ | 3 | 4 | 0 | 0 | 0 | 0 | |
| $T_4$ | 7 | 8 | 1 | 3 | 0 | 0 | |
| Lymph node status | | | | | | | 0.035 |
| positive | 39 | 46 | 6 | 21 | 12 | 32 | |
| negative | 45 | 54 | 23 | 79 | 25 | 68 | |
| Grading | | | | | | | 0.002 |
| G1 | 3 | 60 | 34 | 57 | 45 | 74 | |
| G2 | 1 | 20 | 19 | 24 | 9 | 15 | |
| G3 | 1 | 20 | 27 | 34 | 7 | 11 | |
| Hormone-receptor status (ER + PR) | | | | | | | 0.123 |
| positive | 60 | 71 | 24 | 83 | 32 | 86 | |
| negative | 25 | 29 | 5 | 17 | 5 | 14 | |
| ErbB-2 status | | | | | | | 0.397 |
| positive | 1 | 1 | 1 | 4 | 2 | 6 | |
| negative | 72 | 99 | 25 | 96 | 33 | 94 | |
| Subtyping | | | | | | | 0.222 |
| ER + PR positive | 51 | 68 | 21 | 81 | 28 | 82 | |
| Triple negative | 21 | 28 | 4 | 15 | 5 | 15 | |
| ErbB2 positive | 3 | 4 | 1 | 4 | 1 | 3 | |

Figure 4

A
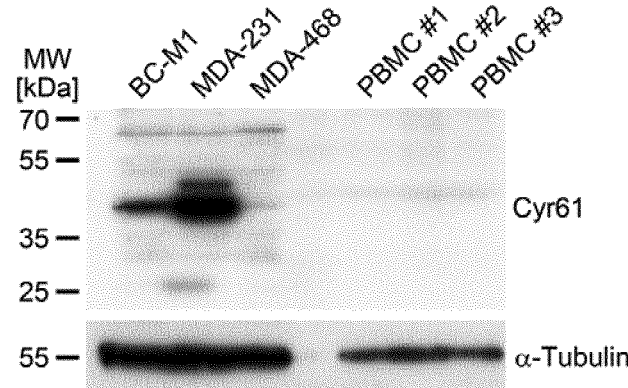
B
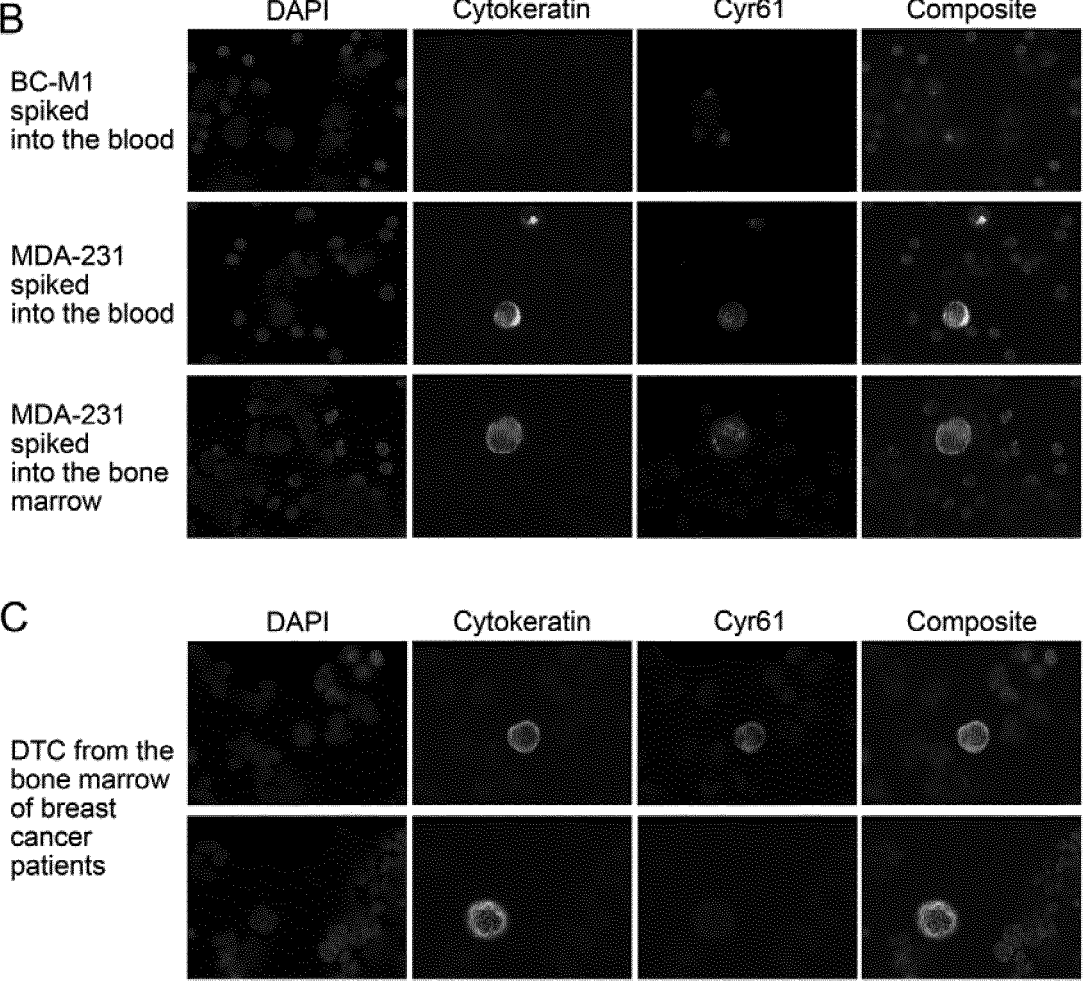
C
All experiments n = 3
Figure 29

Table 3    CTC and Cyr61 detection rates in blood samples from breast cancer patients.

| All patients | Analyzed samples | CTC positive (cytokeratin) | | Cyr61 positive CTC | | | |
|---|---|---|---|---|---|---|---|
| | n | n | % | n | % | n | % |
| | 33 | 33 | 100 | 8 | 24 | 3 | 9 |

| CTC positive patients | Cytokeratin positive CTC | Cytokeratin / Cyr61 positive CTC | Cytokeratin positive / Cyr61 negative CTC |
|---|---|---|---|
| Patient 1 | 11 | 9 | 2 |
| Patient 2 | 3 | 0 | 3 |
| Patient 3 | 8 | 1 | 7 |
| Patient 4 | 1 | 0 | 1 |
| Patient 5 | 39 | 7 | 32 |
| Patient 6 | 1 | 0 | 1 |
| Patient 7 | 5 | 0 | 5 |
| Patient 8 | 1 | 0 | 1 |
| Sum CTC (%) | 69 (100) | 17 (25) | 52 (75) |

Figure 32

METHOD OF DETECTING CANCER OR CANCER CELLS

RELATED APPLICATIONS

This application is the U.S. National Stage of International Patent Application No. PCT/EP2018/054052, filed Feb. 19, 2018, which is hereby incorporated by reference in its entirety, and which claims priority to European Patent Application No. 17157020.3, filed Feb. 20, 2017.

FIELD OF THE INVENTION

The present invention relates to methods detecting cancer cells, in particular the detection of circulating and/or disseminating cancer cells in liquid samples obtained from a subject suspected of having cancer.

TECHNICAL BACKGROUND

The metastatic cascade in cancer, such as in breast cancer, comprises the release of primary breast tumour cells into the blood (circulating tumour cells or CTC) followed by the settlement of such tumour cells at secondary organs (disseminated tumour cells or DTC) and their later metastatic outgrowth (1). In breast cancer, DTC frequently infiltrate the bone marrow (BM), survive chemotherapy and predict poor clinical outcome of the patients (2, 3).

However, numerous patients relapse despite negative BM findings at primary diagnosis in breast, lung and prostate cancer. Recently, similar findings were observed for CTCs in breast cancer. Such findings may point to technical limitations in current assays for the detection of CTCs and DTCs, which use antibodies against epithelial differentiation markers like cytokeratins.

Plasticity of tumour cells can lead to loss of epithelial characteristics and the acquisition of mesenchymal properties via intermediate phenotypes (EMT). Hence, due to a reduced expression of epithelial characteristics CTC and DTC with mesenchymal attributes (mCTC, mDTC) are not detected by the set of epithelial differentiation markers currently used. Recent experiments confirmed the presence of such mCTC in breast cancer patients (4).

The biology of mCTC and mDTC and their contribution to metastasis is not fully understood. One factor which promotes the acquisition of mesenchymal attributes and dissemination of tumour cells is hypoxia. Hypoxia is not restricted to the primary tumour, but can also occur in the human bone marrow, where values of only 1% $O_2$ (hypoxia) were detected in the areas of haematopoietic stem cell niches. In a prostate cancer mouse model, DTC have shown to occupy these niches which supports the idea that bone marrow DTC can be subjected to hypoxia. We previously detected microenvironmental stress tolerant mDTC in the bone marrow. Such DTC express epithelial differentiation markers at low level, but are strongly positive for proteins of the hypoxia response program unfolded protein response (UPR).

While CTC and DTC thus have some characteristics in common with the cancer from which they originate, epithelial characteristics of the original cancer are lost and at the same time mesenchymal properties are acquired in the course of CTC and DTC transformation (5). Cancer stem cells, which are the precursor cells of tumor cells with epithelial differentiation (carcinomas), may also lack epithelial characteristics and exhibit mesenchymal attributes. Hence, CTC/DTC may resemble properties of cancer stem cells. This applies in particular to the expression of cancer markers, i.e. sequences differentially expressed by cancer cells.

CYR61 is a signaling protein which is a member of the CCN family. The protein can be secreted or associated with the extracellular matrix (ECM). CYR61 is known to contribute to regulation of different of cellular activities by interaction with cell surface integrin receptors. Different Cyr61 activities have been associated with cancer. For example, (6) discloses methods of preventing or inhibiting breast cancer cell proliferation using compositions that interfere with or block sex steroid or growth factor binding to and inducing Cyr61 gene. The publication further mentions methods which screen for ligands regulating Cyr61 protein expression. Similarly, (7) discloses the detection of Cyr61 protein in urinary samples as a quick and easy screen for the diagnosis and prognosis of cancer in a patient.

While the expression of Cyr61 on cancer cells was observed and the role of the protein on cell growth, migration and metastasis of cancer cells has been reviewed in numerous scientific publications, including (8), (9) and (10), none of the prior art documents analyzed and compared the expression of Cyr61 on CTC and DTC to the expression of non cancerous cells in liquid samples. It was thus totally unclear whether this protein could be used as a marker in liquid samples.

Since mCTC and mDTC are difficult to detect with available marker proteins, there is a crucial need for additional and new markers that improve the detection and characterization of CTC and DTC in the human body.

SUMMARY OF THE INVENTION

The present invention provides methods of detecting cancer or cancer cells comprising:
- (a) obtaining a liquid sample from a subject which sample comprises cells, microvesicles and/or exosomes; and
- (b) determining the presence of soluble and/or cell surface associated Cyr61 in the sample;
- wherein the liquid sample is selected from blood, and/or bone marrow aspirate.

In a preferred embodiment the present invention provides methods of detecting cancer or cancer cells comprising:
- (a) obtaining a liquid sample from a subject which sample comprises cells, microvesicles and/or exosomes; and
- (b) determining the presence of soluble and/or cell surface associated Cyr61 in the sample;
- wherein the liquid sample is selected from blood and/or bone marrow aspirate and
- wherein the determination of the presence of Cyr61 comprises detection via ELISA.

The present inventors have surprisingly found that Cyr61 represents a highly advantageous marker for cancer and cancer cells and cell fragments in blood, plasma, serum and/or bone marrow aspirate, as the marker is expressed on cancer cells, but not on other cells present in these liquid samples.

The methods of detecting a pathologic condition according to the present invention are particularly suitable for the detection of circulating tumor cells and/or disseminating tumor cells.

In a particularly preferred embodiment the present invention provides methods of detecting breast cancer comprising:
- (a) obtaining a blood sample from a human subject and separating the cells from the plasma;

(b) determining the concentration of soluble Cyr61 in the plasma via a Sandwich ELISA, wherein the ELISA uses two different anti-human Cyr61 antibodies binding to distinct Cyr61 epitopes which are at least 50 amino acids apart;

(c) comparing the concentration of soluble Cyr61 in the test sample to the concentration of Cyr61 in a reference sample, wherein the reference sample is a plasma sample of healthy women over fifty years of age.

In these methods breast cancer or breast cancer cells are detected if the concentration of Cyr61 in the test sample is higher than in the reference sample.

In a further embodiment, the present invention provides methods for the diagnosis or differential diagnosis of cancer comprising a method of detecting cancer cells in a liquid sample as characterized above.

In a further alternative embodiment, the present invention provides methods for screening an anti-cancer drug, comprising:

(a) administering the drug to a subject;

(b) obtaining a liquid sample from the subject, wherein the liquid sample comprises cells;

(c) determining the presence and/or concentration of soluble or cell surface associated Cyr61 in the liquid sample;

(d) identifying the drug as an anti-cancer, if the concentration of Cyr61 in the sample is lower than the concentration of Cyr61 in a reference sample.

DETAILED DISCLOSURE OF THE INVENTION

The present invention provides methods of detecting cancer or cancer cells comprising:

(a) obtaining a liquid sample from a subject which sample comprises cells, microvesicles and/or exosomes; and (b) determining the presence of soluble and/or cell surface associated Cyr61 in the sample;

wherein the liquid sample is selected from blood and/or bone marrow aspirate and wherein the determination of the presence of Cyr61 comprises detection via ELISA.

The liquid sample is obtained from a subject, which is preferably a human, but can also be an animal.

In the context of the present application the terms cancer and tumor are used interchangeably. A cancer cell is a single tumor cell or part of a larger aggregate of tumor cells, i.e. a cell cluster in the context of CTCs or micrometastases in the context of DTC. Cancer cells are heterogeneous in nature and it is difficult to provide a definition that encompasses all cancer cells. In the context of the present invention a cancer cell is a cell that expresses epithelial cytokeratins and does not express the leukocyte marker CD45.

The method is most frequently carried out using a liquid sample obtained from a subject suspected of having cancer or a subject previously diagnosed with cancer. Accordingly, the methods of the present invention are preferably carried out using a liquid sample from a subject previously diagnosed with cancer using a method that differs from the methods of the present invention. As will be explained in more detail below, in this embodiment the methods of the present invention will provide a differential diagnosis of the cancer or inflammatory status.

Methods of obtaining a liquid sample from a subject, wherein the liquid sample is selected from blood, plasma, serum and/or bone marrow aspirate are well known in the art and any one of these methods can be used in carrying out the methods of the present invention. In the simplest form, the liquid sample obtained is a simple blood sample. Methods of obtaining a serum sample from a whole blood or plasma sample are well known in the art. Methods of obtaining a bone marrow aspirate are equally well known in the art. The methods of the present invention are in vitro methods for detecting cancer cells or for providing differential cancer diagnosis.

The methods of the present invention can be used for the detection of soluble and/or cell surface associated Cyr61. The term "soluble Cyr61" is used in the present application to refer to the protein and identifiable fragments thereof as present in the liquid fraction of the sample, such as in the serum of a blood sample. The term "cell surface associated Cyr61" is used in the present application to refer to the protein or an identifiable fragment thereof when present on the surface of cells, microvesicles and/or exosomes or as an integral part thereof.

In one embodiment the invention provides methods of detecting cancer or cancer cells comprising:

(a) obtaining a liquid sample from a subject which sample comprises cells, microvesicles and/or exosomes; and (b) determining the presence of soluble Cyr61 in the sample;

wherein the liquid sample is selected from blood, and/or bone marrow aspirate.

Similarly, the invention provides methods of detecting cancer or cancer cells comprising:

(a) obtaining a liquid sample from a subject which sample comprises cells, microvesicles and/or exosomes; and (b) determining the presence of cell surface associated Cyr61 in the sample;

wherein the liquid sample is selected from blood, and/or bone marrow aspirate.

Alternatively, the invention thus provides methods of detecting cancer or cancer cells comprising:

(a) obtaining a liquid sample from a subject which sample comprises cells, microvesicles and/or exosomes; and (b) determining the presence of soluble and cell surface associated Cyr61 in the sample;

wherein the liquid sample is selected from blood, and/or bone marrow aspirate.

In one aspect the present invention provides methods, methods of detecting cancer, wherein the sample is a blood sample, the serum is isolated and Cyr61 is detected in the serum. The detection may comprise immunocytochemical analysis. In the preferred embodiment the detection comprises detecting Cyr61 in serum with an ELISA.

The methods of the present invention are also particularly advantageous for the detection of CTC and/or or DTC. CTC are tumor cells that expresses epithelial cytokeratins and which do not express the leukocyte marker CD45 which were released from a cancerous origin and are thus present in body liquids. The present inventors surprisingly found that CTC can be detected and characterized by the expression of Cyr61. The detection methods comprise contacting the cells, microvesicles and/or exosomes or the homogenate thereof with at least one further antibody selected from an anti-cytokeratin antibody and an anti-CD45 antibody.

DTC are tumor cells or cells that expresses epithelial cytokeratins and which do not express the leukocyte marker CD45 and which are present outside from a cancerous origin in the body and are present in secondary sites such as bone marrow, liver, lungs, or brain. Secondary sites can be any site in the human body that is not the place of the cancerous origin or sites that were defined as sources for CTCs. DTC are thus cancer cells expressing Cyr61 which are obtained from a site in the human body that is not the place of the cancerous origin.

In a particularly preferred embodiment, the method of detecting breast cancer or breast cancer cells of the present invention use a sandwich ELISA using two different anti-human Cyr61 antibodies binding to distinct Cyr61 epitopes. In this embodiment, the sample is preferably blood, serum is isolated and Cyr61 is detected in the serum using a sandwich ELISA using two different anti-human Cyr61 antibodies binding distinct Cyr61 epitopes. In one aspect the the distinct Cyr61 epitopes bound by the different anti-human Cyr61 antibodies are at least 50 amino acids apart, or at least 75, 85 or 100 amino acids apart. This means that each of the Cyr61 epitopes bound by the anti-human Cyr61 antibodies is separated from the other Cyr61 epitope by at least 75 amino acids.

In a further preferred embodiment the method of detecting breast cancer or breast cancer cells in a subject according to the present invention comprises the determination of the concentration of Cyr61 in the test sample. In one aspect this method further comprises a step of comparing the concentration of Cyr61 in the test sample to the concentration of Cyr61 in a reference sample.

The present inventors have shown that respective methods are particularly advantageous if the method of detecting breast cancer or breast cancer cells in a subject use a reference sample selected from:

(i) a plasma sample of healthy women over fifty years of age; and (ii) an age- and sex-matched reference sample.

The concentration of Cyr61 in the reference sample can be obtained by determining the concentration of Cyr61 in a single reference sample, for example in a single sample of a healthy woman over fifty years of age. Alternatively, the concentration of Cyr61 in the reference sample can be determined as the average or mean value of the concentration of Cyr61 in several reference samples, for example as the average value of the concentration of Cyr61 in several reference samples of healthy women over fifty years of age.

In general the methods of detecting breast cancer as described above detect breast cancer or breast cancer cells if the concentration of Cyr61 in the test sample is higher than in the reference sample.

The step of detecting a pathologic condition may comprise a step, wherein the cells, microvesicles and/or exosomes present in the liquid sample are homogenized, and Cyr61 is detected in the homogenate. Cells in a sample are homogenized by breaking the cell membranes and releasing the cell organelles and the cytoplasm. Numerous methods for homogenization of cells are known in the art and can be used in the context of the present invention to detect Cyr61 located in the cells. In an alternative approach, cell surface associated Cyr61 is detected and this approach obviously does not require cell homogenization. In both methods, the cells, microvesicles and/or exosomes may be separated from the liquid sample before determining the presence of Cyr61. This can be done for example by centrifugation. The separation process may also encompass methods of concentrating the cells or cell fragments either in relation to the liquid sample as such or in relation to other cells not expressing Cyr61.

The detection of the presence of Cyr61 may comprise the detection of the presence or the determination of the concentration of Cyr61. Numerous different methods for detecting the presence or determining the concentration of Cyr61 are known in the art and any analytical approach that is suitable to detect Cyr61 in a liquid sample on nucleic acid (cyr61) or protein level can be used in the context of the present invention.

In preferred methods of the present invention the concentration of Cyr61 is determined using an antibody or antibody derivatives to detect Cyr61 levels. Accordingly, the methods of detecting cancer cells of the present invention may be characterized by a step, wherein the detection comprises contacting the cells, microvesicles and/or exosomes or the homogenate thereof with an anti-Cyr61 antibody. Anti-Cyr61 antibodies are known in the art and can be used for the purposes of the present invention. For example, the methods may comprise antibody based immunocytochemical analysis methods well known in the art.

In a particularly preferred embodiment, methods of detecting cancer or cancer cells of the present invention further comprise a step, wherein the cells, microvesicles and/or exosomes or the homogenate thereof are contacted with an anti-Cyr61 antibody and with at least one further antibody selected from an anti-cytokeratin antibody and an anti-CD45 antibody. Numerous anti-cytokeratin and anti-CD45 antibodies are known in the art and can be used for the purposes of the present invention. As indicated above, CTC are tumor cells that express epithelial cytokeratins but do not express the leukocyte marker CD45. The method using several antibodies thus provides a more complete characterization of the cell types analyzed as part of the detection process.

In one aspect the method of detecting cancer or cancer cells comprises:

(a) contacting the cells, microvesicles and/or exosomes or the homogenate thereof with at least a first set of antibodies comprising an anti-Cyr61 antibody and an anti-cytokeratin antibody and/or an anti-CD45 antibody;

(b) contacting the sample with a second set of antibodies with specificity for each of the antibodies of the first set of antibodies;

(c) detecting a signal emitted by binding of the second antibody.

In a related aspect the method of detecting cancer or cancer cells comprises:

(a) contacting the cells, microvesicles and/or exosomes or the homogenate thereof with at least a first set of antibodies comprising an anti-Cyr61 antibody and an anti-cytokeratin antibody and/or an anti-CD45 antibody;

(b) removing unbound antibody by washing;

(c) contacting the sample with a second set of antibodies with specificity for each of the antibodies of the first set of antibodies;

(d) removing unbound antibody by washing; and (e) detecting a signal emitted by binding of the second antibody.

The signal emitted by the binding of the second antibody may be a fluorescent signal and may be detected by automated detection devices.

The antibody may bind the entire protein or a part or fragment of Cyr61. Further methods of detection can be also used and include FACS, ELISA, Western-Blot, enzymatic assays, PCR, hybridization and array technologies. Further included are methods based on biochemical or biophysical detection or analysis, including microscopic analysis, such as entire wavelength range analysis, chromatographic or electrophoretic methods, labeling/derivatization techniques, for example using isotopes or chemical compounds, gas chromatography, atomic force microscopy, mass spectrometry, for example coupled with or without chromatography and other spectrometric methods, nuclear magnetic resonance spectroscopy and other spectrometric methods. Further, different parts of these methods have been combined in the prior art, including capture of Cyr61 by immunoprecipitation, followed by mass spectrometric analysis or chromatography coupled with mass spectrometry. Insofar as the detection of the presence or concentration of Cyr61 is based on the detection of a nucleic acid, the detection of RNA, in particular mRNA, is preferred.

The methods of detecting cancer cells according to the present invention may comprise a comparison of the value obtained with an internal or external standard. Depending on the assay format oligonucleotides (DNA or RNA), proteins or peptides having the sequence of Cyr61 can be used in a known concentration as the standard.

The methods of detecting a pathologic condition according to the present invention may also comprise a step, wherein the concentration of Cyr61 in the sample is compared to the concentration of Cyr61 in a reference sample. The concentration of Cyr61 in a reference sample may but need not be detected in the same assay as the concentration of Cyr61 in the sample to be tested. In fact, the concentration of Cyr61 in the reference sample may have been obtained as a standard long before determining the concentration in the sample to be tested and the comparison of the concentration in the sample to be tested and the concentration in the reference sample may be carried out automatically by a device analyzing the concentration of Cyr61 in the sample to be tested.

The methods of detecting cancer cells according to the present invention are particularly suitable for the diagnosis of cancer. Accordingly, the present invention provides a method for the diagnosis of cancer, which comprises a method of detecting cancer cells as described above.

Any diagnosis form of cancer can be used in the methods of the present invention. However, preferably the methods of the present invention are used for the differential diagnosis of cancer, such as for the identification of circulating tumor cells and/or disseminating tumor cells.

The methods for the diagnosis or differential diagnosis of cancer according to the present invention may comprise the detection of further cancer markers, for example including the detection of HIF-1 and/or PD-L1. The present application for the first time shows that in certain cancer types Cyr61 expression in cancer cells present in liquid samples is closely related to the expression of HIF-1 and/or PD-L1. Numerous different alternatives for detecting the expression of HIF-1 and/or PD-L1 are known in the art and can be used in the methods of the present invention for detecting of HIF-1 and/or PD-L1. The detection of Cyr61, of HIF-1 and/or PD-L1 can be carried out in a single assay or in completely unrelated assays.

In certain embodiments, the diagnosis of cancer as provided by the present invention represents the diagnosis of a cancer cell which is an epithelial cancer cell or a mesenchymal cancer cell type.

The methods for the diagnosis of cancer are particularly suitable for the differential diagnosis of the metastatic potential of a breast cancer cell, a prostate cancer cell, a lung cancer cell, etc.

In this manner, the present invention may be used to identify the treatment regimen for a patient who has been diagnosed with cancer, including patients who have been diagnosed with cancer and from which the primary tumor has been removed by surgical procedures.

In alternative embodiments, the methods of detecting cancer cells according to the present invention are directed to the diagnosis of an early cancer inflammatory condition. It is well known that certain inflammatory conditions induce adverse microenvironmental conditions, like hypoxia, which allow the detection of early malignant cells, for example in conditions such as pancreatitis or colitis ulcerosa.

In a further related embodiment, the present invention provides methods for screening an anti-cancer drug, comprising:
- (a) administering the drug to a subject;
- (b) obtaining a liquid sample from the subject, wherein the liquid sample comprises cells;
- (c) determining the presence and/or concentration of Cyr61 in a liquid sample of the subject;
- (d) identifying the drug as an anti-cancer, if the concentration of Cyr61 in the sample is lower than the concentration of Cyr61 in a reference sample.

BRIEF DESCRIPTION OF THE FIGURES

FIG. 2:
Table 1: Identification of the differential expression of Cysteine-rich angiogenic inducer 61 (Cyr61) by SILAC and LC-MS/MS. The protein expression profile of MDA-MB-468 and BC-M1 was compared in 4 biological replicates. The expression value of Lamin-A/C is shown as a reference for a not differentially expressed protein.
[a]A positive value of the average signal ratio signifies an increased protein expression in BC-M1 and a negative value signifies an increased protein expression in MDA-468.
[b]Quantification was performed manually. [c]Student's t-test, with $p<0.05$ was considered significant.

Figure 1:
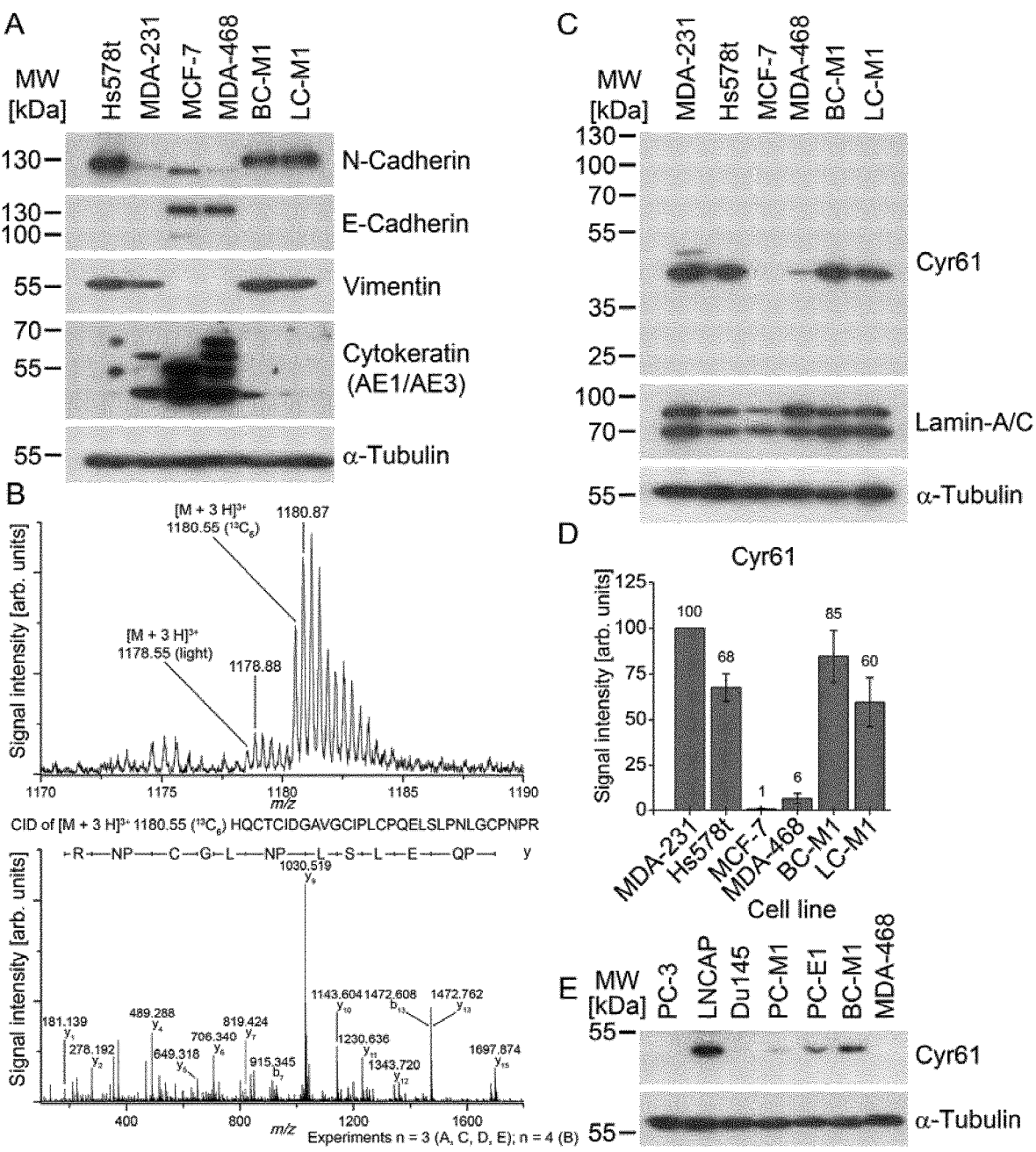
FIG. 1
A: Comparison of the epithelial differentiation grade of the disseminated tumor cell lines BC-M1 (breast cancer) and LC-M1 (lung cancer) with breast cancer cell lines by western blot analysis. The cells were cultivated under standard conditions.
B: Quantification and identification of cysteine-rich angiogenic inducer 61 (Cyr61) by SILAC LC-MS/MS analysis. Upper image: Relevant mass range of the $MS_1$-spectrum. Lower image: Positive ion mode LC-ESI-QTOF-CID spectrum of m/z 1180.55.
C: Analysis of the Cyr61 expression in cancer cells by Western Blot. Lamin-A/C is shown as an example for a not differentially expressed protein between MDA-MB-468 (MDA-468) and BC-M1.
D: Quantitative analysis of the Cyr61 expression. The signals were normalized to the loading control alpha Tubulin. The average values of three independent experiments are given as numbers, and standard deviation is indicated by vertical error bars. E: Western Blot analysis in prostate cancer cell lines for Cyr61. PC-E1 and PC-M1 are prostate cancer DTC cell lines.

B: Immunohistochemical Cyr61 detection in bone marrow metastases of breast cancer patients. Nuclei were stained by hemalum. Scale bars: A: 100 µm; B: 67 µm.

FIG. 4:

Table 2: Association of Cyr61 expression and clinicopathological properties on a breast cancer tissue microarray and on human primary lung cancer samples.

[a]Pearson chi-square or Fisher's exact test.

[b]In total, Cyr61 staining results were obtained for 147 primary breast tumors.

Since not for all of these cases all clinicopathological data were available, the number of cases may be lower than 147 for the individual parameter.

FIG. 5:

Analysis of Cysteine-rich angiogenic inducer 61 (Cyr61) levels in a model system for tumour cell dissemination to the bone marrow; analyses by Western Blot.

A: Starting conditions after culturing of the cell lines under standard cell culture conditions.

B: Simulation of a settlement of DTC to a hypoxic (1% of $O_2$) microenvironment as found in the bone marrow. For MCF-7 the positive control (+) was MDA-MB-231 (MDA-231)

C: Quantitative Western Blot analysis for Cyr61 for the conditions specified in FIG. 2B.

D: Effect of the stabilization of hypoxia-inducible factor 1-alpha (HIF-1α) to Cyr61.

E: Cyr61 levels in the bone metastatic sublines (MDA-231 SA and MDA-231 B02) and the brain metastatic subline (MDA-231 BR) of MDA-231.

F: Impact of glucose starvation to Cyr61 levels. Grp78 (78 kDa glucose-regulated protein) served as a positive control. Since a large amount of MDA-231 cells detached from the cell culture flask after 50 h of glucose withdrawal, these cells were analyzed separately.

G: Induction of Cyr61 and Vimentin under exceptionally adverse conditions (hypoxia and glucose starvation).

Vertical error bars display the standard deviation. S: standard culture conditions.

FIG. 6:

Western Blot analysis for Cysteine-rich angiogenic inducer 61 (Cyr61) and PD-L1 (programmed cell death 1 ligand 1) in cancer entities that predominantly disseminate via the blood or lymphatic vessels (A) or with a prominent proportion of peritoneal dissemination (B). The cell lines were cultured under standard conditions, and alpha-tubulin served as a loading control. BC-M1 and MDA-MB-468 (MDA-468) were analyzed for comparison with other experiments.

A: Analyzed cancer entities: Prostate cancer (LNCAP, Du145, PC-3), breast cancer (BT20, BT474, ZR-75-1), head and neck cancer (Ca127, SCC 25).

B: Analyzed cancer entity: Pancreatic cancer (Panc1, Panc2, BxPC3, 5061).

FIG. 7:

Response of Cysteine-rich angiogenic inducer 61 (Cyr61) to ErbB-2 under standard cell culture conditions (S) and hypoxic conditions (1% of $O_2$). MDA-MB-468 (MDA-468) was transfected with an ErbB-2 expression vector (MDA-468 ErbB-2). MDA-468 PM expresses an ErbB-2 protein in which the tyrosine at position 1248 was replaced by phenylalanine. MDA-468 control was transfected with an expression vector without insert.

A: Western Blot analysis for denoted proteins and conditions.

B: Quantitative analysis of the Cyr61 and Vimentin levels under hypoxia.

C: Microscopic images of MDA-468 cells that were stained for vimentin and nuclei (DAPI) after cultivation under standard cell culture condition (S) and 90 h of 1% $O_2$. Composite images of the Vimentin and DAPI signals are shown. Vimentin positive cells are labelled with arrows.

D: Proportion of Vimentin positive cells in the MDA-468 cell lines in percent.

E: Western Blot analysis for the breast cancer cell line BT20 and three squamous cell carcinoma cell lines.

F: Cyr61 induction after cell stimulation with the epidermal growth factor EGF. The stimulation was performed under standard conditions.

FIG. 8:

Detection of Cysteine-rich angiogenic inducer 61 (Cyr61) secretion in MDA-MB-231 (A) and BC-M1 (B). Cells were treated with Brefeldin A to block the protein secretion. The supernatant of the cell culture medium contains the secreted protein fraction, whereas the pellet contains detached cells. The western blot images show the analysis for Cyr61 and 78 kDa glucose-regulated protein (Grp78; positive control). Alpha-Tubulin was analyzed to detect potential cytoplasmic protein contamination in the supernatant. The graph on the right shows a balance sheet for the protein amounts from the cell culture flasks. The average values of three independents experiments are shown and are given as numbers. Standard deviation is denoted by vertical error bars. Since the total protein amount for two of the three replicates of the MDA-231 detached cells (untreated) was below 50 µg, a Western Blot lacking this sample is shown. (C) Analysis of the denoted cell lines for integrin family members by Western Blot. The most prominent Cyr61 receptor from the integrin family is the heterodimer of integrin αv and integrin β3, which are both present in the DTC cell lines at high levels. The cells were cultured under standard conditions.

FIG. 9:

Isolation of Cyr61 by immunoprecipitation using the rabbit anti-Cyr61 antibody (H78) for the Cyr61 isolation and a mouse monoclonal antibody for Cyr61 detection in the Western Blot. Whole cell lysates from BC-M1 and MDA-MB-231 served as positive controls for the respective immunoprecipitation. The Cyr61 immunoprecipitation from BC-M1 is designated as BC-M1 Cyr61 and for MDA-MB-231 it is designated as MDA-MB-231 Cyr61. Assays using IgG instead of the anti-Cyr61 antibody (H78) served as controls for the specificity of the immunoprecipitation. As a negative control, SDS sample buffer was analyzed. The experiments were performed in biological triplicates.

FIG. 10:

A: Western Blot analyses of the anti-Cyr61 antibody from Santa Cruz (H78) and of the antibody from Cell Signaling (CST). For both antibodies the same cell lysates were applied. For the analysis of the CST antibody, 40 µg of protein was applied to each lane, and the primary antibody was diluted 1:500. For the analysis of the H78 antibody 20 µg of protein was applied to each lane, and the primary antibody was diluted 1:1,000. The quantitative analyses were performed by densitometric analysis of the X-ray films. The average values are given as numbers and the error bars denote the standard deviation. B: Western Blot analyses for the assessment of the anti-Cyr61 antibody (H78) at a dilution of 1:10,000

(left) and 1:1,000 (right). Applied were a dilution series of human recombinant Cyr61 and whole cell lysates of the specified cell lines. For the visualization of unspecific detection of the anti-Cyr61 antibody, 40 µg of MCF-7 cell lysate was applied. These protein samples were analyzed with varying anti-Cyr61 antibody dilutions as well as with varying exposition times of the X-ray films. For MDA-MB-468 (MDA-468), MDA-MB-231 (MDA-231) and BC-M1 10 µg of cell lysate were applied.

Figure 10:
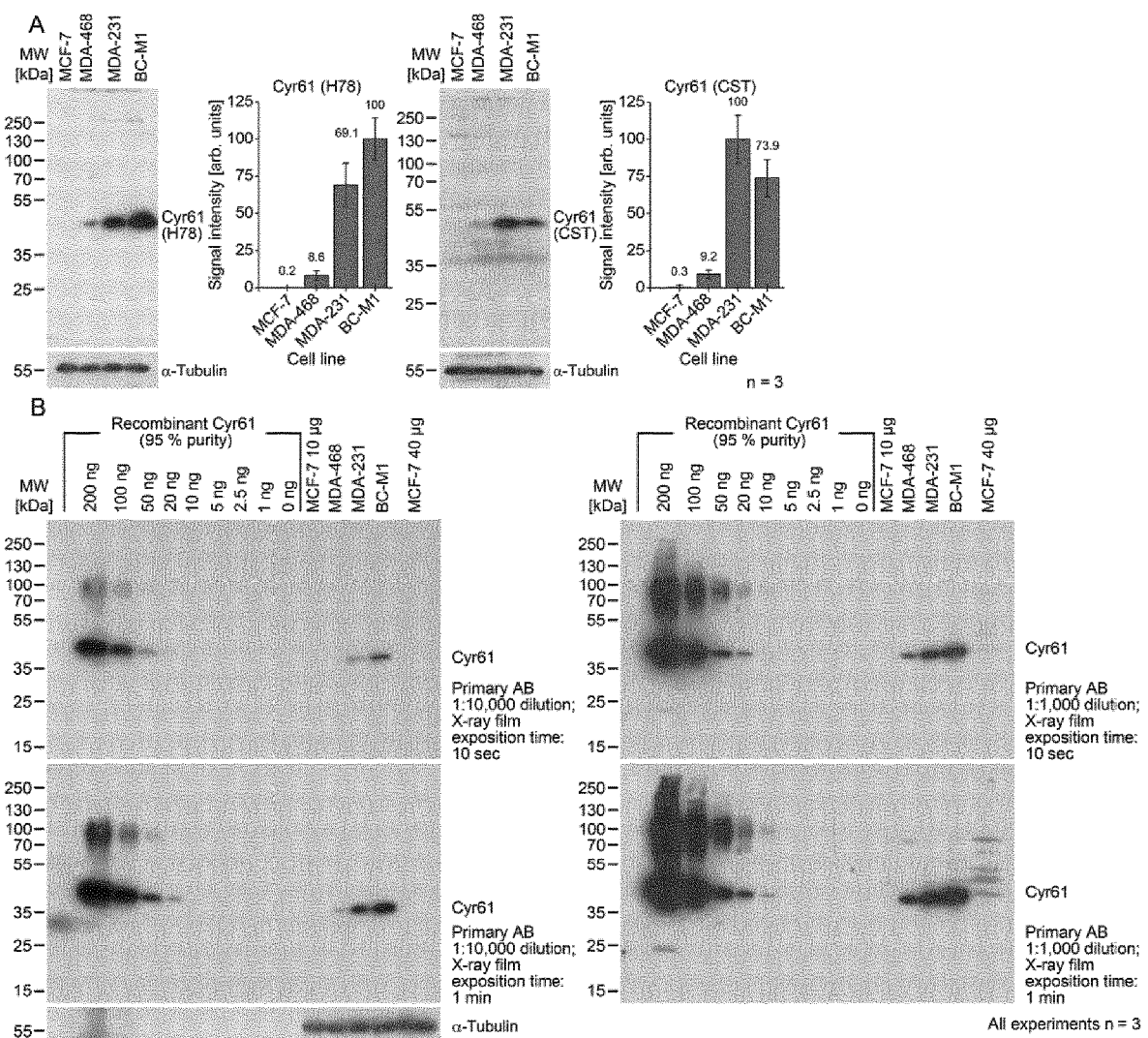

FIG. 11:

Calibration curves for the calculation of linear equations. A. The values were determined on the quantitative analyses of the Western Blots as shown in FIG. 10B. The x-axis shows the values of the signal intensities for recombinant Cyr61 and the y-axis shows the protein amount of recombinant Cyr61 protein. Each point of measurement is the average value of three experiments and the standard deviation of the x-values is presented as horizontal error bars. The inlay displays the parameters of the equation, which was calculated as y=2.5678x, with y as the protein amount of Cyr61 [µg] and x as the signal intensity on the X-ray films [arb. units]. B, C, D: Calibration curves comprising the x-axis with the values of the signal intensities for recombinant Cyr61 and the y-axis with the protein amount of recombinant Cyr61 protein applied. Each point of measurement is the average value of three ELISA experiments and the standard deviation of the x-values is presented as horizontal error bars. The inlays displays the parameters of the equation, consisting of y as the protein amount of Cyr61 [µg], x as the signal intensity (OD405 nm) in the ELISA reader and the fixed value as the intercept. B: Calibration curve for the analyses of MCF-7. C: Calibration curve for the analyses the cell culture supernatants. D: Calibration curve for the analysis of the cell lysates and cell culture supernatants of MCF-7, MDA-MB-468, MDA-MB-231 and BC-M1.

FIG. 12:

A: Determination of the Cyr61 values in the cell culture supernatant of breast cancer cell lines by ELISA. The cells were cultured under standard culture conditions. For the time point t=0 h fresh medium was added to the cells followed by determination of the Cyr61 concentration for each measurement point. From the determined Cyr61 concentration (and known medium volume) and the cell number the Cyr61 number per cell was calculated. B: Determination of Cyr61 secretion rates in BC-M1 and MDA-MB-231. Other than the experiments in FIG. 12A, the cell culture medium was replaced every 12 h. The values show the average values of three independent experiments. The standard deviation is represented by vertical error bars. C: Western Blot analysis of plasma samples from healthy donors for Cyr61. From each donor 100 µl of blood plasma was applied. Since a protein purification step was applied to the samples, the recovery of Cyr61 was analyzed by spiking of 100 ng of recombinant Cyr61 to 100 µl of plasma from donor #1. Cell lysate of BC-M1 (without purification step) served as a further control. To identify potential unspecific bands with weak signal intensity, the X-ray film was exposed to 15 minutes.

FIG. 13:

Western Blot analyses of the anti-Cyr61 antibodies from Santa Cruz H78 (left) and H2 (right). For both antibodies the same cell lysates were applied. For the analysis of the H78 and the H2 antibodies 20 µg of protein was applied to each lane, and the primary antibody was diluted 1:1.000. Alpha-Tubulin served as a loading control.

FIG. 14:

Isolation of Cyr61 by immunoprecipitation using the mouse anti-Cyr61 antibody (H2). For the detection of Cyr61 by Western Blot the rabbit anti-Cyr61 antibody (H78) was used. Cell culture supernatant from MDA-MB-231 was applied for the immunoprecipitation (MDA-MB-231 Cyr61). Application of IgG instead of the anti-Cyr61 antibody (H2) served as a control for the specificity of the immunoprecipitation (MDA-MB-231 IgG). Recombinant Cyr61 served as a reference for the estimation of the isolated Cyr61 amount. As a negative control, SDS sample buffer was analyzed. Cell lysate MDA-MB-231 served as an additional control for the specificity of the immunoprecipitation.

FIG. 15:

Western Blot analyses for the assessment of the anti-Cyr61 antibodies H78 (left) and H2 (right). The primary antibodies were applied at a dilution of 1:10,000. Applied were a dilution series of human recombinant and purified Cyr61 and whole cell lysates of the specified cell lines. For the visualization of potential unspecific detection of the anti-Cyr61 antibodies, 40 µg of MCF-7 cell lysate was additionally analyzed. MDA-MB-231 (MDA-231).

FIG. 16:

Calibration curve for the calculation of a linear equation. The calibration curve was used for the analyses shown in FIG. 17. The x-axis shows the values of the signal intensities for recombinant Cyr61 and the y-axis shows the protein amount of recombinant Cyr61 protein applied. The inlay displays the parameters of the equation, which was calculated as y=0.4118x+0.0009 with y as the protein amount of Cyr61 [ng], x as the signal intensity in the ELISA reader at 450 nm and the fixed value of 0.000928 as the intercept.

FIG. 17:

Determination of the Cyr61 amounts 5 µg whole cell lysate (A) and 0.5 µl cell culture supernatant (B) by ELISA. Tested were pure samples of the cell lysates and supernatants (light grey) as well as samples of cell lysates and culture supernatants in which 500 pg of recombinant Cyr61 was spiked (dark grey). The numbers display the average values of three experiments. The standard deviation is displayed by vertical error bars. The cells were cultured under standard culture conditions, and the cell culture supernatant was harvested after 72 h.

FIG. 18:

Calibration curve for the calculation of a linear equation. The calibration curve was used for the analyses shown in FIG. 19. The x-axis shows the values of the signal intensities for recombinant Cyr61 and the y-axis shows the protein amount of recombinant Cyr61 protein applied. The inlay displays the parameters of the equation, which was calculated as y=0.40636x+0.00498 with y as the protein amount of Cyr61 [ng], x as the signal intensity in the ELISA reader at 450 nm and the fixed value of 0.00498 as the intercept.

FIG. 19:

Determination of the Cyr61 amounts in samples of MCF-7 by ELISA. A: Analyses of cell lysates. Tested were samples of pure cell lysates (light grey) and 10 µg of cell lysates in which recombinant human Cyr61 were spiked (dark grey). B: Analyses of cell culture supernatants. Tested were samples of pure cell culture supernatants (light grey) and 20 μl of cell culture supernatants in which recombinant human Cyr61 were spiked (dark grey). The numbers display average values of three experiments. The standard deviation is displayed by vertical error bars. The cells were cultured under standard culture conditions, and the cell culture supernatant was harvested after 72 h.

FIG. 20:

Calibration curve for the calculation of a linear equation. The calibration curve was used for the analyses shown in FIG. 21. The x-axis shows the values of the signal intensities for recombinant Cyr61 and the y-axis shows the protein amount of recombinant Cyr61 protein applied. The inlay displays the parameters of the equation, which was calculated as y=0.40669x+0.00279 with y as the protein amount of Cyr61 [ng], x as the signal intensity in the ELISA reader at 450 nm and the fixed value of 0.00279 as the intercept.

FIG. 21:

Determination of the Cyr61 amounts in samples of MDA-MB-231 (MDA-231) by ELISA. A: Analyses of cell lysates. Tested were samples of pure cell lysates (light grey) and 1 μg of cell lysates in which recombinant human Cyr61 were spiked (dark grey). B: Analyses of cell culture supernatants. Tested were samples of pure cell culture supernatants (light grey) and 75 nl of cell culture supernatants in which recombinant human Cyr61 were spiked (dark grey). The numbers display average values of three experiments. The standard deviation is displayed by vertical error bars. The cells were cultured under standard culture conditions, and the cell culture supernatant was harvested after 72 h.

FIG. 22:

Western Blot analysis of plasma samples from healthy donors for Cyr61 using the anti-Cyr61 antibody H78. From each donor 100 μl of blood plasma was applied. Since a protein purification step was applied to the samples, the recovery of Cyr61 was analyzed by spiking of 100 ng of recombinant Cyr61 to 100 μl of plasma from donor #1. Cell lysate of BC-M1 (without purification step) served as a further control. To identify potential unspecific bands with weak signal intensity, the X-ray film was exposed to 15 minutes.

FIG. 23:

Calibration curve for the calculation of a linear equation. The calibration curve was used for the analyses shown in FIG. 24. The x-axis shows the values of the signal intensities for recombinant Cyr61 and the y-axis shows the protein amount of recombinant Cyr61 protein applied. The inlay displays the parameters of the equation, which was calculated as y=0.40982x+0.00283 with y as the protein amount of Cyr61 [ng], x as the signal intensity in the ELISA reader at 450 nm and the fixed value of 0.00283 as the intercept.

FIG. 24:

Application of the Cyr61 ELISA to plasma samples of healthy individuals over an age of 50 years. Each data point displays the average value of plasma samples from four individuals that were analyzed in triplicates. The average value is shown as numbers and the standard deviation as vertical error bars. The curve displays a non-linear fit (allometric) of the values. The corresponding equation had the form $y=2.341 \times x^{-1.050}$.

FIG. 25:

Determination of the detection limit of the Cyr61 ELISA in plasma samples of healthy female control individuals over the age of 50 years. Recombinant human Cyr61 was spiked into 2.5 μl of plasma volume followed by application of the ELISA. For the assessment of the detection limit, three samples of pure plasma were compared with plasma containing spiked Cyr61 using Student's two-tailed t-test for each data point. The p-value of each t-test is presented as numbers. The p-value of 0.05 is indicated as a horizontal line.

FIG. 26:

Stability testing of Cyr61 in the plasma of breast cancer patients. All plasma samples were stored a −80° C. after acquisition. A: plasma samples of breast cancer patients with no visible signs of overt metastases. The samples were taken in the years 1998 and 1999. B: Plasma samples of metastatic breast cancer patients. The samples were taken in October 2016 and analyzed immediately after purchase. All samples were repeatedly analyzed for Cyr61 by ELISA in October 2016, April 2017 and August 2017. Each sample was analyzed in triplicates on each time point. The presented values are the average value and the standard deviation is given as vertical error bars. The slight increase in the Cyr61 values over time might be due to advances in sample handling.

FIG. 27:

Determination of the Cyr61 levels in 100 μl of blood plasma from healthy control persons and breast cancer patients by ELISA. A: Cyr61 values in a set of indiscriminately chosen healthy donors. Five micrograms of cell lysate from MDA-MB-231 (MDA-231) was used as a positive control. B: Cyr61 values in a set of female healthy persons with an age of more than 50 years at the time of sample acquisition. C: Cyr61 concentration in samples from metastatic breast cancer patients (light grey) and from patients with no signs of overt metastasis at the time of the diagnosis of the primary tumour (black). As a comparison, the average values of the Cyr61 concentrations shown in A (healthy, dark grey) and B (female 50+, white bar) are shown. One hundred 100 μl of cell culture medium was analyzed for an estimation of an unspecific background. The numbers indicate the average values of three measurements, and standard deviation is indicated by vertical error bars.

FIG. 28:

Analysis of cell culture supernatants by the Cyr61 sandwich ELISA. Cell culture supernatants from MDA-MB-231 and MCF-7 were applied in a dilution series. In case of MDA-MB-231, the Cyr61 concentration of the supernatant was 1050 μg/ml and 100 μl of sample were applied to each measurement point. For simplification, the calculated Cyr61 amounts per 100 μl of MDA-MB-231 supernatant are specified on the X-axis. For each measurement point the three values from MDA-MB-231 and MCF-7 were analyzed by Student's t-test. For the Cyr61 amount of 0.125 ng a p-value of 0.031 was obtained.

FIG. 29:

Comparison of the Cysteine-rich angiogenic inducer 61 (Cyr61) signals in breast cancer cells with cells from healthy control persons.

A: Western Blot analysis of BC-M1, MDA-MB-468 (MDA-468), MDA-MB-231 (MDA-231) and mononuclear blood cells from three healthy volunteers (PBMC).

B: Cyr61 detection after cell line spiking into the blood (MDA-231 and BC-M1) and bone marrow (MDA-231) samples from healthy volunteers by immunocytochemical double staining for Cytokeratin and Cyr61.

C: Cyr61 detection DTC of breast cancer patients. The composite images are overlays of the Cytokeratin, Cyr61 and Dapi signals. Enrichment of mononuclear cells was performed by Ficoll density centrifugation. Microscope magnification: 400×.

FIG. 30:

Analysis of the Cysteine-rich angiogenic inducer 61 (Cyr61) in breast cancer cells and cells from healthy control persons. A, B: Cyr61 detection in the breast cancer cell lines BC-M1, MDA-MB-468 (MDA-468) and MCF-7 spiked into the blood samples from healthy volunteers by immunocytochemical double staining. All experiments n=3. C: Cyr61 detection in circulating tumor cells (CTC) from the peripheral blood of breast cancer patients. The positions of CTC are labeled with arrows. The composite images are overlays of the Cytokeratin, Cyr61, Dapi and CD45 (if applied) signals. For CTC analysis details, see FIG. 17. The tumor cells were isolated with a size based CTC enrichment device. Microscope magnification: 400×. D: Simulation of tumor cell dissemination from hypoxic microenvironments into well oxygenated sections of the blood. The cell lines were cultured under 1% $O_2$ for 14 days (14 d) or cultured for 14 days under 1% $O_2$ followed by cultivation for 4 h under 10% $O_2$ (14 d 4 h). The response of Cyr61 was analyzed by Western Blot (above) and quantitatively analyzed (below). The numbers display the average value of three independent experiments and standard deviation is denoted by vertical error bars. The Cyr61 levels in MCF-7 were not quantitatively analyzed, because Cyr61 was not detected in this cell line. S: standard culture condition.

FIG. 31:

Detection of Cyr61 in CTCs from the blood sample of patient 6 (see FIG. 27C). Nuclei were stained with DAPI, CD45 served as an exclusion marker for normal blood cells and pan-cytokeratin was used as CTC detection marker. The composite is an overlay of the DAPI, CD45, cytokeratin and the Cyr61 channel. The microscope magnification was 400×.

FIG. 32:

Table 3: Details of Cyr61 analyses in CTC; Example 11.

FIG. 33:

Analysis of sensitivity and specificity of the Cyr61 levels in the plasma of breast cancer patients (n=786) versus healthy women (age>50, n=124). Receiver-operating-characteristic (ROC) curves are shown for all analyzed patients (A), the stage T1 subgroup (B) and the DCIS subgroup (C). AUC: area under curve. CI: confidence interval.

EXAMPLE 1

Example 1 provides an overview over the Materials and Methods used in subsequent Examples 2 to 11.

Material and Methods

Patients. The human investigations were performed according to the Helsinki rules after approval was obtained by the ethics committee of the Medical Association Hamburg. From all patients, written informed consent was obtained prior to any study-related procedures. Samples from women with breast cancer or healthy control persons treated at the University Medical Center Hamburg-Eppendorf, Germany, were used. For CTC analyses, blood was drawn from breast cancer patients positive for distant metastases. For Cyr61 detection in blood plasma, blood from breast cancer patients who showed no detectable signs of overt metastasis at the time of diagnosis or patients with metastatic relapse was analyzed.

Bone Marrow Specimens. Bone marrow was aspirated bilaterally from both the anterior and posterior iliac crests (10 ml/site) from healthy volunteers. The following procedures were accomplished under sterile conditions. Bone marrow aspirates were washed in HBSS (Biochrom AG, Berlin, Germany) and diluted in PBS (Gibco/Life Technologies, Carlsbad, USA) and separated by density centrifugation using Ficoll Paque Plus (GE Healthcare, Munich, Germany). Mononuclear cells were collected from the interphase layer and washed twice in PBS with 10% fetal calf serum (Biological Industries, Kibbutz Beit Haemek, Israel). Cytospins were prepared by centrifuging the bone marrow mononuclear cells down onto glass slides (Superfrost plus, Glaswarenfabrik Karl Hecht KG, Sondheim, Germany; $7\times10^5$ mononuclear cells per slide). The slides were air-dried overnight and stored at −80° C. Blood samples were processed as described for bone marrow samples, and for spiking experiments cell lines were spiked into the blood or bone marrow from healthy individuals and processed as described.

Cell lines and culture conditions (standard cell culture condition). The cultivation of the DTC cell lines was essentially performed as described (11). A detailed overview of the generation, authentication and the properties of the DTC cell lines BC-M1 (obtained from the bone marrow of a breast cancer patient), LC-M1 (obtained from the bone marrow of a lung cancer patient) and PC-E1 and PC-M1 (obtained from the bone marrow of a prostate cancer patient) has been reported before (12). For detailed characterization of the cell lines see refs (12, 11). In brief, the DTC cell lines were cultured at 37° C. in a humidified environment with 5% of carbon dioxide and 10% of oxygen. The culture medium was RPMI 1640 supplemented with 10% fetal bovine serum, 2 mM L-glutamine, 10 mg/l insulin, 5.5 mg/l transferrin (all from Life Technologies, Darmstadt, Germany), 50 μg/l epidermal growth factor (EGF; Miltenyi Biotec, Bergisch Gladbach, Germany) and 10 μg/l human basic fibroblast growth factor (b-FGF, Miltenyi Biotec). The breast cancer cell line MCF-7, was obtained from the American Type Culture Collection. The breast cancer cell lines MDA-MB-468 (MDA-468), MDA-MB-231 (MDA-231) and BT-20 were purchased from Cell Lines Service (Eppelheim, Germany). The breast cancer cell line Hs578t was kindly provided by Thomas Dittmar (university of Witten/Herdecke, Germany). The bone metastatic sublines of MDA-MB-231 MDA-MB-231 SA (13) and MDA-MB-231 B02 (14) were cultivated in DMEM with 10% FCS and 2 mM L-glutamine. MDA-MB-231 B02 was kindly provided by Philippe Clézardin and MDA-MB-231 SA was kindly provided by Theresa A. Guise. The brain metastatic (in mice) subline of MDA-MB-231, MDA-MB-231 BR, was a kind gift of Frank Winkler (German Cancer Research Centre, Heidelberg, Germany) and was cultured as described for MDA-231 (see below).

MDA-468, MCF-7, PC-3, LNCAP, Du145, Hs578t, MDA-231, SCC25, Ca127 and BT-20 were cultivated in Dulbecco's Modified Eagle's Medium (DMEM) supplemented with 10% fetal calf serum and 2 mM L-glutamine (all from Life Technologies). MDA-468 cells that overexpress ErbB-2 (MDA-468 ErbB-2), the corresponding G418 resistant control cells carrying an expression vector without insert (MDA-468 control) and the YF-mutant of the ErbB-2 expression vector lacking the Y1248 phosphorylation site (MDA-468 PM) [23] were cultivated as described for MDA-468 with supplementation of 400 μg/ml G418 to the medium. All cell lines were cultured at 37° C. in a humidified environment. Cell lines that were cultivated in RPMI were kept in presence of 5% of $CO_2$, and cell lines that were cultured in DMEM were kept in presence of 10% $CO_2$. With the exception of the DTC cell lines the remaining gas mixture was atmospheric air. These cell culture conditions refer as to "standard cell culture condition" in this work. Protein samples were generated within six months after resuscitation of the cell lines.

Cultivation of the cell lines in presence of 1% $O_2$, under glucose starvation conditions or in presence of cobalt chloride. Cultivation of the cell lines in presence of 1% of $O_2$ (hypoxia) was performed using the incubator Heracell 15 (Thermo Fisher Scientific, Waltham, USA). The oxygen partial pressure was adjusted by $N_2$. When the cell lines were cultured in medium that contains no glucose (Glu$^0$), DMEM, no glucose and RPMI, no glucose (both Life Technologies) were used. For glucose starvation experiments in presence of 1% $O_2$, both conditions were combined. The other culture conditions were the same as for standard culture conditions. For stabilization of HIF-la, the cells were incubated with 150 μM cobalt chloride. For these experiments, all other parameters were the same as for standard cell culture conditions.

Brefeldin A treatment. Brefeldin A (BFA) was applied to analyze the Cyr61 secretion in cultured cells. BFA was purchased from Merck (Calbiochem, Darmstadt, Germany) and was dissolved in DMSO in a concentration of 10 mg/ml (stock solution). The stock solution was then diluted in 12 ml of cell culture medium without FCS to a final concentration of 5 μg/ml for each 75 cm$^2$ cell culture flask. The cells were incubated with BFA for 18 under standard cell culture conditions. For the control cells DMSO without BFA was applied. Centrifugation steps were performed at 0° C. until the proteins of culture medium were not dissolved in lysis buffer (9.8 M urea, 15 mM EDTA, 30 mM Tris). The culture medium was collected and centrifuged at 2000×g for 5 min. The cell pellet (detached cells) was washed with 8 ml PBS and the cells were lysed with lysis buffer and processed as described in the section below. The supernatant (12 ml per cell culture flask) was concentrated by ultraspin centrifugal devices (Vivaspin 4, 10,000 Da MWCO, PES membrane; Sartorius-Stedim, Göttingen, Germany) to a volume of 200 μl. After addition of 3 ml lysis mix the supernatant was concentrated again to a volume of 200 μl. The cell pellet was harvested as described for the cell harvest for Western Blot. The three fractions (detached cells, cell lysate and supernatant) were subjected to Western Blot as described below. For the BFA experiments 50 μg of protein were applied for Western Blot.

Size based CTC enrichment. We applied a marker-independent separation device (Parsortix, ANGLE PLC, Surrey, United Kingdom) for tumor cell enrichment. The Parsortix system uses a micro-fluidic technology in the form of a disposable cassette (Cell separation cassette cc3R, Parsortix) to capture CTCs out of the blood from cancer patients. Four mL of blood were collected into BD Vacutainers (BD Belliver Industrial Estate, Plymouth, United Kingdom). Blood was pumped automatically through the cassette. The cassette enriches CTCs based on their larger size (≥10 μm) compared to other blood components. To reduce background, the cassette was automatically washed with PBS (Life Technologies). Isolated tumor cells were harvested, cytospun on a slide (SuperFrost/Plus), and stained as described below. For cell line spiking experiments with blood from healthy persons, fresh blood was received from the Institute for Transfusion Medicine, University Medical Center Hamburg-Eppendorf. Clinical samples from breast cancer patients were drawn from breast cancer patients positive for distant metastases.

Immunocytochemical Cyr61 detection in cell lines, blood and bone marrow samples. Cell lines were spiked into blood or bone marrow samples of healthy control persons. The samples were processed as described for the analysis of the bone marrow specimen or for size based CTC enrichment. Immunocytochemical double staining was performed applying the anti-Cyr61 antibody (H78) in combination with a Cytokeratin specific antibody cocktail. The Cytokeratin antibody cocktail consisted of the antibody AE1/AE3 (mouse monoclonal; affymetrix eBioscience, Frankfurt, Germany) and C11 (mouse monoclonal; Cell Signaling Technology, Danvers, USA). Direct conjugates of AE1/AE3-Alexa Fluor488 and C11-Alexa Fluor488 were used when stated for the individual experiment. Detection of normal blood cells was performed using the anti-CD45 antibody coupled with Alexa Fluor 647 (BioLegend, San Diego, USA) when stated.

Slides were thawed 30 minutes prior to incubation with freshly diluted Solution B (135 μL solution B in 10 mL PBS) from the Epimet-Kit (AS Diagnostik, Hückeswagen, Germany) for 10 minutes. After washing with PBS three times for 3 min, cells were permeabilized for 10 minutes with 1% Triton X-100 in PBS. Another washing step was followed by blocking unspecific binding using AB-Serum (Biotest, Dreieich, Germany) (10% in PBS) for 20 minutes. The primary antibody against Cyr61 was added in a 1:50 dilution and incubated at room temperature for 1 h. The diluent was 10% AB-Serum in PBS. Slides were washed again three times with PBS, and Alexa 546 or Alexa 532 rabbit anti-mouse secondary antibody (Molecular Probes, Eugene, USA) was applied for 45 minutes diluted 1:200 in 10% AB-Serum in PBS. After three washing steps with PBS, the Cytokeratin specific antibodies were applied and incubated for 60 min. The diluent was 10% AB-Serum in PBS in all cases. For the AE1/AE3 C11 antibody cocktail the dilution was 1:700 for the AE1/AE3, and the C11 was diluted 1:200. Residual Cytokeratin specific antibodies were removed by 3 washing steps with PBS. If unconjugated Cytokeratin specific antibodies were applied, the secondary Alexa 488 rabbit antimouse fluorochrome antibody (Molecular Probes) was added in a 1:200 dilution in 10% AB-Serum and incubated for 45 min. After another washing step (3× with PBS), slides were covered with Vectashield Mounting Medium containing Dapi (Vector Laboratories, Burlingame, USA). Staining controls were run in parallel, using dilution media instead of the primary and secondary antibody, Slides were evaluated manually using the microscope Axioplan 2 (Carl Zeiss AG, Oberkochen, Germany).

Cyr61 tissue mircroarray (TMA). Protein expression of Cyr61 in clinical breast tumor samples was assessed by immunohistochemical (IHC) staining as described below. A breast cancer tissue microarray (TMA, see ref. [24]) was used for the Cyr61 expression analysis in primary tumors. For TMA generation, 0.6-mm cores were taken from invasive parts of the tumours, which had been selected by a pathologist and placed on 3 separate arrays. Sections of 6 μm were cut from the TMA blocks. The postoperative diagnosis, including evaluation of histological type and grading, was assessed by pathologists on whole formalin-fixed paraffin-embedded tissue sections. As negative control, the primary antibody was omitted in parallel sections. 245 tumor samples became eligible for evaluation, in which for 182 primary tumors clinicopathological data were available. Cyr61 immunostaining was evaluated in blinded fashion by the pathologist Sabine Riethdorf using immunoreactive score based on staining intensity and percentage of positive cells. For each tissue sample, the fraction of immunostained tumor cells was recorded, and the staining intensity was estimated on a three-step scale (0, 1, 2). Tumors were then initially categorized according to arbitrarily predefined criteria into three groups, including very low, strongly positive, and one intermediate group. The exact criteria for these groups were as follows: 0: very weak (close to detection limit or no staining at all); 1: midrange (1+ staining in (50% of cells or 2+ staining in (10% of cells); 2: strong: (1+ staining in >50% of cells or 2+ staining in >10%). The statistical analyses for comparisons in distribution of clinical and pathological variables were examined using the Pearson chi-square or the Fisher's exact test. P-values lower than 0.05 were considered statistically significant. Clinical data were assessed from the date of initial diagnosis until death or the date of the last follow-up. All statistical analyses were performed using the SPSS software version 21 (Chicago, USA).

Cyr61 immunohistochemical staining. For the IHC staining of the TMA the anti-Cyr61 antibody (H78) rabbit polyclonal (Santa Cruz Biotechnology, Santa Cruz, USA) was applied. This antibody was applied previously by another working group for TMA staining in prostate cancer [39]. Paraffin-embedded specimens on microscope slides of breast cancer patients were applied. The paraffin wax was removed by incubating the specimen at 60° C. for two hours followed by incubation of the samples two times in xylene for 10 min each. To remove the xylene the slides were incubated in 99% ethanol, followed by incubation in 96% ethanol and in 80% ethanol. Each step was performed twice, and the incubation time was 2 min for each step. After a brief washing step in water, the samples were autoclaved at 120° C. in citrate buffer (pH 6.0) for 5 minutes. Thereafter, sections were rinsed with TBST for 5 min. A peroxidase treatment was performed using the Dako REAL Peroxidase-Blocking Solution (DAKO, Glostrup, Denmark) for five minutes. After a brief washing step with TBST the anti-Cyr61 antibody was applied. The antibody was used in a 1:750 dilution using the Dako Antibody Diluent (DAKO) and incubated at 4° C. over night. Subsequently, three washing steps with TBST for 3 minutes were performed. For the detection of the primary antibody labelled polymer-HRP and the secondary antibody was used from the DAKO REAL Detection system Peroxidase/DAB (DAKO #K5001) according to the manufacturer's instructions. For chromogenic detection 3,3'-Diaminobenzidine (DAB) was applied. After a brief washing step the nuclei were visualized by hemalum staining (Merck, Darmstadt, Germany). The specimens were dried by incubation in 80% ethanol, followed by incubation in 96% ethanol, 99% ethanol and xylene. Each step was performed twice for two minutes each. For preservation of the specimen Eukitt mounting medium (Kindler, Freiburg, Germany) was used. The staining of the bone marrow metastases was performed as described for the TMA.

Immunocytochemical detection of Vimentin in cell lines. Slides were thawed 30 minutes prior to incubation with freshly diluted Solution B (135 μL solution B in 10 mL PBS) from the Epimet-Kit (AS Diagnostik, Hückeswagen, Germany) for 10 minutes. After washing with PBS three times for 3 min, cell permeabilization was performed for 10 min with 1% Triton X-100 in PBS. Another washing step was followed by blocking unspecific binding using AB-Serum (Biotest, Dreieich, Germany) (10% in phosphate buffered saline) for 20 minutes. For the detection of Vimentin the anti-Vimentin antibody (BD Pharmingen, Erembodegem, Belgium; mouse monoclonal clone RV202) that was also used for western blot was applied. The anti-Vimentin antibody was diluted 1:100 in 10% AB-Serum in PBS and incubated for 60 min. The diluent was Dako Antibody Diluent with Background Reducing Components (DAKO). As secondary antibody the Alexa 546 goat anti-mouse fluorochrome antibody was diluted 1:200 in 10% AB-Serum in PBS and incubated for 45 min. After another washing step (3× with PBS), slides were covered with Vectashield Mounting Medium containing Dapi (Vector Laboratories). Staining controls were run in parallel, using dilution media instead of the primary and secondary antibody, Slides were evaluated manually using the microscope Axioplan 2 (Carl Zeiss AG, Oberkochen, Germany).

Cell Harvest and Sample Procurement for Western Blot. Cells were washed three times with 37° C. prewarmed phosphate buffered saline, harvested in 300 μl of lysis buffer per 75 cm² cell culture flask. The cell lysates were homogenized on ice by ultrasonic treatment using the ultrasonic device UP50H (Hielscher, Teltow, Germany) by 3 identical steps (amplitude 100%; 10 s) and incubated at room temperature for 1 h followed by centrifugation (15.000 g at room temperature for 5 min) and collection of the supernatant. Peripheral blood mononuclear cells (PBMCs) were washed with 1 ml of PBS. The cells were then incubated in lysis mix and homogenized by ultrasonic treatment. Subsequently proteins were purified by precipitation using 600 μl of precipitant (component of the 2-D Quant Kit, GE Healthcare, Uppsala, Sweden) per 250 μl of the sample and co-precipitant (component of the 2-D Quant Kit) in the same amount (17). The purified proteins were dissolved in 100 μl of 9.8 M urea and solubilized for 1 h at room temperature.

Protein precipitation from blood plasma samples was performed as described before for cell lines (33). The precipitated proteins were dissolved in 9.8 M urea.

The protein concentration was determined using the Pierce BCA Protein Assay Kit (Pierce, Rockford, USA) according to the manufacturer's instructions and using BSA as the standard. The samples were stored at −80° C. The sample quality and the quality of the BCA-test results were confirmed by colloidal Coomassie stained SDS gels. The staining procedure was performed according to Neuhoff (18).

SDS-PAGE and Western Blot. Protein separation was done with the Novex XCell Sure-Lock mini system (Invitrogen, Groningen, Netherlands) or the Protean II xi cell (Bio-Rad, Hercules, USA) using 10% polyacrylamide separation gels and a Laemmli buffer system. Samples were diluted in SDS-sample buffer, heat denatured at 95° C. for 5 min and loaded onto the gels. The molecular size standard was the peqGOLD protein-marker V (Peqlab, Erlangen, Germany). For Western Blot analysis 40 μg of protein per sample were applied, except where other specified. After SDS-PAGE the proteins were transferred to Immobilon-P$^{SQ}$ membranes (Millipore GmbH, Schwalbach, Germany). The proteins were transferred by tank blot using the mini VE vertical electrophoresis system equipped with tank blot transfer units (GE Healthcare, Uppsala, Sweden). The primary antibodies were applied according to the instructions of the manufacturer using the dilutions described in the section "Antibodies used for western blot". If no viable information from the supplier was available, the membrane was blocked with 5% lowfat powdered milk (Roth, Karlsruhe, Germany) in TBST (blocking buffer) for one hour with gentle agitation. In these cases the primary antibodies were diluted in blocking buffer and applied to the membranes at 4° C. with gentle agitation over night. The appropriate secondary antibodies conjugated with horseradish peroxidase (all DAKO, Glostrup, Denmark) were used at dilutions from 1:500 to 1:10,000 depending on the signal intensity for the individual experiment. All secondary antibodies were diluted with blocking buffer. Bands were visualized using the ECL Prime Western Blotting Detection Reagent and X-ray films (both GE Healthcare) in accordance to the manufacturer's instructions. X-ray films were digitized using the GS-700 imaging densitometer (Bio-Rad). Densitometric analysis was performed using the Quantity one software (Bio-Rad). Each reaction was performed in biological triplicate. The membranes were stripped using the following stripping buffer: 7.56 g Tris, 20 g SDS, 7.8 g 2-mercaptoethanol, adjustment to pH 9.5 using HCl, H$_2$O ad 1 l. Prior to use 0.1 g DTT was added to 25 ml of the stripping buffer. The membranes were incubated at room temperature with gentle agitation for one hour. After washing with TBST the membranes were incubated with blocking buffer for one hour and a different primary antibody was applied.

Antibodies used for western blot. Antibodies were purchased from the following suppliers: Anti-AE1/AE3 antibody, mouse monoclonal, dilution 1:10,000. Affymetrix eBioscience, Frankfurt, Germany. BD Biosciences, Franklin Lakes, USA: anti-Integrin αv (CD51), mouse monoclonal, clone Clone 21/CD51, dilution 1:500. BD Pharmingen, Erembodegem, Belgium: Anti-Vimentin antibody, mouse monoclonal clone RV202, dilution 1:5,000. Cell Signaling Technology, Danvers, USA: anti-alpha-Tubulin (11H10) antibody, rabbit monoclonal, dilution 1:10,000. Anti-BiP (C50B12) antibody, rabbit monoclonal (BiP is a synonym for Grp78), dilution 1:1,000. Anti-Cyr61 antibody, rabbit polyclonal, dilution 1:1,000 (MDA-MB-231, Hs578t, BC-M1, LC-M1) other cell lines 1:500. Anti-HIF-1α (D2U3T), rabbit monoclonal, dilution 1:1,1000. Anti-Lamin A/C antibody, rabbit polyclonal, dilution 1:1000. Anti-PD-L1 (E1L3N) antibody, rabbit monoclonal, dilution 1:1000. The anti-Integrin antibodies were taken from the Integrin antibody sampler kit (Cell Signaling Technology), with the exception of anti-Integrin αv. The applied dilutions were: anti-Integrin α5: 1:1,000, Integrin β4 (D8P6C) XP 1:1,000, Integrin α4 (D2E1) XP 1:500, Integrin β1 (D2E5) 1:2,000, Integrin β3 (D7X3P) XP 1:2,000, Integrin β5 (D24A5) 1:1,000.

Abcam, Cambridge, United Kingdom: Anti-ErbB-2 antibody, mouse monoclonal (clone CB11), dilution 1:500. Anti-CXCR4 antibody, rabbit polyclonal, dilution 1:4,000. BD biosciences, Heidelberg, Germany: Anti-Integrin αv antibody, mouse monoclonal (clone 21/CD51), dilution 1:500. Cell Signaling Technology: Anti-AKT antibody, rabbit polyclonal, dilution 1:5,000. Anti-phospho AKT antibody (Ser473), rabbit monoclonal (clone 193H12), dilution 1:500. Anti-alpha-Tubulin antibody, rabbit monoclonal (clone 11H10), dilution 1:10,000. Anti-BiP antibody, rabbit monoclonal (clone C50B12) (BiP is a synonym for Grp78), dilution 1:1,000. Anti-Cyr61 antibody, rabbit polyclonal, dilution 1:1,000 (MDA-MB-231, Hs578t, BC-M1, LC-M1) other cell lines 1:500. Anti-EGF receptor antibody, rabbit monoclonal (clone D38B1), dilution 1:1,000. Anti-HIF-1α, rabbit monoclonal (clone D2U3T), dilution 1:1,000. Anti-Integrin α5 antibody, rabbit polyclonal, dilution 1:1,000. Anti-Integrin β4 antibody, rabbit monoclonal (clone D8P6C), dilution 1:1,000. Anti-Integrin α4 antibody, rabbit monoclonal (clone D2E1), dilution 1:500. Anti-Integrin β1 antibody, rabbit monoclonal (clone D2E5), dilution 1:2,000. Anti-Integrin β3 antibody, rabbit monoclonal (clone D7X3P), dilution 1:2,000. Anti-Integrin β5 antibody, rabbit monoclonal (clone D24A5), dilution 1:1,000. Anti-Lamin A/C antibody, rabbit polyclonal, dilution 1:1,000. Anti-PD-L1 antibody, rabbit monoclonal (clone E1L3N), dilution 1:2,000. Epitomics, Burlingame, USA: Anti-E-Cadherin antibody, rabbit monoclonal (clone EP700Y), dilution 1:20,000. Merck (Calbiochem), Darmstadt, Germany: Anti-c-ErbB-2/c-Neu (Ab-3) antibody, mouse monoclonal (clone 3B5), dilution 1:4,000. Micromet, Munich, Germany: Anti-pan-cytokeratin antibody, mouse monoclonal (clone A45/BB3), dilution 1:10,000. Novus Biologicals, Littleton, USA: Anti-N-Cadherin antibody, rabbit monoclonal (clone EPR1792Y), dilution 1:10,000. Santa Cruz Biotechnology, Santa Cruz, USA: Anti-EGFR (1005) antibody, rabbit polyclonal, dilution 1:5,000. Anti-Cyr61 antibody (H78), rabbit polyclonal, dilution 1:1,000 (MDA-MB-468, MCF-7, PBMC) or 1:10,000 (all other cell lines). Anti-Cyr61 antibody (H2), mouse monoclonal, dilution 1:1,000 (MDA-MB-468, MCF-7) or 1:10,000 (all other cell lines).

Stable isotope labelling with amino acids in cell culture (SILAC). For the analysis of the protein expression profile the breast cancer cell lines MDA-468 and BC-M1 were selected and cultured as described for standard cell culture conditions except other specified. If no other stated, the instructions from the Pierce SILAC Protein Quantitation Kit (Pierce Biotechnology) were followed. BC-M1 was selected for the protein labelling because RPMI—other than DMEM—contains proline and hydroxyproline, evading from potential false labelling of proline without artificial supplementation of the medium with proline. For BC-M1 RPMI Media for SILAC and for MDA-468 DMEM Media for SILAC were used and were supplemented with 10% dialyzed fetal bovine serum (all from Pierce Biotechnology) and with 2 mM L-glutamine (Life Technologies). The RPMI was further supplemented with 10 mg/l insulin, 5.5 mg/l transferrin (both from Life Technologies), 50 μg/l EGF and 10 μg/l b-FGF (both Miltenyi Biotec). The proteins of BC-M1 were labelled using $^{13}$C$_6$-Arginine-HCl and $^{13}$C$_6$-Lysine-2HCl (both Pierce Biotechnology) in a concentration of 100 mg per litre RPMI. The DMEM for MDA-468 was supplemented with Arginine-HCl and Lysine-2HCl (both Pierce Biotechnology). The amino acids were added to the media after sterile filtration. Hereinafter these media are called SILAC-media (heavy and light). Morphological analysis of the cells by microscopy revealed no detectable morphologic alteration of the cells cultured in SILAC medium compared with the cells cultured under standard cell culture condition until passage 7 (including; that is ±18 days).

Preparative sample preparation for mass spectrometry. For preparative labelling of the proteins the cells were cultured for 3 passages in SILAC media in 75 cm$^2$ cell culture flasks under standard conditions. Depending on the cell growth the cells were split in 1:3 or 1:4 ratio every 2-3 days. Four flasks each of passage three that were cultivated at different dates were analyzed. The following protocol is described for one flask. The cell harvest was performed as described for Western Blot and the cells were lysed in 400 μl of lysis mix (8 M urea/15 mM EDTA/30 mM Tris). The lysate was homogenized by ultrasound treatment using the ultrasonic device UP50H (3 identical steps (amplitude 100%; 10 s). Subsequently the proteins were allowed to solve by incubation of the sample at room temperature for 1 h followed by centrifugation (12.000 g at room temperature for 5 min) and collection of the supernatant. After that the sample was supplemented with 0.05 volume of 1M DTT/1M Tris and incubated at 56° C. for 20 min with vigorous shaking. DTT also served as a scavenger for the potential formation of isocyanate ions from urea. The irreversible blocking of the SH-groups was carried out by addition of IAA to a final concentration of 200 mM. The pH value was adjusted to pH 9.5 using 2M Tris. Then the sample was incubated at room temperature and protected from light for 30 min with vigorous shaking. Afterwards the proteins were purified by precipitation using 1.2 ml of precipitant (component of the 2-D Quant Kit, GE Healthcare) per 500 µl of the sample and co-precipitant (component of the 2-D Quant Kit) in the same amount as the precipitant (17). The proteins were pelleted by centrifugation (16.000 g for 5 min) and washed with 1 ml of 80 mM Tris in 80% acetone. Residual contaminating substances were removed by an additional washing step with 1 ml of 80 mM acetone. The purified proteins were dissolved in 100 µl of 9.8 M urea and solubilized for 1 h at room temperature. This was followed by determination of the protein concentration using the BCA test. Samples were diluted with 9 volumes of 100 mM $NH_4HCO_3$ pH 8.3. The proteins were digested by Trypsin (Trypsin sequencing grade, Roche, Mannheim, Germany) by addition of 1 µg Trypsin per 20 µg of protein of the sample. For subsequent analyses 380 µg of protein of each cell line (MDA-468 and BC-M1) was combined in a 1:1 ratio. Thereafter the sample was incubated at 37° C. over night with vigorous shaking.

Peptide desalting. After tryptic digest the peptides were desalted using a reversed phase cartridge (Oasis HLB Plus Short Cartridge, 225 mg, 60 µm, Waters, Manchester, UK). The cartridge was conditioned with 3 ml 100% methanol (MeOH) and equilibrated with 3 ml 0.2% formic acid (FA), 5% MeOH (wash buffer, dissolved in HPLC-$H_2O$) using 5 ml syringes. Tryptic peptides were dissolved in 1 ml wash buffer and loaded on the cartridge using a 1 ml syringe. After loading the cartridge was washed with 3 ml wash buffer and the peptides were eluted with 1.5 ml 60% MeOH using 3 ml syringes. The eluate was evaporated using a speed vac.

OFFGEL fractionation. The desalted peptides were fractionated according to their isoelectric points using an OFF-GEL fractionator device (Agilent Technologies, 3100 OFF-GEL fractionator, Waldbronn Germany). For isoelectric focusing (IEF) the 24-well setup and IPG strips with a linear gradient pH 4-7, 24 cm, (GE Healthcare, Munich) were used. The sample was dissolved in 3 ml loading buffer (20% MeOH, 1% IPG-buffer [pH 4-7], dissolved in HPLC-$H_2O$) and 150 µL sample volume was added in each well. To protect the fractions from desiccation during the focusing process 100 µL of loading buffer without sample was added to the fractions 1 and 24. For the fractions 2 and 23 50 µL of loading buffer was added. The IEF was performed with a maximum current of 50 µA and typical voltages ranging from 300 V to 2500 V until a total of 50 kVh was attained. After the IEF the fractions were collected and dried using a speed vac system.

nanoUPLC-ESI-QTOF-MS/MS analysis. Mass spectrometric analyses were performed on a QTOF mass spectrometer (QTOF Premier, Micromass/Waters, Manchester, UK) equipped with a nanoUPLC (nanoAcQUITY, Waters, Manchester, UK). For QTOF measurements concentrated samples were dissolved in 30 µl 0.1% FA and 4 µL were loaded on a trapping column (nanoAcquity UPLC column, C18, 180 µm×20 mm, Waters, Manchester, UK). After trapping, the trapping column was washed for 5 min with 2% ACN, 0.1% FA (5 µL/min). The peptides were eluted onto the separation column (nanoAcquity UPLC column, BEH 130 C18, Waters; 100 µm×100 mm, 500 nL/min, gradient: A, 0.1% formic acid in HPLC-$H_2O$; B, 0.1% formic acid in acetonitrile, 2-50% B in 87 min). The spray was generated from a fused-silica emitter (I.D. 10 µm, New Objective, Woburn, USA) at a capillary voltage of 1520 V, a source temperature of 100° C. and a cone voltage of 40 V in positive ion mode. Data were recorded in data dependant acquisition mode (DDA). MS survey scans were performed over an m/z range from 400-1500 with a scan-time of 0.6 s and an interscan delay of 0.05 s. The three most abundant signals were used for fragmentation. MS/MS spectra were obtained from 100-1500 m/z with a scan-time of 3.2 sec and a collision ramp from 15-35 eV. An online exclusion was used to prevent multiple fragmentation events (exclusion time: 60 sec, exclusion window: +/−0.1 m/z). For calibration, a lockspray spectrum was recorded every 10 seconds (1 pMol/µL [Glu1] Fibrinopeptide B (Sigma, Munich, Germany)) over an m/z range from 100-1500 using a collision energy of 22 eV.

Directed Cyr61 peptide nanoUPLC-ESI-QTOF-MS/MS analysis was performed as described above with the following modifications. The peptides were eluted on a separation column (nanoAcquity UPLC column, BEH 130 C18, Waters; 75 µm×200 mm, 200 nL/min, gradient: A, 0.1% formic acid in HPLC-$H_2O$; B, 0.1% formic acid in acetonitrile, 2-50% B in 87 min). MS survey scans were performed over an m/z range from 400-1500 with a scan-time of 0.6 s and an interscan delay of 0.05 s. The two most abundant signals were used for fragmentation. MS/MS spectra were obtained from 100-1500 m/z with a scan-time of 0.95 s and a collision ramp from 20-32 eV. For Cyr61 detection an inclusion list was used: m/z 1180.6389 (+/−0.1 Da), retention time: 4174.8 s (+/−90 s), scan-time: 4.95 s, interscan delay: 0.05 s, collison ramp: 20-32 eV.

Peptide Identification. For peptide identification the raw spectra were smoothed (savitzky golay, smooth window channel: 3, number of smooths: 2), centered (min peak width at half height: 4, centroid to: 80%) and lock mass corrected using Protein Lynx Global Server version 2.5.2 (Waters, Manchester, UK). The resulted peak lists were exported as an mzML file. The identification was carried out with The OpenMS Proteomic Pipeline (TOPP) (19) using the graphical user interface TOPPAS, which is part of the open source software package OpenMS (20). The mzML files were searched against a human decoy database (uniprot, protein knowledgebase (UniProtKB), www.uniprot.org) using two different search engines (the open mass spectrometry search algorithm (OMSSA) (21), XTANDEM (22) with the following parameters: precursor mass tolerance was set to 35 ppm and fragment mass tolerance was set to 0.1 Da. Furthermore, one missed cleavage was allowed and an oxidation of methionine, a carbamidomethylation on cysteine as well as $^{13}C_6$-label on both lysine and arginine were considered as variable modifications. Afterwards posterior error probabilities were estimated using the ID-PostErrorProbability-tool and consensus identifications were computed based on the peptide identifications from the two search engines using the ConsenusID-tool (23). With the FalseDiscoveryRate-tool q-values were calculated and the threshold for correct peptide identification was set to a q-value of 0.05. Finally the peptide identification files were exported as idXML-files.

SILAC quantification. For SILAC quantification the raw data files were converted to mzXML files in profile mode using the massWolf file converter. Signal processing was performed using TOPPAS (19). First mzXML files were converted to mzML files using the FileConverter tool. For subsequent data processing the mzML files were filtered with the FileFilter tool (only MS1 level, rt-range [s]: 1800-5000). The filtered raw data were smoothed using Noise-FilterSGolay (frame length: 13, polynomial order: 4). The SILAC pairs were identified and quantified using the SILA-CAnalyzer tool using the following parameters. The retention time threshold was set to 50 seconds and an intensity cutoff of 5 counts was used. The intensity correlation was set to 0.6 and a model deviation of 2.5 was considered. A peptide required at least three isotopic peaks and maximal seven isotopic peaks to be take into account by the SILA-CAnalyzer. The label was set to $^{13}C_6$ for lysine and arginine and for detection one missed cleavage was allowed. The results were exported as consensusXML files. The data set of the identified peptides, which was handled as idXML-files, were matched to the corresponding SILAC pairs using the IDMapper tool and exported as csv files. CSV files were loaded into Mathematica. For each SILAC pair, the ratio was calculated by dividing the intensity of the light peptide by the intensity of the heavy. Peptide ratios were grouped by the protein they were assigned to and the mean ratio of peptides was used as the protein ratio.

For the data analysis only peptide identifications were considered that matched to one single protein (unique peptides). Proteins were only analyzed further, when unique peptides were detected in at least three of the four biological replicates. Peptides that derived from the C-terminus of a protein that ended not with K or R were excluded manually. The average value and standard deviation for all detected peptides for one protein was calculated. Proteins that considered as differentially expressed must exceed a value of 2.0 in terms of fold changes with statistical significance with $p < 0.05$ (Student's t-test).

Determination of growth rates by cell counting. For the determination of the growth rates, tumor cells were first cultivated in 6-well plates under standard conditions. 15,000 to 25,000 cells were employed per well and allowed to grow for one day. For the determination of the starting cell number the cell number of one well was determined as follows. The cells were detached by trypsinization and transferred into a Neubauer counting chamber using the vital stain trypan blue to identify dead cells. The cell number was determined for nine squares and the cell number per well was calculated for these values. The resulting cell number served as the value for the starting cell number (t=0 h) for the individual experiment. Cells were cultivated in parallel in additional wells and treated as described in the cell culture sections. After the appropriate time points the cells were harvested and counted as described. Biological replicates were carried out in the same way in independent experiments.

Morphologic analyses of the cells under glucose starvation were carried out using the microscope Axiovert 25 (Carl Zeiss AG).

Enzyme-linked immunosorbent assay (ELISA). Sample procurement: Blood plasma from healthy control persons or breast cancer patients was obtained by centrifugation of fresh blood samples at 2500×g for 15 min. Cell culture supernatant was clarified by centrifugation at 2500×g for 15 min. For whole cell lysate of cell lines, the cell were lysed with LPIP buffer (140 mM NaCl, 50 mM Tris HCl, pH 7.5, 1 mM EDTA, 0.05% NP40, 10% glycerol) and the cell lysates were applied in an appropriate dilution. The diluent was PBS. In case of plasma and cell culture supernatant 100 µl of undiluted sample volume was applied. Recombinant human Cyr61 protein was purchased from Abnova (Taipei, Taiwan). The protein concentration was determined using the Pierce BCA Protein Assay Kit.

For the detection of Cyr61 in tumor cell samples an ELISA was established. The pipeting steps were performed with a 100 µl multichannel pipette. First, the 96 well plates (96 well plate flat bottom, costar, Sigma Aldrich) were coated with the anti-Cyr61 antibody (anti-Cyr61 antibody (H78) rabbit polyclonal, Santa Cruz Biotechnology). The anti-Cyr61 antibody was diluted to a concentration of 3 µg/ml in PBS (Gibco/Life Technologies) and 25 µl of the diluted antibody was added to each well. The plate was incubated at 4° C. over night. To remove unbound antibody, the wells were washed with 100 µl of volume three times. The first time the wells were washed with PBS, followed by two steps using PBS with 0.02% Tween 20 (Roth, Karlsruhe, Germany). Next, the wells were blocked with blocking buffer (5% nonfat dry milk [Roth], in PBS with 0.02% Tween) using 30 µl of blocking buffer per well for two hours at room temperature. This was followed by three washing steps using 100 µl of volume. The first time the wells were washed with PBS, followed by two steps using PBS with 0.02% Tween 20. For the Cyr61 detection in the samples 100 µl of sample volume was added to each well and incubated at room temperature for two hours. Next, the wells were washed with the washing steps as described above. The secondary antibody (goat anti-rabbit IgG-AP, Santa Cruz Biotechnology) was diluted 1:3,000 with blocking buffer and 30 µl of the dilution was added to each well followed by incubation for one hour at room temperature. The wells were washed with the washing steps as described. After addition of 100 µl of prewarmed substrate solution (para-Nitrophenyl phosphate one component microwell substrate solution, Southern Biotech, Birmingham, USA) to each well, the reaction was incubated in the dark at room temperature for 30 minutes. The reaction was stopped by addition of 15 µl of 3 N NaOH). The samples were analyzed using on an ELISA reader (NanoQuant infinite M200 pro, Tecan, Mannedorf, Switzerland) at 405-620 nm. Statistical analyses of the Cyr61 levels between the patient groups were performed with one-way ANOVA test using the program Orig-inPro 8.0 (Northampton, USA), where p-Values<0.05 were considered significant.

A modification of the Cyr61 ELISA to a sandwich ELISA was recently established which was performed as follows. The assay was performed in F8 maxisorp loose stripes (Thermo Fisher, Waltham, USA). The anti-Cyr61 antibody (H78) was diluted to a concentration of 6 µg/ml in PBS and 25 µl of the diluted antibody was added to each well. The assay was incubated at 4° C. over night. Next, the wells were washed with 100 µl PBS and two times with 100 µl PBS with 0.02% Tween 20 (Roth). Subsequently, the wells were blocked with blocking buffer using 30 µl per well and incubated for 2 h at room temperature. The wells were washed again with 100 µl PBS and two times with 100 µl PBS with 0.02% Tween 20 (Roth). After that, 100 µl of sample, for example undiluted plasma, were added to each well and incubated at room temperature for two hours followed by three washing steps as described. As detecting antibody, the anti-Cyr61 antibody, mouse monoclonal (clone 365108) from R & D Systems (Minneapolis, USA) was used. This antibody was diluted in PBS to a concentration of 30 µg/ml and 25 µl of the dilution was applied to each well followed by incubation at 4° C. over night. Unbound antibody was removed by three washing steps as described. As secondary antibody, a polyclonal goat anti-mouse antibody coupled with horseradish peroxidase (P0447, Dako, Glostrup, Denmark) was diluted 1:250 with blocking buffer and 30 µl of the dilution were applied to each well. The secondary antibody was incubated at room temperature for one hour. The assay was washed three times as described. As substrate 100 µl of TMB one component HRP microwell substrate (E102, Bethyl Laboratories, Montgomery, USA) was added to each well. The incubation was carried out protected from light for 15 min followed by stopping the reaction by addition of 100 µl of 1 N sulphuric acid. The extinction at 450 nm was detected using the ELISA reader NanoQuant infinite M200 pro.

Immunoprecipitation. For the analysis of Cyr61 by immunoprecipitation $1-2 \times 10^7$ cells were applied. After cell harvest the cells were pelleted at 1450 rpm for 15 minutes at 4° C. The supernatant was discarded and the cells were washed with PBS and pelleted by centrifugation. For cell lysis, 100 µl of LPIP buffer, 5 µl 5 M sodium chloride and 105 µl of water was added to the cell pellet. After homogenization, the sample was incubated for 5 minutes at 4° C., followed by centrifugation at 10.000×g for 15 min at 4° C. The pellet was discarded.

Next, 400 µl of LPIP buffer were added to each tube. For the precipitation of Cyr61, 20 µl of the anti-Cyr61 antibody (anti-Cyr61 antibody (H78) rabbit polyclonal, Santa Cruz Biotechnology) was applied. For the IgG control assay, 10 µl of normal rabbit IgG-AC (Santa Cruz Biotechnology) was used. The samples were incubated in a rotator at 4° C. After 3 h of incubation 25 µl beads (Protein A Sepharose, CL—4B/GE Healthcare) were added to each assay and incubated on a rotator at 4° C. for one additional hour. Subsequently, the bead-antibody conjugates were washed using 1 ml of LPIP buffer for each assay, followed by centrifugation at 2.000 rpm at 4° C. The washing was repeated four times. The antibodies were cleaved by application of 50 µl sample buffer and 5 µl of reducing agent (NuPAGE LDS Sample Buffer 4×, NuPAGE Sample Reducing Agent 10× both Gibco/Life Technologies) to the sample followed by incubation at 70° C. in a thermocycler. After spinning down at 2000 rpm at 4° C. for 1 minute the samples were separated by SDS-PAGE. SDS-PAGE was performed using the XCell SureLock Mini-Cell 1 unit, Thermo Fisher, Waltham, USA), TruPage precast gels 4-12%, 12 well, and TruPAGE TEA-Tricine SDS Running Buffer (both Sigma Aldrich). Proteins were transferred by the XCell II Blot Module (Thermo Fisher) onto Protan nitrocellulose membranes (GE Healthcare) following the manufacturer's instructions. Cyr61 was detected using the anti-Cyr61 antibody, mouse monoclonal (clone 365108) from R & D Systems (Minneapolis, USA) at a dilution of 1:500.

Improved Enzyme-Linked Immunosorbent Assay (ELISA).

Sample procurement: Blood plasma from healthy control persons or breast cancer patients was obtained by centrifugation of fresh blood samples at 2500×g for 15 min. Cell culture supernatant was clarified by centrifugation at 2500×g for 15 min. For whole cell lysate of cell lines, the cell were lysed with LPIP buffer (140 mM NaCl, 50 mM Tris HCl, pH 7.5, 1 mM EDTA, 0.05% NP40, 10% glycerol) and the cell lysates were applied in an appropriate dilution. The diluent was PBS (Gibco/Life Technologies). In case of plasma samples, 2.5 µl of sample volume was applied. Recombinant human Cyr61 protein was purchased from Abnova (Taipei, Taiwan). Protein concentrations were determined using the Pierce BCA Protein Assay Kit.

The pipeting steps were performed with a 100 µl multichannel pipette using TC-Plattes 96 Well, Standard, F (Sarstedt). For the coating of the wells, the anti-Cyr61 antibody H2 from Santa Cruz Biotechnology) was applied. The antibody was diluted 1:250 in Dulbecco's Modified Eagle Medium (DMEM) with 10% FCS and 35 µl of the diluted antibody was applied to each well. The plate was incubated at 4° C. over night with gentle agitation. To remove unbound antibody, the wells were washed with 100 µl of volume three times. The first time the wells were washed with PBS, followed by two steps using PBS with 0.02% Tween 20 (Roth, Karlsruhe, Germany). Next, the unspecific binding was blocked with blocking buffer (5% nonfat dry milk [Roth], in PBS with 0.02% Tween) using 100 µl of blocking buffer per well. The assay was incubated with gentle agitation at 4° C. over night. Next, three washing steps using 100 µl of volume each as described were performed. For the incubation with plasma samples, 2.5 µl of plasma diluted in 97.5 µl DMEM with 10% FCS were added to the wells and incubated for two hours at room temperature with gentle agitation. This was followed by three washing steps using 100 µl of volume each as described. Next, the anti-Cyr61 antibody H78 (Santa Cruz Biotechnology) was added to the wells. The anti-Cyr61 antibody was diluted 1:500 in DMEM with 10% FCS and 35 µl of the diluted antibody was added to each well followed by incubation at room temperature with gentle agitation for two hours. This was followed by three washing steps using 100 µl of volume each as described. For detection of Cyr61, a polyclonal goat anti-rabbit immunoglobulin antibody coupled with horseradish peroxidase (Dako, Glostrup, Denmark) was diluted 1:250 with blocking buffer and 35 µl of the dilution were applied to each well. The reaction was incubated at room temperature for one hour with gentle agitation. This was followed by three washing steps using 100 µl of volume each as described. Next, 100 µl of TMB one component HRP microwell substrate (Bethyl Laboratories, Montgomery, USA) was added to each well. The incubation was carried out protected from light at room temperature for 15 min. The reaction was stopped by addition of 100 µl of Stop Solution for TMB Substrates (Immunochemistry Technologies, Bloomington, USA) and incubation in the dark with gentle agitation for 15 min. The extinction at 450/620 nm was detected using the ELISA reader NanoQuant infinite M200 pro (Tecan, Mannedorf, Switzerland). The OD values were converted to Cyr61 concentrations using recombinant and purified Cyr61 protein as a standard.

Improved Cyr61-immunoprecipitation (IP). For the isolation of Cyr61, 100 µl of freshly harvested cell culture supernatant that was 72 h on MDA-MB-231 cells was used. The beads (Protein A Sepharose, CL—4B; GE Healthcare, Munich, Germany) were suspended in 500 µl of cold IP buffer (LPIP buffer with complete ULTRA Tablets protease inhibitor from Roche, Mannheim, Germany). Next, 4 µg of the mouse monoclonal anti-Cyr61 antibody H2 (Santa Cruz Biotechnology) was added. In the control assay the anti-Cyr61 antibody was replaced by normal mouse IgG-AC (Santa Cruz Biotechnology). The assays were incubated on a rotator at 4° C. overnight. To remove unbound antibody, the beads were washed five times with 1 ml of IP buffer (2,000×g for 1 minute). The beads were suspended in 100 µl of cell culture supernatant and 900 µl of cold IP buffer and incubated on a rotator at 4° C. for three days. Subsequently, the bead-antibody conjugates were washed using 1 ml of IP buffer for each assay, followed by centrifugation (2,000×g for 1 minute). The washing was repeated four times. The antibodies were cleaved by application of 100 µl Laemmli sample buffer to the pelleted beads and heated to 70° C. for ten minutes. After centrifugation (10,000×g for 1 minute) an aliquot of the supernatant was analyzed by Western Blot for Cyr61 using the anti-Cyr61 antibody H78 (Santa Cruz Biotechnology) for the detection of Cyr61.

EXAMPLE 2—DISCOVERY OF CYR61 AS MESENCHYMAL MARKER

The mDTC cell lines from the bone marrow of cancer patients (BC-M1: breast cancer, LC-M1: lung cancer, PC-E1 and PC-M1: prostate cancer) served as useful models to study DTC biology (12). In particular, BC-M1 and LC-M1 exhibited mesenchymal characteristics, such as high expression of vimentin but retained some epithelial attributes such as low expression of certain cytokeratins (FIG. 1A). In contrast, the basal-like MDA-468 breast cancer cells have a predominant epithelial phenotype but contain a subpopulation of tumour cells that are enriched for mesenchymal marker proteins like vimentin (see below). To get deeper insight into the dissemination process, we analyzed the protein profile of BC-M1 and MDA-468 by SILAC (stable isotope labeling with amino acids in cell culture) and LC-MS/MS mass spectrometry. BC-M1 cells were metabolically labeled, whereas MDA-468 was cultivated in presence of the corresponding light isotopes. The only detected protein that fulfilled our demands was Cyr61. Cyr61 was overexpressed in BC-M1 compared with MDA-468 in these experiments (Table 1 in FIG. 2; FIG. 1B). Lamin-A/C is presented as an example for a protein that was not differentially expressed between BC-M1 and MDA-468 in the LC-MS/MS approach. These results were confirmed by Western Blot (FIG. 1C, D). Thus, we focused on Cyr61 in the subsequent analyses.

EXAMPLE 3—HIGH CYR61 PROTEIN EXPRESSION IN TUMOR CELLS WITH MESENCHYMAL ATTRIBUTES

Tumor cells with a pronounced mesenchymal phenotype (Hs578t, BC-M1 and LC-M1) are positive for Cyr61 (FIG. 1C, D). The breast cancer cell line MDA-MB-231 (MDA-231), which shares epithelial and mesenchymal attributes, also displays high levels of Cyr61. In contrast, the cell lines with epithelial attributes (MDA-468, MCF-7) express Cyr61 at very low levels. The Cyr61 levels in the prostate cancer cell lines PC-E1 and PC-M1 (FIG. 1E) were lower than in BC-M1. From our cell line analyses we therefore assume that mCTC/mDTC are positive for Cyr61 together with slight expression of cytokeratins.

EXAMPLE 4—CYR61 RESPONSE TO MICROENVIRONMENTAL STRESS AND COEXPRESSION WITH PD-L1

Figure 5:
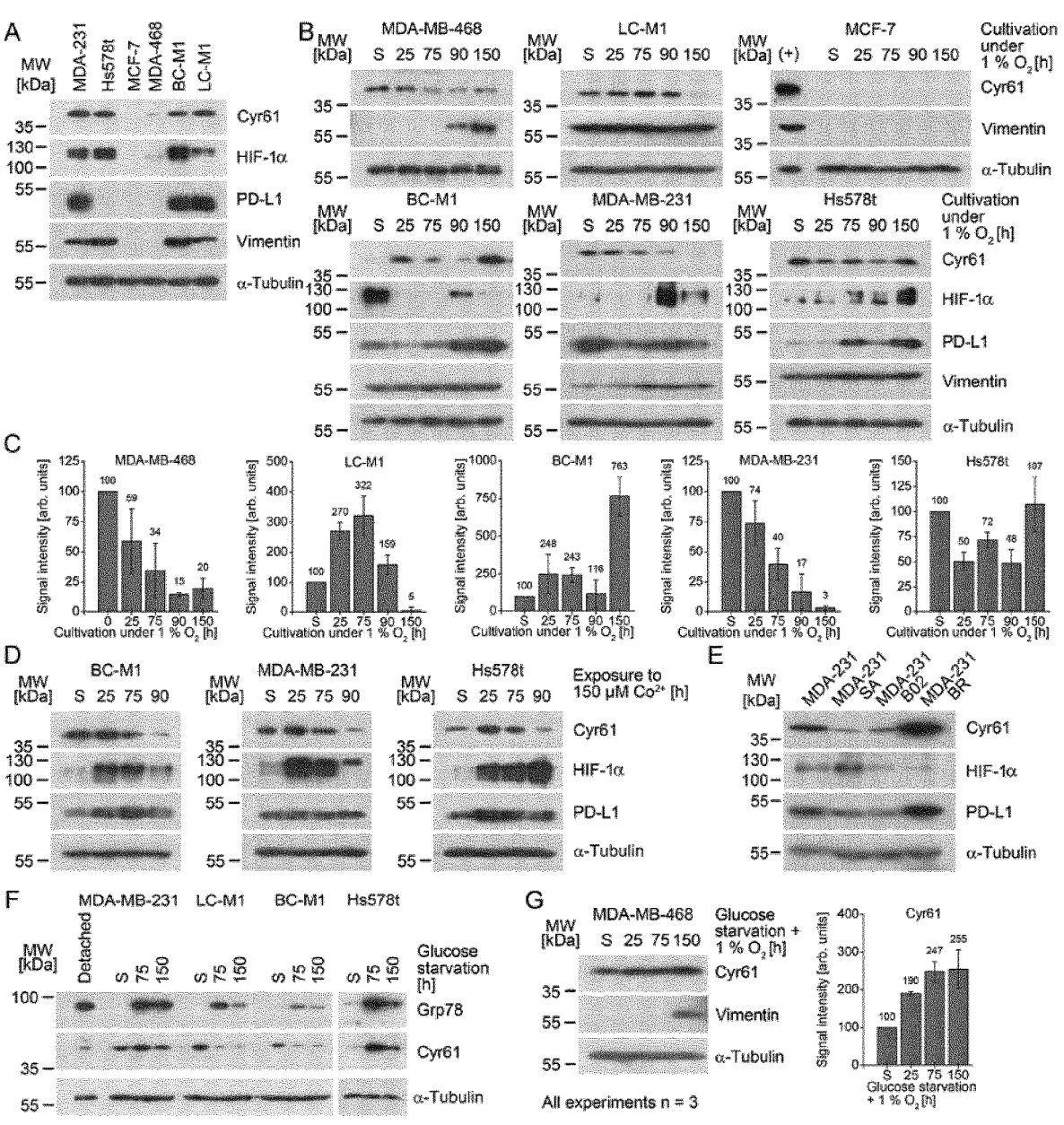

We established a model system for the analysis of Cyr61 levels in the course of the dissemination of cancer cells to the bone marrow with emphasis on hypoxia (FIG. 5).

We observed a remarkably close co-expression of Cyr61 and HIF-1α (hypoxia-inducible factor 1-alpha) at the starting conditions of our model system (standard cell culture conditions, FIG. 5A). HIF-1α is the master regulator of metabolic adaptation to hypoxia. We next modeled the settlement of DTC in hypoxic areas of the bone marrow by subjection of the cells to 1% of $O_2$ in a time series (FIG. 5B). In MDA-231 and MDA-468 downregulation of Cyr61 was accompanied by the induction of the mesenchymal marker protein vimentin during hypoxia. The inverse correlation of Cyr61 with HIF-1α suggested a HIF-1α dependent downregulation of Cyr61, but this effect was not very apparent under 1% of $O_2$. To clarify this, we treated the cells with cobalt chloride in presence of standard cell culture conditions (FIG. 5D). Cobalt ($Co^{2+}$) inhibits the interaction of HIF-1α with the von Hippel-Lindau protein leading to an accumulation of HIF-1α (24). These experiments revealed an accumulation of HIF-1α with subsequent downregulation of Cyr61. Next, we analyzed Cyr61 in the bone metastatic sublines of MDA-231 MDA-231 SA (13) and MDA-231 B02 (14) (FIG. 5E) assuming that these tumour cells had to adapt to hypoxic conditions in vivo during metastatic outgrowth. We observed an inverse correlation of Cyr61 and HIF-1α in these cell lines, which suits to the cellular responses of Cyr61 and HIF-1α upon $Co^{2+}$-treatment. We further analyzed the brain metastatic subline of MDA-231, MDA-231 BR, to test our findings on bone marrow metastasis in the context of brain metastases. MDA-231 BR exhibits the highest Cyr61 levels of all analyzed cell in this work lines that were cultured under standard culture conditions.

Hypoxia is frequently a consequence of an inefficient blood supply in tumours which is accompanied by a lack of nutrients. Therefore, we analyzed the cellular response to glucose starvation (FIG. 5F). For BC-M1 and LC-M1, a decrease in the Cyr61 expression upon glucose starvation was detected, whereas a Cyr61 induction was observed in MDA-231 and Hs578t cells. When MDA-468 was subjected to hypoxia and glucose starvation together, both Cyr61 and vimentin were induced (FIG. 5D, E).

To consider the situation in patients, where tumour cells have to escape from the immunosurveillance during the dissemination process, we monitored PD-L1 (programmed cell death 1 ligand 1) levels. PD-L1 protects tumour cells from the elimination by T-cells and was recently detected in CTC (25). Since it was noticed that PD-L1 can be induced by 0.5% of $O_2$ via HIF-1α (26), we analyzed a potential PD-L1 induction for $O_2$ concentrations relevant for the bone marrow (1% $O_2$) or by $Co^{2+}$-treatment. We observed a PD-L1 induction in BC-M1 and Hs578t under 1% $O_2$ (FIG. 5B), and in both cell lines PD-L1 is transiently induced (FIG. 5D) in response to $Co^{2+}$-treatment. Further, extraordinary high levels of PD-L1 were observed in MDA-231 BR (FIG. 5E). This shows that DTC with a phenotype like BC-M1 are able to maintain PD-L1 levels under hypoxic conditions as present in the bone marrow in vivo and confirms that our model is compatible with the situation in patients in this respect.

EXAMPLE 5—COEXPRESSION OF CYR61 WITH PD-L1 AND FREQUENT CYR61 EXPRESSION IN PANCREATIC CANCER CELL LINES

Figure 6:
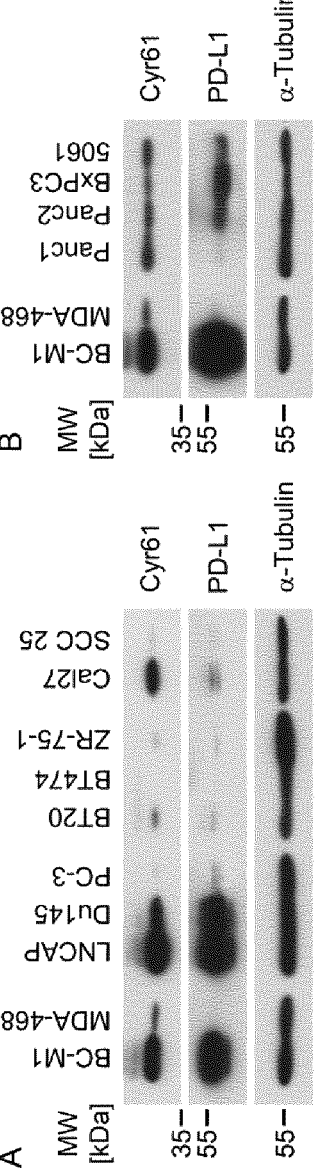

We noticed a certain coexpression of Cyr61 and PD-L1 (FIG. 5A). To substantiate this assumption we compared the Cyr61 and PD-L1 in additional cell lines of different tumour entities (FIG. 6). We found for cell lines from prostate, breast as well as from head and neck cancers a coexpression between of Cyr61 and PD-L1 (FIG. 6A). In these tumour entities, the tumour cell dissemination predominantly occurs either via haematogenous or lymphatic dissemination.

In contrast, in pancreatic cancer the metastatic spread frequently occurs via peritoneal dissemination (27). For the analyzed pancreatic cancer cell lines we observed an inverse correlation between the Cyr61 and PD-L1 levels (FIG. 6B).

In addition, pancreatic cancer is one example of tumour cell entities, that can rise from inflammation (pancreatitis) leading to the dissemination of pre-malignant cells (28). We detected in all four analyze pancreatic cancer cell lines Cyr61, suggesting frequent expression of Cyr61 pancreatic cancer.

EXAMPLE 6—CYR61 RESPONSE TO ERBB-2 EXPRESSION UNDER HYPOXIC CONDITIONS

Figure 7:
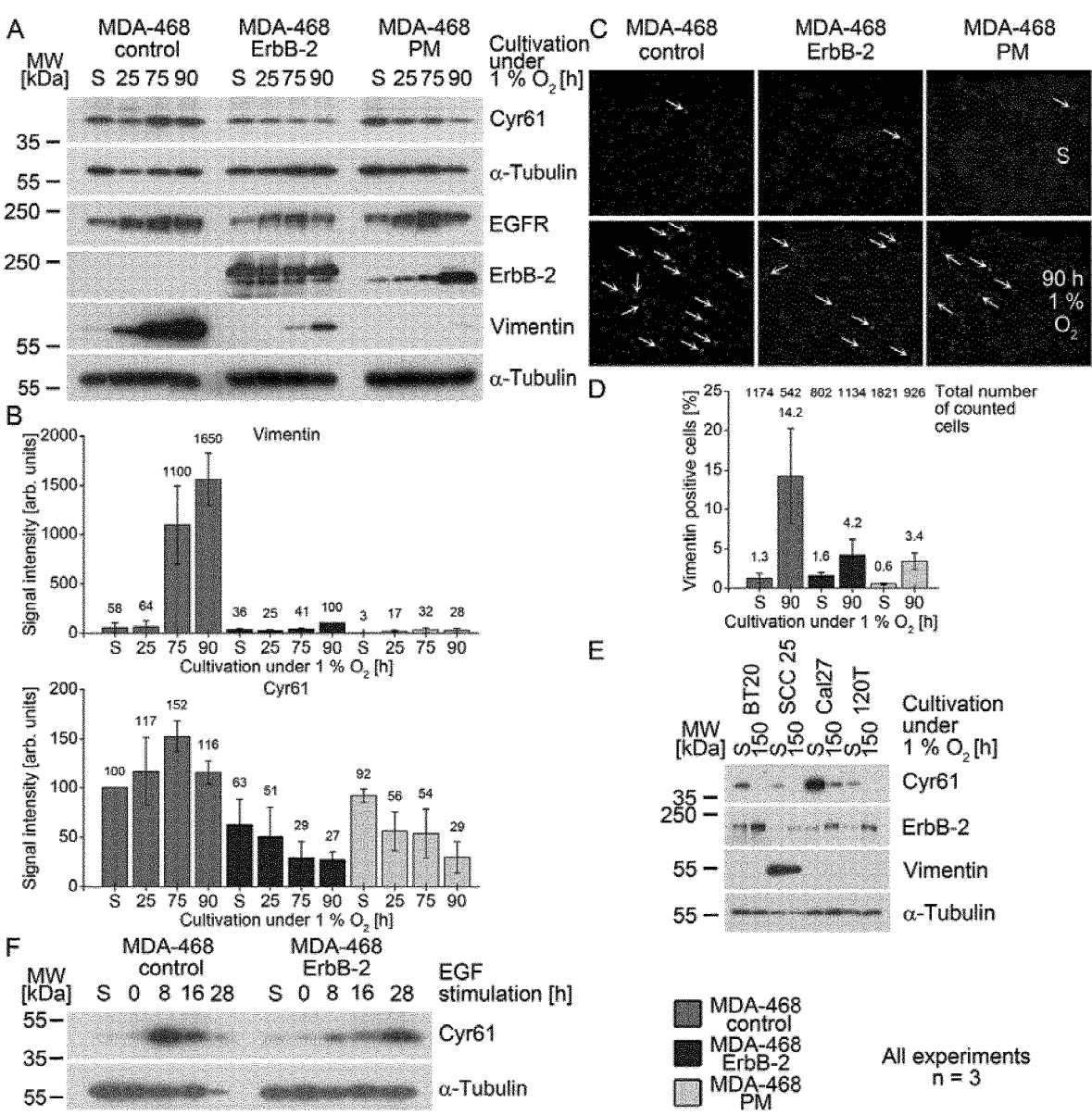

Other than triple negative breast tumours, ErbB-2 positive tumours show only a low number of individual tumour cells with mesenchymal attributes (4). We therefore assumed that ErbB-2 might affect the acquisition of mesenchymal attributes and Cyr61 levels (FIG. 7A, B). ErbB-2 was overexpressed in MDA-468 and the resulting cell line was named MDA-468 ErbB-2. MDA-468 control cells carried an expression vector without insert and MDA-468 PM expressed an ErbB-2 protein in which tyrosine 1248 was replaced by phenylalanine (12). Under standard cell culture conditions, the Cyr61 expression was reduced in MDA-468 ErbB-2 compared with MDA-468 control. After exposition to hypoxic conditions the Cyr61 expression values in MDA-ErbB-2 decreased even further. Compared with MDA-468 control, MDA-ErbB-2 and MDA-468 PM showed an attenuation of the vimentin induction under hypoxic conditions. This was confirmed on the cellular level by immunofluorescent staining for vimentin (FIG. 7C, D).

Indeed, our cell model contains a systematic error, since in MDA-468 without expression vector Cyr61 was down-regulated under hypoxia (FIG. 5B), whereas for MDA-468 control this was not observed (FIG. 7A). We therefore confirmed the Cyr61 down regulation in an independent set of cell lines (FIG. 7E). Selected were the breast cancer cell line BT20 and three squamous cell carcinoma cell lines from head and neck cancer. For all four cell lines ErbB-2 induction under hypoxia with concomitant Cyr61 downregulation was observed.

Further, EGF stimulation of MDA-468 control and MDA-468 ErbB-2 leads to massive induction of Cyr61 (FIG. 7F). These experiments were performed under standard cell culture conditions.

EXAMPLE 7—DISCOVERY OF CYR61 SECRETION IN DTC

Figure 8:
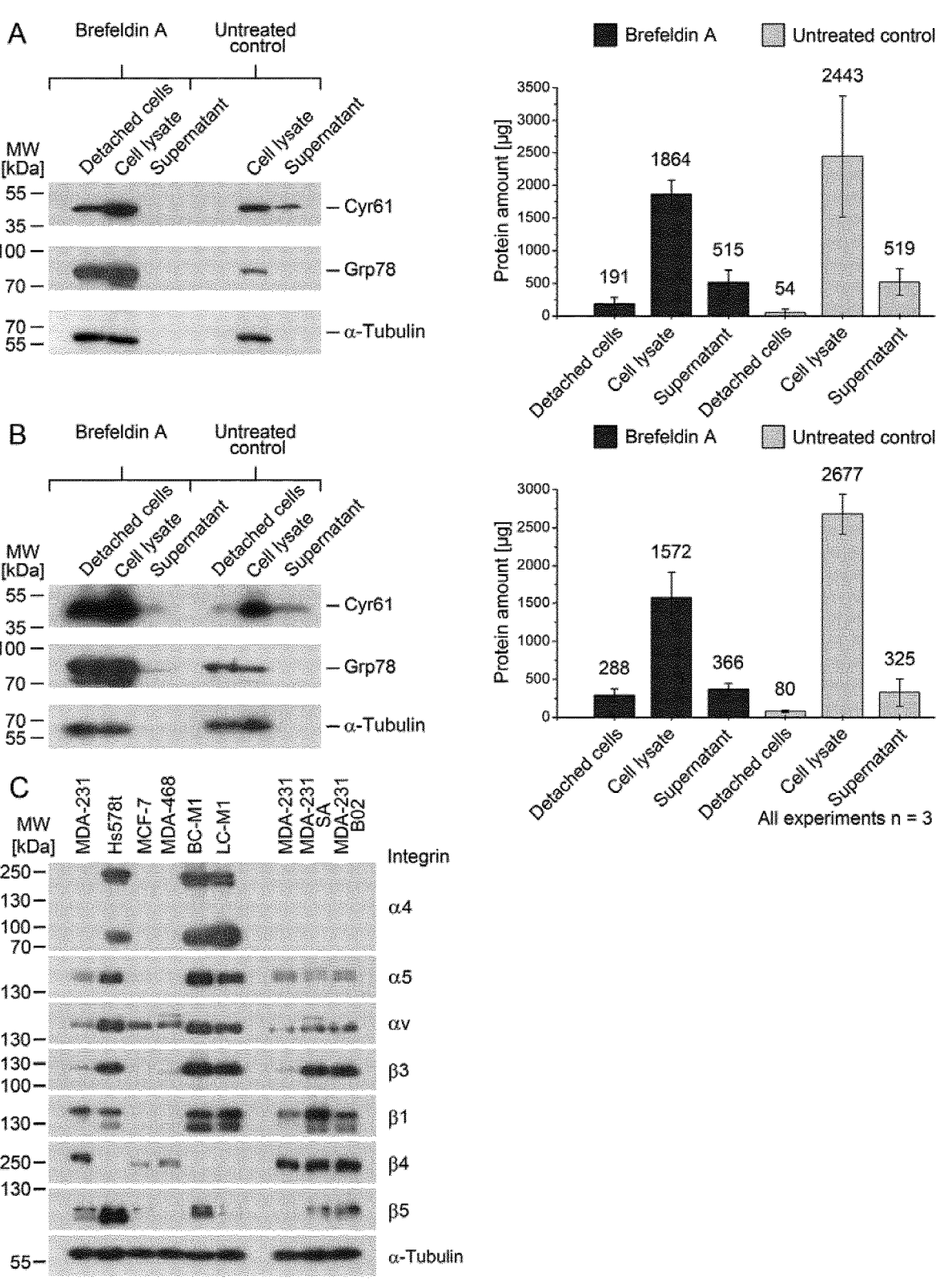

Primary tumor cells can secrete Cyr61 into the extracel-lular space. However, it is unclear if Cyr61 can be also secreted by CTC or DTC. The cell culture medium of BC-M1 DTCs was therefore analyzed for the presence of secreted Cyr61 (FIG. 8). Since it cannot be excluded that lysed cells may release Cyr61, cells were treated with Brefeldin A (BFA) in parallel. BFA inhibits the protein transport from the endoplasmic reticulum to the Golgi apparatus. To clear the cell culture medium from detached cells, the culture medium was centrifuged. The soluble fraction was designated as the supernatant, and the insoluble debris was designated as detached cells. Since BFA treat-ment leads to the activation of Grp78 (30), Grp78 induction served as a positive control.

Elevated Cyr61 levels in the untreated supernatant control compared with the corresponding BFA treated fraction was detected in MDA-231 and BC-M1 (FIG. 8A, B). Further-more, the analysis of the non-secreted cytoplasmic protein alpha-Tubulin revealed no detectable contamination of cyto-plasmic proteins into the supernatant fraction, suggesting the detection of secreted Cyr61 in the analyzed cell lines.

For the induction of a biological function of secreted Cyr61, the cells need the presence of suitable Cyr61 recep-tors. Among a variety of different Cyr61 receptors, the heterodimer of integrin αv and integrin β3 (integrin αvβ3) in one of the best investigated Cyr61 receptors (34). We therefore determined the presence of different integrins in cell lines with emphasis of the Cyr61 receptor integrin αvβ3 (FIG. 8C). With the exception of MCF-7, where integrin β3 was not detectable, all investigated cell lines have the structural prerequisites for the formation of a functional Cyr61-integrin αvβ3 complex. The DTC cell lines exhibit very high levels of integrin αv and integrin β3. In addition, the bone metastatic sublines of MDA-231, MDA-231 SA and MDA-231 B02, display elevated levels of integrin αv and integrin β3 compared with the parental cell line.

EXAMPLE 8—ESTABLISHMENT OF AN ENZYME-LINKED IMMUNOSORBENT ASSAY FOR THE DETECTION OF CYSTEINE-RICH ANGIOGENIC INDUCER 61 (CYR61 ELISA)

Figure 9:
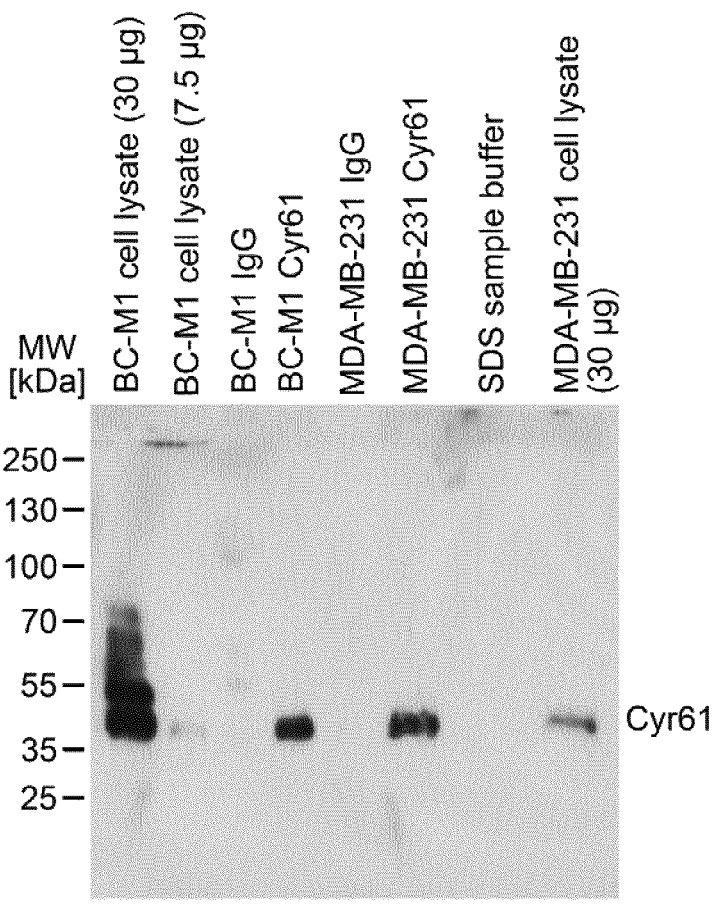

Analyses on cell lines by Western Blot. First, it was investigated if the anti-Cyr61 antibody (anti-Cyr61 antibody (H78) rabbit polyclonal, Santa Cruz Biotechnology, Santa Cruz, USA) is able to bind to Cyr61 in liquid solution. We established a Cyr61 immunoprecipitation (IP) on the cell lysates of BC-M1 and MDA-MB-231 (FIG. 9). The cell lines were cultured under standard culture conditions. The Cyr61 protein was caught using the rabbit anti-Cyr61 anti-body (H78) and detected in the Western-Blot by a mouse anti-Cyr61 antibody. These data show that Cyr61 can be isolated from liquid samples by the anti-Cyr61 antibody (H78).

Next, the quality of the anti-Cyr61 antibody (H78) was compared with an anti-Cyr61 antibody from Cell Signaling (CST) by Western Blot (FIG. 10A). Cell lysates from four different cell lines varying in their Cyr61 levels were ana-lyzed. Both antibodies detected a signal at a molecular mass of approx. 40 kDa, which was in both cases the predominant signal in the Western Blots. The H78 antibody provided clearer signals with fewer background signals compared with the CST antibody, in particular in cell lysates with low Cyr61 levels like MDA-MB-468. In the quantitative analy-ses of the Western Blots, the highest Cyr61 signals were detected for BC-M1 using the H78 antibody, whereas for the CST antibody the highest values were observed for MDA-MB-231. Since for all experiments the same cell lysates were used, it is unlikely that this effect is a result of a biological effect. Possibly, this might be due to the limits of the measurement accuracy, since the error bars for the values of MDA-MB-231 and BC-M1 overlap. Alternatively, this effect might be due to different recognition sites on Cyr61 by the two different antibodies. Since the H78 antibody pro-vided signals with less background noise, this antibody was used for the establishment of the ELISA.

The H78 antibody was further analyzed by application of human recombinant Cyr61 in a dilution series (FIG. 10B). The Western Blots showed a band at a molecular mass of approximately 40 kDa both in the cell lysates and in the samples of the recombinant Cyr61 protein. The observed molecular masses are compatible with a predicted molecular mass of processed (cleaved signal peptide) of approx. 39.5 kDa.

For the samples with recombinant Cyr61, additional sig-nals were observed at molecular mass of approx. 90 kDa. Since Cyr61 possesses five disulfide bridges, these signals might be Cyr61 dimers that could not be completely cleaved in the sample preparation.

At prolonged exposition times of the X-ray films weak unspecific signals were detected in the cell lines. Under these conditions, the specific Cyr61 signals accounts for the mayor part total signal, but unspecific signals become detectable. In particular, the cell lysate of MCF-7 provided no detectable specific Cyr61 signal and the highest unspe-cific background of the analyzed cell lines. Since this finding is crucial for the establishment of the Cyr61-ELISA, 40 µg of MCF-7 cell lysate was also applied to visualize the unspecific background in this cell line.

Figure 11:
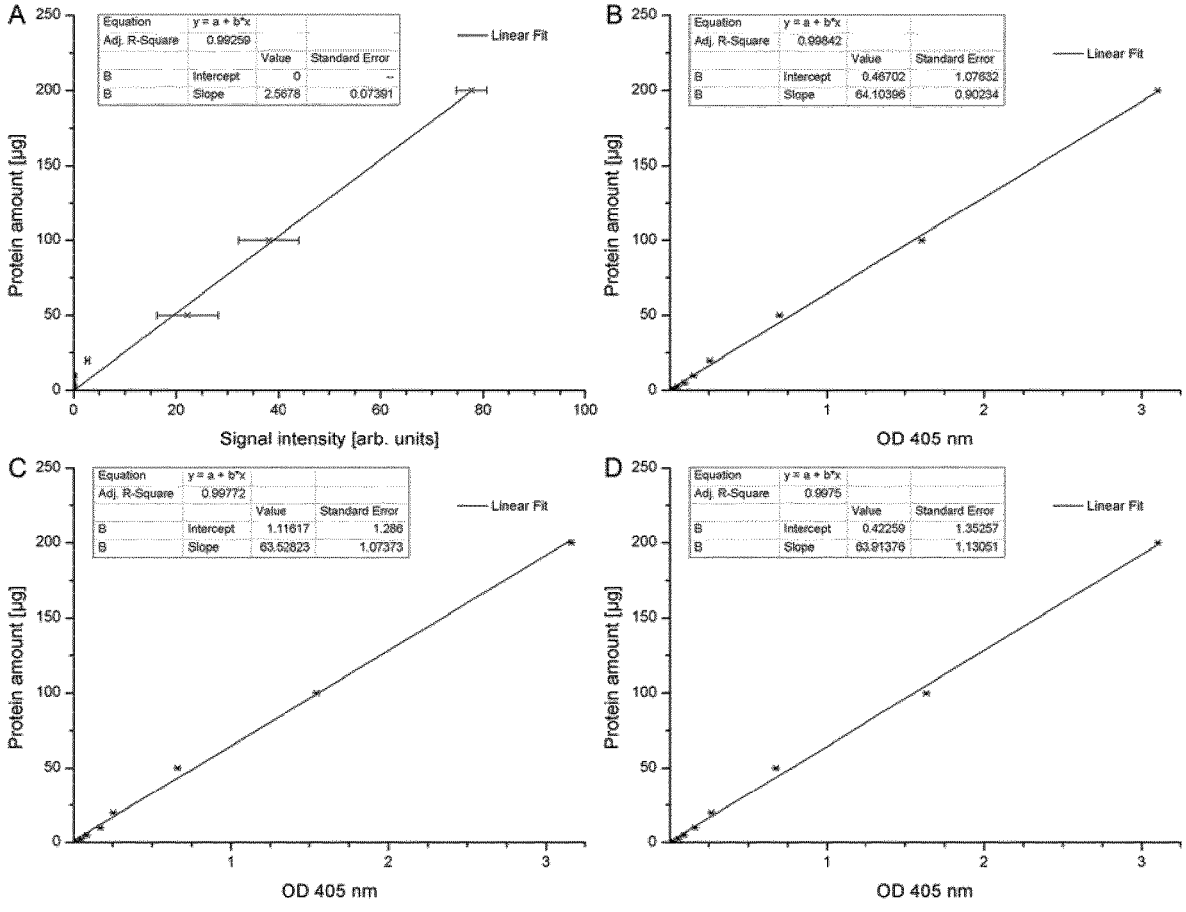

From the signal intensities of the recombinant Cyr61 dilution series (FIG. 10B) a calibration curve was derived (FIG. 11A). The signal intensities [arbitrary units] of known Cyr61 protein amounts were plotted and a calibration curve (linear fit) was derived.

The linear equation was determined as:

$$y=2.5678x \qquad \text{(equation 1)},$$

with y as the protein amount of Cyr61 [µg] and x as the signal intensity on the X-ray films.

Application of equation 1 to the determined Cyr61 signal intensities in the cell lysates of the cell lines (FIG. 10B) allowed the calculation of the Cyr61 protein amount in the cell lysates (10 µg of total protein). The calculated average values of the Cyr61 protein amount of three experiments were:

MCF-7: 0.1 ng±0.4 ng
MDA-MB-468: 6.5 ng±5.4 ng
MDA-MB-231: 23.9 ng±14.3 ng and
BC-M1: 32.8 ng±12.5 ng.

Therefore, 10 µg of BC-M1 cell lysate contain approx. 33 ng of Cyr61, which is 0.33 percent of the total protein amount.

value for 10 µg of the MCF-7 cell lysate (0.261973327) was subtracted and then equation 2 was applied to the values. The resulting values are presented in column 4 and 5:

| 10 µg MCF-7 cell lysate spiked with recombinant Cyr61 [µg] | Average value (n = 3) OD405 nm | Standard deviation of the OD405 values | Calculated Cyr61 protein amount [ng] after MCF-7 subtraction (average values) | Calculated Cyr61 protein amount [ng] after MCF-7 subtraction (standard deviation) |
|---|---|---|---|---|
| 0 | 0.238639767 | 0.007433709 | −1.03 | 0.94 |
| 1 | 0.27349667 | 0.002929 | 1.21 | 0.65 |
| 2.5 | 0.311413361 | 0.000727006 | 3.64 | 0.51 |
| 5 | 0.354000014 | 0.004590354 | 6.37 | 0.76 |
| 10 | 0.42162001 | 0.008609143 | 10.70 | 1.02 |
| 20 | 0.513366677 | 0.005907896 | 16.58 | 0.85 |
| 50 | 0.903566639 | 0.003611554 | 41.60 | 0.70 |
| 100 | 1.857266665 | 0.001929598 | 102.73 | 0.59 |
| 200 | 3.53030001 | 0.008883117 | 209.98 | 1.04 |

Unlike for the Cyr61 ELISAs (see below), the values of the Cyr61 signal intensities in MCF-7 were not subtracted as unspecific background from the Cyr61 signal intensities of the other cell lines, because the proteins of the cell lysates were separated according to their mass. This allowed the discrimination of the unspecific signals from the specific Cyr61 signals in these Experiments.

Technical analyses on cell lines by the Cyr61 ELISA. Analogous to the analyses of the cell lysates by Western Blot, Cyr61 was analyzed by ELISA. First, a calibration curve with known protein amounts of recombinant Cyr61 was generated in a dilution series (FIG. 11B).

The linear equation was determined as:

$$y=64.104x+0.467 \qquad \text{(equation 2),}$$

with y as the protein amount of Cyr61 [µg], x as the signal intensity on the X-ray films and the fixed value of 0.467 as the intercept.

It was observed in the Western Blot analyses that MCF-7 is a cell line with no detectable Cyr61 signals, but with some degree of unspecific background. To investigate this further, a series of MCF-7 cell lysates with increasing protein amounts were analyzed. The following OD405 nm values were observed:

| Applied protein amount of MCF-7 cell lysate [µg] | Average value (n = 3) OD405 nm | Standard deviation of the OD405 values |
|---|---|---|
| 0 | 0.002896656 | 0.000754309 |
| 2.5 | 0.071150015 | 0.003339141 |
| 5 | 0.151973335 | 0.003518485 |
| 10 | 0.261973327 | 0.00317575 |
| 20 | 0.454233329 | 0.006123999 |

These data show that the amount of the unspecific background is proportional to the applied protein amount of the cell lysate. Application of equation 2 to the 10 µg value of MCF-7 as an example results in a value of 17.26 ng±0.67 ng Cyr61, which can be considered as a false positive (background value) for Cyr61 in MCF-7.

To test the idea that the values from the MCF-7 samples can be subtracted from samples to be analyzed to obtain Cyr61 quantification without background noise, we spiked into samples of 10 µg MCF-7 cell lysates different amounts of recombinant Cyr61 protein and determined the OD405 value. From these values the previously determined OD405

Comparison of the obtained values (column 4) with the input values (column 1) shows that the false positive Cyr61 values are largely eliminated.

The main focus of the establishment of the Cyr61 ELISA was the analyses from the cell culture supernatants to analyze secreted Cyr61. Therefore, we analyzed the MCF-7 cell culture supernatants.

Since Cyr61 was not detectable in MCF-7 cell lysates analyzed by Western Blot, we assumed that Cyr61 is not synthesized in MCF-7 (or only at very low levels). Therefore, it is probable to assume that Cyr61 is not secreted in MCF-7 so that the supernatant can be applied for background subtraction similar to the experiments performed on the cell lysates.

Analogous to the experiments on cell lysates (FIG. 11B), for the analyses of the cell culture supernatants a calibration curve using recombinant Cyr61 was generated (FIG. 11C).

The resulting equation for the calibration curve was:

$$y=63.528x+1.1162 \qquad \text{(equation 3)}$$

with y as the protein amount of Cyr61 [µg], x as the signal intensity (OD405 nm) in the ELISA reader and the fixed value of 1.1162 as the intercept.

It was tested if the OD405 value for the cell culture supernatants of MCF-7 is proportional to the applied volume [µl] of the culture supernatant:

| Applied cell culture supernatant of MCF-7 [µl] | Average value (n = 3) OD405 nm | Standard deviation of the OD405 values |
|---|---|---|
| 0 | 0.0018903 | 0.000472051 |
| 50 | 0.016325 | 0.000990123 |
| 100 | 0.028531999 | 0.000410819 |

Similar to the results of experiments performed on the cell lines, the OD405 nm values increase with increasing amounts of the MCF-7 cell culture supernatant. Application of the 50 µl value of the MCF-7 culture supernatant to equation 3 yield a calculated (false positive) Cyr61 protein amount of 2.15 ng±1.18 ng Cyr61 in that sample.

Next, it was tested if the values from the MCF-7 samples can be subtracted from samples to be analyzed to obtain Cyr61 quantification without background noise. Therefore, we spiked into samples of 50 µl MCF-7 cell culture supernatants recombinant Cyr61 protein. From the obtained values the previously determined OD405 value for 50 µl of the MCF-7 supernatant (0.016325) was subtracted and then equation 3 was applied to the values. The resulting values are presented in column 4 and 5:

| 50 μl MCF-7 culture supernatant spiked with recombinant Cyr61 [μg] | Average value (n = 3) OD405 nm | Standard deviation of the OD405 values | Calculated Cyr61 protein amount [ng] after MCF-7 subtraction (average values) | Calculated Cyr61 protein amount [ng] after MCF-7 subtraction (standard deviation) |
|---|---|---|---|---|
| 0 | 0.015379 | 0.000195517 | −1.18 | 1.13 |
| 1 | 0.052273333 | 0.003801922 | 1.17 | 1.36 |
| 2.5 | 0.073559566 | 0.002990397 | 2.52 | 1.31 |
| 5 | 0.117190335 | 0.003245137 | 5.29 | 1.32 |
| 10 | 0.183230014 | 0.005838419 | 9.49 | 1.49 |
| 20 | 0.269056667 | 0.003035627 | 14.94 | 1.31 |
| 50 | 0.782196652 | 0.003402488 | 47.54 | 1.33 |
| 100 | 1.620499986 | 0.005436908 | 100.79 | 1.46 |
| 200 | 3.16052621 | 0.000862133 | 198.63 | 1.17 |

Comparison of the obtained values (column 4) with the input values (column 1) shows that the false positive Cyr61 values are largely eliminated.

Since these results suggest that the Cyr61 levels can be accurately determined in cell culture samples, this procedure was applied to new sets of cell line samples. Again, a calibration curve using recombinant Cyr61 was generated (FIG. 11D). The corresponding equation for the calibration curve was:

$$y=63.914x+0.4226 \qquad \text{(equation 4)}$$

wherein y is the protein amount of Cyr61 [μg], x as the signal intensity (OD405 nm) in the ELISA reader and the fixed value of 0.4226 as the intercept.

Next, 50 μl of cell culture supernatant from the cell lines MCF-7, MDA-MB-468, MDA-MB-231 and BC-M1 were analyzed (column 1 below). The value for the supernatants of MCF-7 was subtracted from values of the other cell lines and equation 4 was applied to the resulting values. The protein amount of Cyr61 [ng] is shown in column 4:

| Cell line whose 50 μl of culture supernatant was analyzed | Average value (n = 3) OD405 nm | Standard deviation of the OD405 values | Calculated Cyr61 protein amount [ng] after MCF-7 subtraction (average values) | Calculated Cyr61 protein amount [ng] after MCF-7 subtraction (standard deviation) |
|---|---|---|---|---|
| MCF-7 | 0.018244 | 0.00081034 | — | — |
| MDA-MB-468 | 0.154306665 | 0.0030896 | 9.12 | 0.57 |
| MDA-MB-231 | 0.547366622 | 0.00508453 | 34.24 | 0.70 |
| BC-M1 | 0.705300052 | 0.00939629 | 44.34 | 0.97 |

Therefore, 50 μl of cell culture supernatant of BC-M1 contained 44.3 ng±1.0 ng of Cyr61. The quality of these values were assessed by spiking of 50 ng of recombinant Cyr61 to 50 μl of the individual cell culture supernatants and analyzed again. In this case, the value of MCF-7 was processed, because 50 ng of Cyr61 was spiked to the samples. Therefore, like for the other cell lines, from the measured value of MCF-7 the previous value of the cell culture supernatant (0.018244) was subtracted. This was followed by application of the equation 4 to the values from all 4 cell lines. The expected values are the sum of the previously calculated values for Cyr61 and the spiked 50 ng of spiked recombinant Cyr61. Example BC-M1: 44.3 ng+50 ng=94.3 ng:

| Cell line whose 50 μl of culture supernatant was spiked with 50 ng of recombinant Cyr61 | Average value (n = 3) OD405 nm | Standard deviation of the OD405 values | Calculated Cyr61 protein amount [ng] after MCF-7 subtraction (average values) | Calculated Cyr61 protein amount [ng] after MCF-7 subtraction (standard deviation) | Expected Cyr61 protein value [ng] |
|---|---|---|---|---|---|
| MCF-7 | 0.714863333 | 0.00455625 | 44.95 | 0.66 | 50 |
| MDA-MB-468 | 0.836704498 | 0.00571979 | 52.73 | 0.74 | 59.1 |
| MDA-MB-231 | 1.283070001 | 0.00246919 | 81.26 | 0.53 | 84.2 |
| BC-M1 | 1.573926803 | 0.0069443 | 99.85 | 0.81 | 94.3 |

Corresponding experiments were performed with the cell lysates of the samples. Five µg of protein of the cell lysates were applied. The value of MCF-7 was subtracted from the values of the other cell lines and the resulting values were processed by using equation 4:

| 5 µg of whole cell extract analyzed from | Average value (n = 3) OD405 nm | Standard deviation of the OD405 values | Calculated Cyr61 protein amount [ng] after MCF-7 subtraction (average values) | Calculated Cyr61 protein amount [ng] after MCF-7 subtraction (standard deviation) |
|---|---|---|---|---|
| MCF-7 | 0.094796667 | 0.0026035 | — | — |
| MDA-MB-468 | 0.263613331 | 0.00594331 | 11.21 | 0.64 |
| MDA-MB-231 | 0.845366674 | 0.00507125 | 48.39 | 0.58 |
| BC-M1 | 1.06184969 | 0.00588954 | 62.23 | 0.63 |

Therefore, 5 µg of BC-M1 whole cell lysate contain 62.2 ng±0.6 ng Cyr61.

Similar to the cell culture supernatants, a quality assessment was performed by spiking of 50 ng of recombinant Cyr61 to the samples. From the samples, the previous value of MCF-7 (0.094796667) was subtracted and the protein amount [ng] was calculated by equation 4:

| 5 µg of whole cell extract spiked with 50 ng of recombinant Cyr61 analyzed from | Average value (n = 3) OD405 nm | Standard deviation of the OD405 values | Calculated Cyr61 protein amount [ng] after MCF-7 subtraction (average values) | Calculated Cyr61 protein amount [ng] after MCF-7 subtraction (standard deviation) | Expected Cyr61 protein value [ng] |
|---|---|---|---|---|---|
| MCF-7 | 0.79160334 | 0.00588954 | 44.96 | 0.63 | 50 |
| MDA-MB-468 | 1.0157129 | 0.00220473 | 59.28 | 0.40 | 61.2 |
| MDA-MB-231 | 1.583993323 | 0.00542196 | 95.60 | 0.60 | 98.4 |
| BC-M1 | 1.817249991 | 0.00690779 | 110.51 | 0.70 | 112.2 |

Even though the calculated amount of Cyr61 in these samples in MCF-7 is lower than expected (45 ng detected vs. 50 ng expected), the expected values for the three other samples suit well to the observed values (e.g. 110.5 ng calculated vs. 112. ng expected for BC-M1). This supports the idea that the Cyr61 ELISA is a suitable tool for the quantitative analyses of Cyr61 levels in whole cell lysates and cell culture supernatants.

Since the protein amount of Cyr61 can be determined in terms of ng in the samples, it is possible to calculate the amount of Cyr61 molecules in the sample. The calculation is presented on the sample of the BC-M1 supernatant which provided a value of 44 ng Cyr61. The calculation is made for the processed Cyr61 with the cleaved signal peptide:

Given: m (Cyr61)=44 ng and M (Cyr61)=39438.4 g/mol
Searched: n (amount of substance [mol]).
The equation is: $m = n \times M$
Transforming yields: $n = m/M$
Insertion of the values: $n = 44$ ng$\times 39438.4$ g/mol
yields: $n = 1.12 \times 10^{-12}$ mol.
Multiplication of the amount of substance with the Avogadro constant yields the number of the Cyr61 molecules in the sample:
Number of molecules$= 1.12 \times 10^{-12}$ mol$\times 6.022 \times 10^{23}$
Number of molecules$= 6.77 \times 10^{11}$
Therefore, 50 µl of the BC-M1 supernatant contained $6.77 \times 10^{11}$ molecules of Cyr61 in this sample.

Analogous processes of calculation provide the following values for the other cell culture supernatants (for a volume of 50 µl of cell culture supernatant):

BC-M1 cell culture supernatant: $6.77 \times 10^{11} \pm 1.48 \times 10^{10}$ molecules, MDA-MB-231 cell culture supernatant: $5.23 \times 10^{11} \pm 1.06 \times 10^{10}$ molecules, MDA-MB-468 cell culture supernatant: $1.39 \times 10^{11} \pm 8.68 \times 10^{9}$ molecules.

The calculation of the cell lysates provides the following amounts of Cyr61 molecules in 5 µg of cell lysate:
BC-M1 cell lysate: $9.50 \times 10^{11} \pm 9.66 \times 10^{9}$ molecules,
MDA-MB-231 cell lysate: $7.39 \times 10^{11} \pm 8.86 \times 10^{9}$ molecules,
MDA-MB-468 cell lysate: $1.71 \times 10^{11} \pm 9.71 \times 10^{9}$ molecules.

These analyses refer only to technical issues in the establishment of the Cyr61. Analyses of the secreted Cyr61 in the cell culture supernatant that allow biomedical conclusions are described in the following section.

Comparison of the Western Blot results with the results obtained by the ELISA showed that both approaches provided comparable values. Differences between both approaches are mostly due to the lower sensitivity of the Western Blot approach compared with the ELISA, which can be seen on the calibration curves with recombinant Cyr61. Consequently, the dynamic range of the ELISA approach is much larger than for the Western Blot analyses. In addition, the error bars for the ELISA measurements were by far smaller than for the Western Blot analyses. From that point, the ELISA is by far superior to the Western Blot approach in terms of sensitivity, dynamic range and accuracy.

In contrast, the inherent advantage of the Western Blot approach is the ability to discriminate between specific Cyr61 signals and unspecific background signals due to protein separation in the SDS PAGE. The ELISA approach does not contain a similar fractionation step so that it is more difficult to discriminate between true Cyr61 signals and unspecific background. This issue could be handled by the application of the highly specific anti-Cyr61 (H78) antibody and by introduction of a background noise reduction step. Therefore it has to be kept in mind that the Cyr61 values for MCF-7 are zero by definition, even though that after massive over exposition of the X-ray films after Western Blot very faint signals in the MCF-7 cell lysate were detected. However, these signals could also be unspecific binding. In addition, this way of background subtraction does only include proteins that are present in the proteome of MCF-7. Other proteins, for example proteins that might cause unspecific signals in MDA-MB-468, but lack in MCF-7 are not considered in this approach. Nevertheless, this approach provides reliable values in the ELISA. The analyses support the idea that at very low Cyr61 values, the calculated values are slightly lower than they really are. Insofar, our assay has to a certain extent the tendency to generate false negative results than false positive ones.

Biological analyses on cell lines by the Cyr61 ELISA. Measurements of Cyr61 values in cell lines by Western Blot refer to the applied protein amount on the SDS PAGE. Since this approach is not applicable to secreted proteins, an alternative standardized reference system for secreted Cyr61 was established. This system includes the cell number and the cultivation time so that the Cyr61 secretion rate can be determined as the Cyr61 secretion rate in number of Cyr61 molecules per cell and day.

Figure 12:
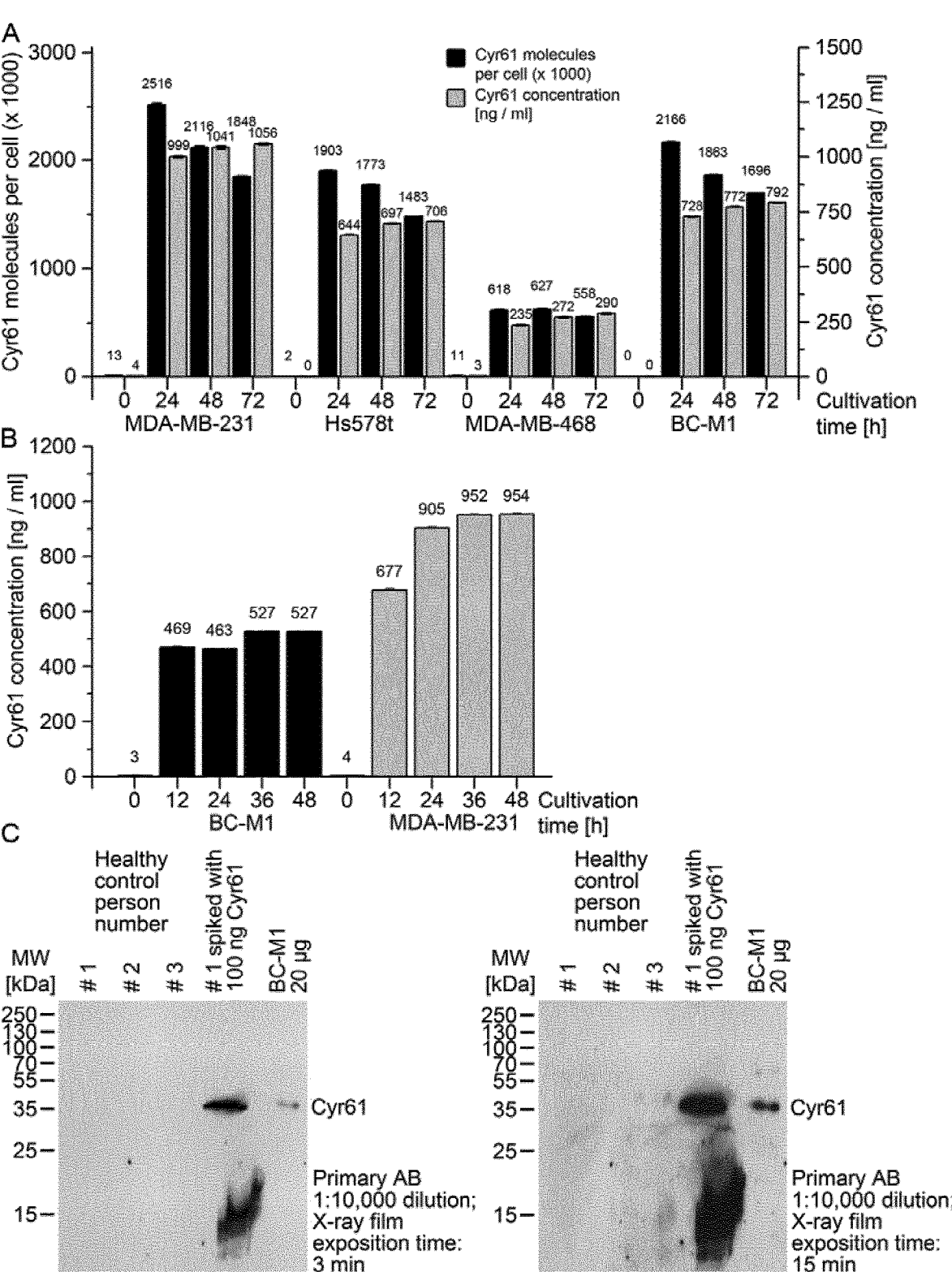

Therefore, a defined cell number was seeded. For defined cultivation times the cell culture supernatant was harvested and the cell number was determined for each time point. For the calculation of the number of Cyr61 molecules in the samples, a standard of recombinant and purified Cyr61 was analyzed. The calculation of the number of the Cyr61 molecules was performed as described above. The results of these analyses are shown in FIG. 12A. The number of the Cyr61 molecules per cell takes the cell numbers for each measurement point into account, whereas the Cyr61 concentration is calculated irrespective of the cell number. For the time point t=0 fresh medium was added to the cells.

The cells quickly secreted Cyr61 into the medium (0 h vs. 24 h). After that, the Cyr61 concentration is remarkably constant over time and appears to be specific for the individual cell line.

Due to the unexpected rapid secretion of Cyr61, the experiment was repeated for BC-M1 and MDA-MB-231 with modifications (FIG. 12B). In that case, after every 12 h the cell culture medium was replaced by fresh medium and the harvested medium was analyzed for Cyr61. These data show that BC-M1 and MDA-MB-231 are able to secret more Cyr61 in 48 h than observed in FIG. 12A under that conditions (e.g. BC-M1 0 h vs. 48 h: 772 ng/ml in FIG. 12A and 469+463+527+527 ng=1983 ng/ml in FIG. 12B for 0 vs. 48 h). Notably, the Cyr61 secretion rate increased in MDA-MB-231 after repeated medium withdrawal over time (FIG. 12B). As a result, the cells secreted within 12 h almost the Cyr61 amount detected in FIG. 12A for 24 h (FIG. 12A: 0 h vs. 24 h 999 ng/ml and FIG. 12B: 48 h 954 ng/ml).

These data suggest that the local Cyr61 concentration is rather dependent on the individual cell line than on the number of the cells. This precise maintenance of the Cyr61 concentration might imply a Cyr61 measurement and control apparatus in the cells. Possibly, even small tumour cell colonies generate a local Cyr61 enriched microenvironment surrounding the cells. It has to be kept in mind that these Cyr61 values probably reflect a steady state with constant novel synthesis and degradation of Cyr61 molecules.

EXAMPLE 9—IMPROVEMENT OF THE ENZYME-LINKED IMMUNOSORBENT ASSAY FOR THE DETECTION OF CYSTEINE-RICH ANGIOGENIC INDUCER 61 (CYR61 ELISA)

Cell Lines

For the improvement of the above ELISA for the detection of cysteine-rich angiogenic inducer 61 (Cyr61), two anti-Cyr61 antibodies were applied. One antibody was the rabbit polyclonal anti-Cyr61 antibody H78 which was raised against the amino acids 163-240 of human Cyr61. The other antibody was the mouse monoclonal anti-Cyr61 antibody H2 which was raised against the amino acids 345-381 of human Cyr61. Both antibodies were from Santa Cruz Biotechnology, Santa Cruz, USA.

Figure 13:
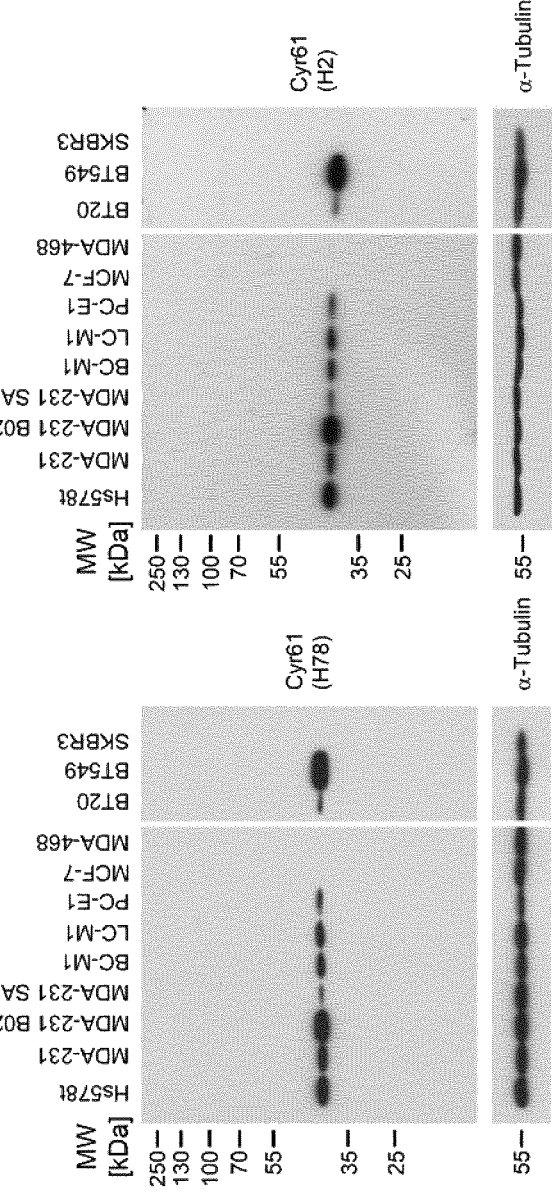

First, the Cyr61-recognition profiles of the H78 and the H2 antibodies were investigated in a set of cell lines by Western-Blot (FIG. 13). Both antibodies showed only one single band at approx. 40 kDa. In addition, the distributions of the Cyr61 signal intensities in the cell lines were similar for both antibodies.

Figure 14:
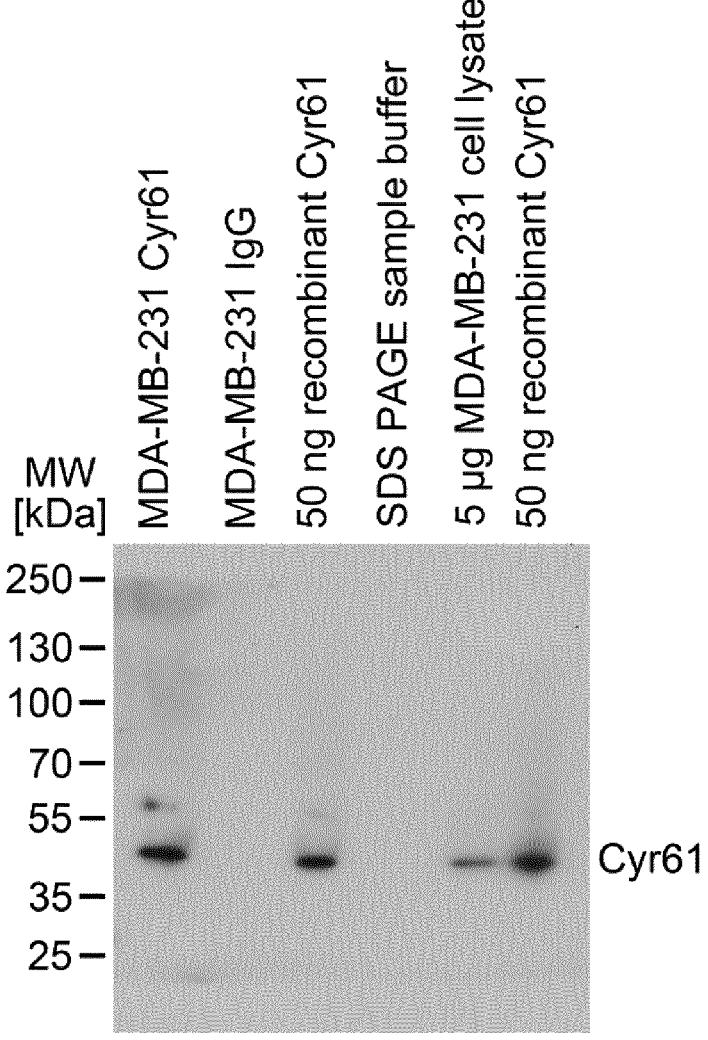

Next, it was investigated if the anti-Cyr61 antibody (H78) is able to bind to its target Cyr61 in liquid solution. Therefore, we established a Cyr61 immunoprecipitation (IP) on cell culture supernatant of MDA-MB-231 (FIG. 14). The cell line was cultured under standard culture conditions. The Cyr61 protein was caught using the mouse anti-Cyr61 antibody (H2) and detected in the Western-Blot by the rabbit anti-Cyr61 antibody (H78). For the IP of Cyr61, 200 µl of MDA-MB-231 cell culture supernatant with a Cyr61 concentration of 1.05 ng/ml, thus a total amount of 210 ng Cyr61 was applied. Twenty percent of the immunoprecipitate was applied for the Western Blot. The signal intensity for the immunoprecipitated Cyr61 was comparable with the signal intensity of 50 ng of recombinant Cyr61, suggesting that the yield of the isolated Cyr61 from the culture supernatant is close to 100 percent.

Figure 15:
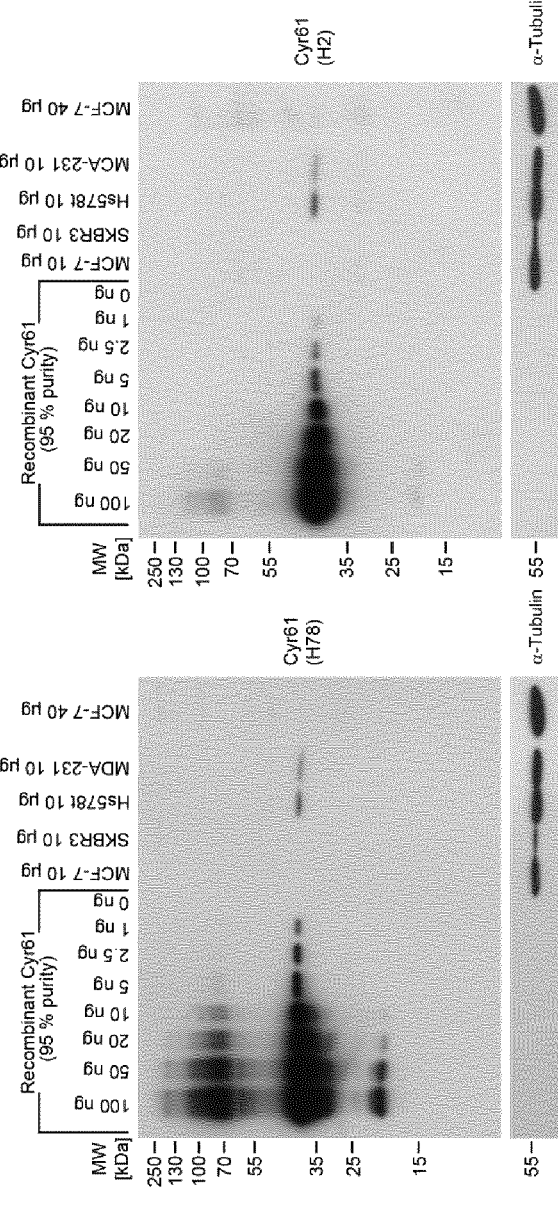

For the establishment of the Cyr61 ELISA the H78 and H2 antibodies were analyzed. Both antibodies were investigated by application of human recombinant Cyr61 protein in a dilution series and cell lysates (FIG. 15).

The Western Blots showed one single band at a molecular mass of approximately 40 kDa in the cell lysates for both antibodies. The observed molecular masses are compatible with a predicted molecular mass of processed (cleaved signal peptide) of approx. 39.5 kDa. For the recombinant Cyr61 samples, additional signals were observed at molecular mass of approx. 80 kDa. Since Cyr61 contains five disulfide bridges, these signals might be Cyr61 dimers linked by disulfide bridges that could not be completely cleaved in the sample preparation.

Comparison of the signal intensities obtained for the recombinant Cyr61 with those in MDA-MB-231 and Hs578t cell lysates allows an estimation of the Cyr61 amounts in the cell lysates. In case of the H78 antibody, the signal intensities in MDA-MB-231 and Hs578t approximately correspond to 1 ng Cyr61. Since 10 µg of cell lysates were analyzed, one microgram of MDA-MB-231 or Hs578t cell lysate would contain 100 pg Cyr61 as detected by the H78 antibody. Similarly, by application of the H2 antibody, the cell lysates would contain approximately 2.5 ng Cyr61 per 10 µg or 250 pg per 1 µg cell lysate.

Since the Western Blots analyses suggested that the anti-Cyr61 antibodies H78 and H2 might be suitable for application in an ELISA, these antibodies were further assessed. Western Blot analysis displayed high levels of Cyr61 in MDA-MB-231 (MDA-231) and Hs578t and no detectable signals in MCF-7 and SKBR3. These cell lines were therefore selected as positive or negative controls for the establishment of the Cyr61-ELISA.

Figure 16:
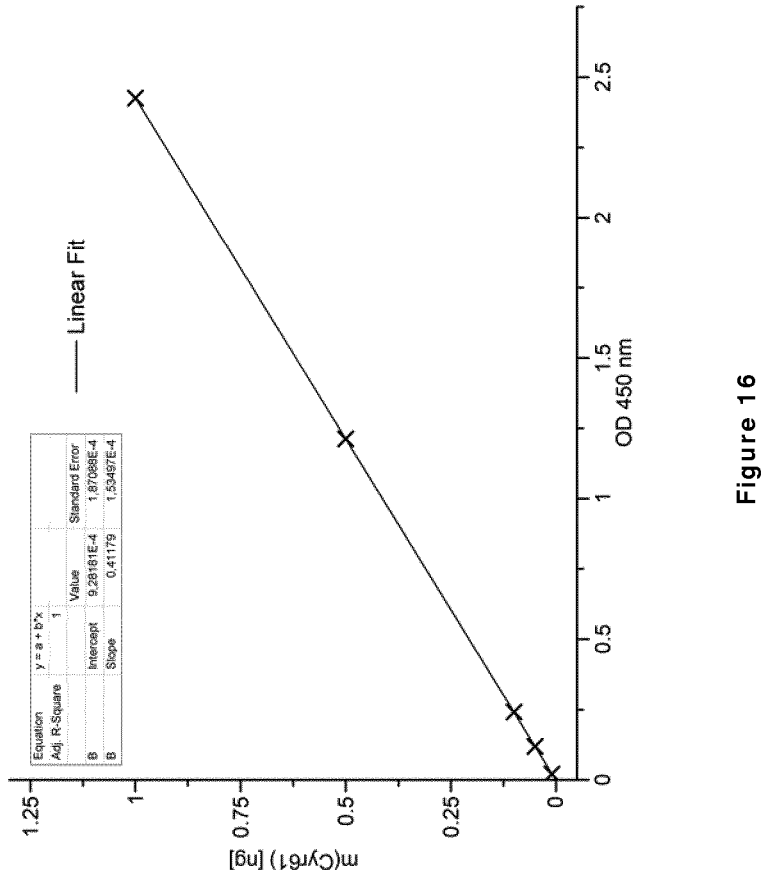

For ELISA analysis of the cell lines, a calibration curve with known protein amounts of recombinant Cyr61 was generated in a dilution series (FIG. 16)

Figure 17:
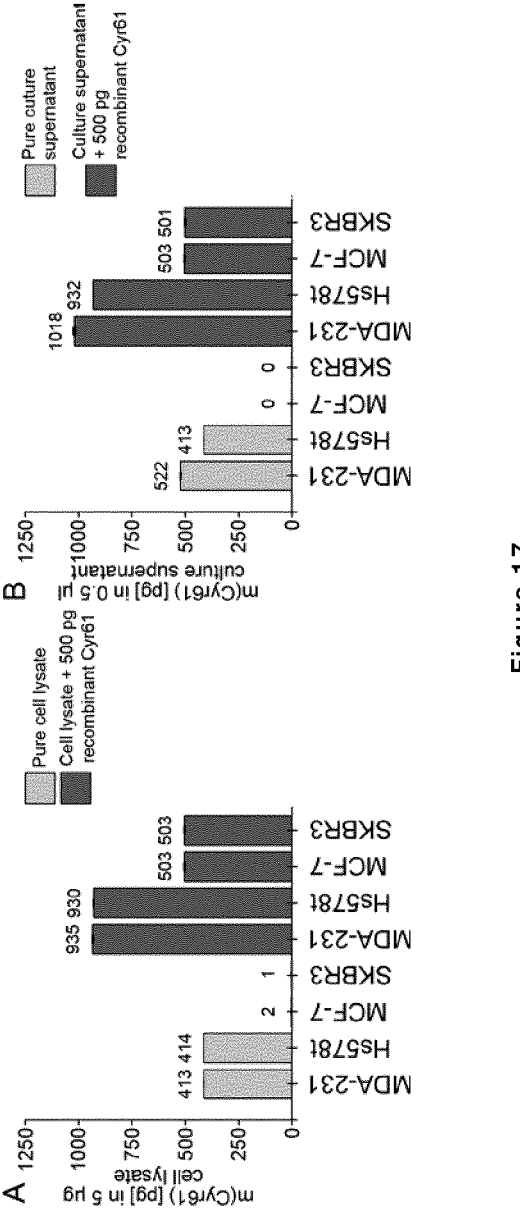

The linear equation was determined as: $y=0.4118x+0.0009$ (equation 1), with y as the protein amount of Cyr61 [ng], x as the OD (optical density) at 450 nm and the fixed value of 0.0009 as the intercept. Equation 1 was used for the determination of the Cyr61 amounts in cell lysates and cell culture supernatants of a set of test samples (FIG. 17). In 5 μg of MDA-231 cell lysate 413 pg and in cell lysate of Hs578t 414 ng of Cyr61 were detected, whereas for MCF-7 and SKBR3 no signals were observed (FIG. 17A). To confirm that these are specific Cyr61 signals, 500 ng of recombinant Cyr61 was spiked into the samples. After that, the value for MDA-231 increased to 935 pg and for Hs578t a value of 930 pg was detected. In case of MCF-7 and SKBR3, 503 pg of Cyr61 were detected in the respective cell lysates after spiking of 500 pg of recombinant Cyr61 to the samples. Since Cyr61 can be secreted to the extracellular space, it might be possible that other secreted proteins might affect the specificity of the ELISA. To test if the ELISA specifically discriminates Cyr61 from other secreted proteins, cell culture supernatants were analyzed (FIG. 17B). Cell lines that were positive for cytoplasmic Cyr61 were also positive for Cyr61 in the cell culture supernatants (MDA-231, Hs578t), whereas the cell lines that were negative for Cyr61 in the cytoplasm (MCF-7, SKBR3) were also negative for Cyr61 in the cell culture supernatants. Spiking of 500 pg recombinant Cyr61 into cell culture supernatants of these cell lines increased the detected Cyr61 values by approx. 500 ng for each cell line.

Further, the detected Cyr61 amounts by ELISA could be compared with those detected by Western Blot. In MDA-231 and Hs578t approximately 100 pg/μg Cyr61 were detected using the H78 antibody, and using the H2 antibody, the Cyr61 amounts were 250 pg/μg Cyr61 by Western Blot. The ELISA provided values of approximately 83 pg/μg Cyr61 for MDA-231 and Hs578t.

Figure 18:
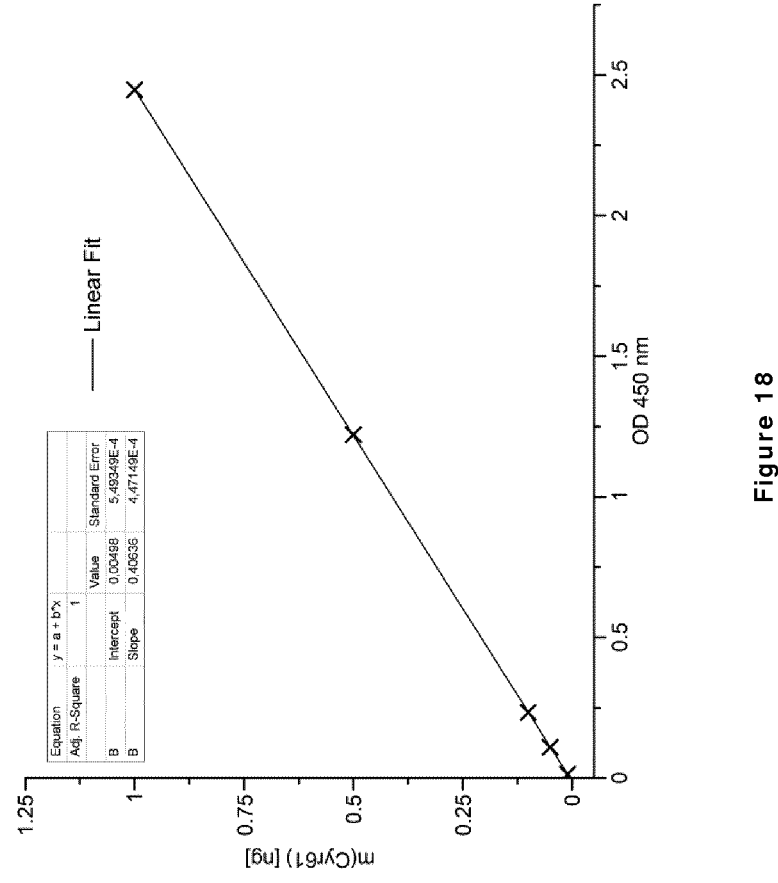
Figure 19:
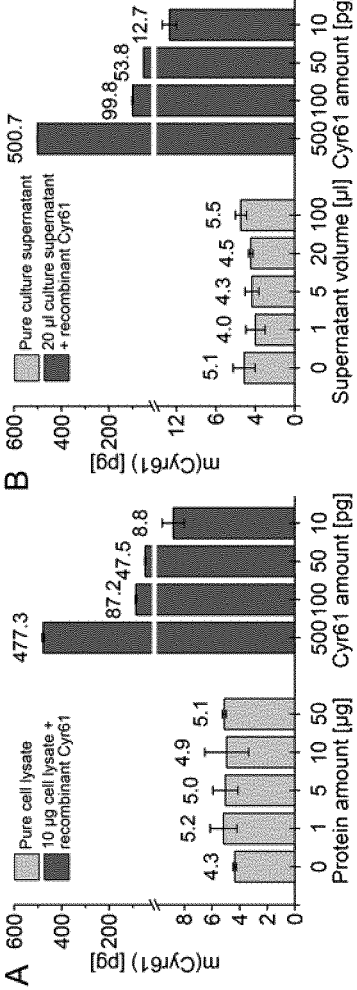

To identify potential unspecific signals in the ELISA, the cell lysate and the culture supernatant of the Cyr61 negative cell line MCF-7 was further analyzed. The equation for the calibration curve was:
$y=0.40636x+0.00498$ (equation 2), with y as the protein amount of Cyr61 [ng], x as the OD at 450 nm and the fixed value of 0.00498 as the intercept (FIG. 18). Equation 2 was used for the determination of the Cyr61 amounts in cell lysates and cell culture supernatants of a set of test samples of MCF-7 (FIG. 19).

False positive signals in the ELISA due to unspecific protein binding will be detectable as signals intensities that are proportional to the applied protein amount in MCF-7 (FIG. 19A). In fact, similar values were detected which were independent from the applied protein amount. Spiking different amounts of recombinant Cyr61 into 10 μg of MCF-7 cell lysate provided slightly lower Cyr61 values than expected. This suggests that this assay has a tendency to under represent Cyr61 values and that the background values in MCF-7 cell lysates do not originate from unspecific binding. Corresponding experiments were performed for the cell culture supernatant (FIG. 19B). Increasing volumes of MCF-7 cell culture supernatants showed constant low values that may be assigned as background noise. Spiking of different amounts of recombinant Cyr61 into 20 μl of cell culture supernatant accurately reflect the Cyr61 amounts within the limits of accuracy.

Figure 20:
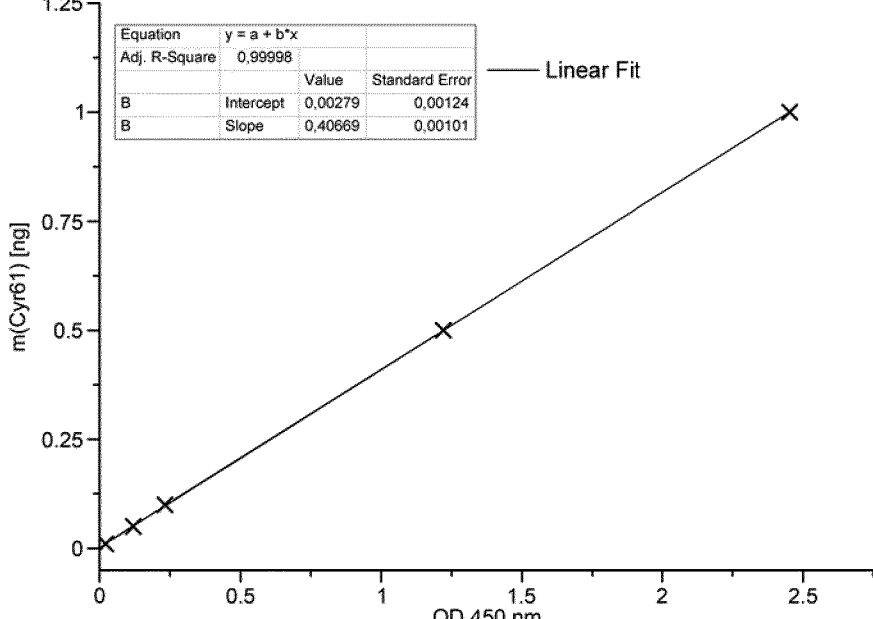

Samples of MDA-231 were analyzed in a similar fashion as those of MCF-7. The calibration curve for MDA-231 samples is shown in FIG. 20 and the calibration curve had the form:
$y=0.40669x+0.00279$ (equation 3) with y as the protein amount of Cyr61 [ng], x as the signal intensity in the ELISA reader at 450 nm and the fixed value of 0.00279 as the intercept.

Figure 21:
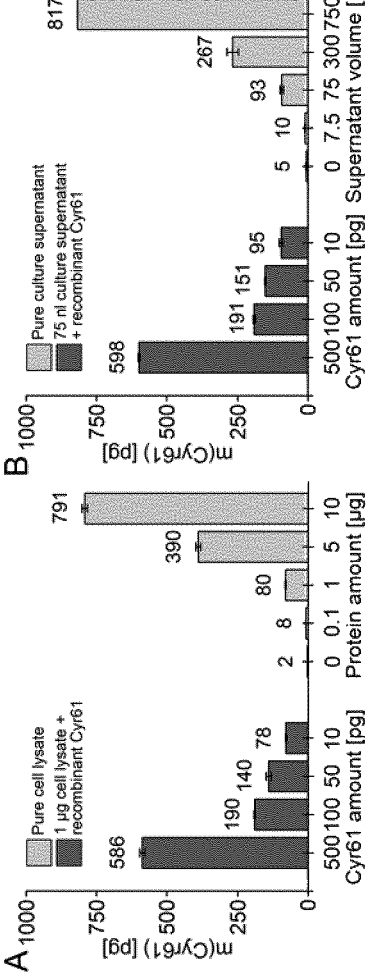

The analyses for the MDA-231 cell lysates are shown in FIG. 21A and for the culture supernatants are shown in FIG. 21B. One microgram MDA-231 cell lysate contained 80 pg Cyr61 in these measurements (FIG. 21A), which may serve as a reference value for the spiking experiments with recombinant Cyr61. For example, after spiking of 50 pg recombinant Cyr61 into 1 μg MDA-231 cell lysate 140 pg Cyr61 were detected in the sample, which is 10 pg more than expected. In case of the cell culture supernatants (FIG. 21), for 75 nl of MDA-231 cell culture supernatant 93 pg Cyr61 were detected. Spiking of 75 nl supernatant with 50 pg recombinant Cyr61 provided a value of 151 pg Cyr61, which was 8 pg Cyr61 more than expected.

Potentially, for cell culture supernatants, the ELISA provided slightly higher values than expected when the Cyr61 amount is low. This could be seen in the dilution series of MDA-231 culture supernatant, where an increase of the sample volume by factor 10 led to less than an increase by factor 10 of the calculated Cyr61 amount.

Patient Samples

Figure 22:
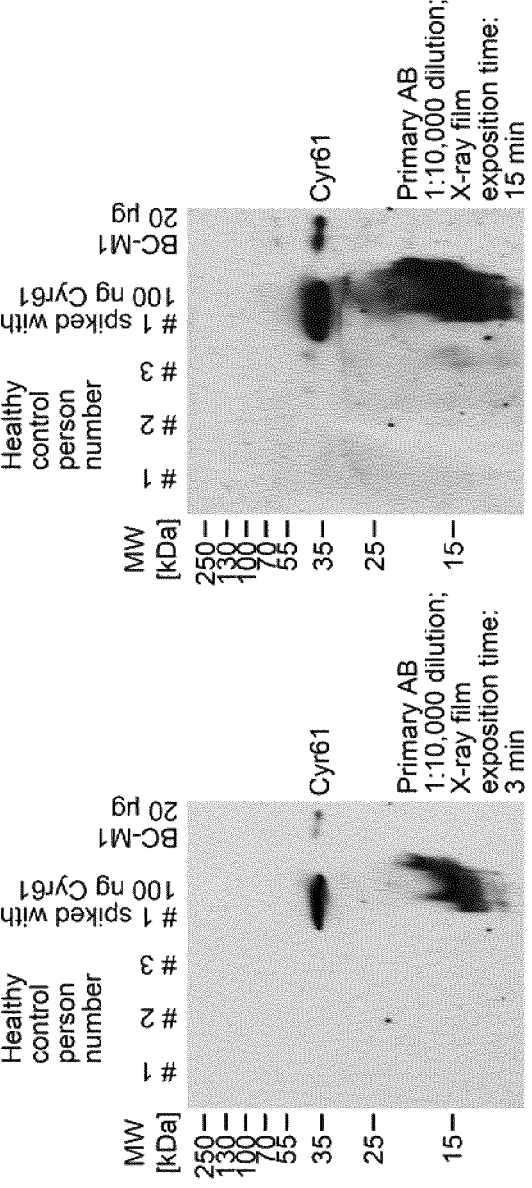

Since plasma samples may contain other proteins than cell culture samples, we investigated if the established Cyr61-ELISA can be applied to the analysis of patient samples. First, the Cyr61 status in the plasma of healthy control individuals was tested by Western Blot using the H78 antibody (FIG. 22). This may provide information of unspecific binding of the anti-Cyr61 antibody to other proteins. Since the application of 100 μl of blood plasma resulted in massive distortion of the SDS-gel bands (not shown), we applied a protein purification step. To confirm that Cyr61 is recovered in this purification step, 100 ng of recombinant Cyr61 was spiked to one aliquot of the patient samples.

Only in the sample of donor #3 weak unspecific signals with a mass of approx. 40 kDa were detected. The other sections of the X-ray film did not show unspecific signals, suggesting that blood plasma of healthy persons shows only very low levels of soluble Cyr61 and that the anti-Cyr61 antibody specifically detects Cyr61 in blood serum.

Figure 23:
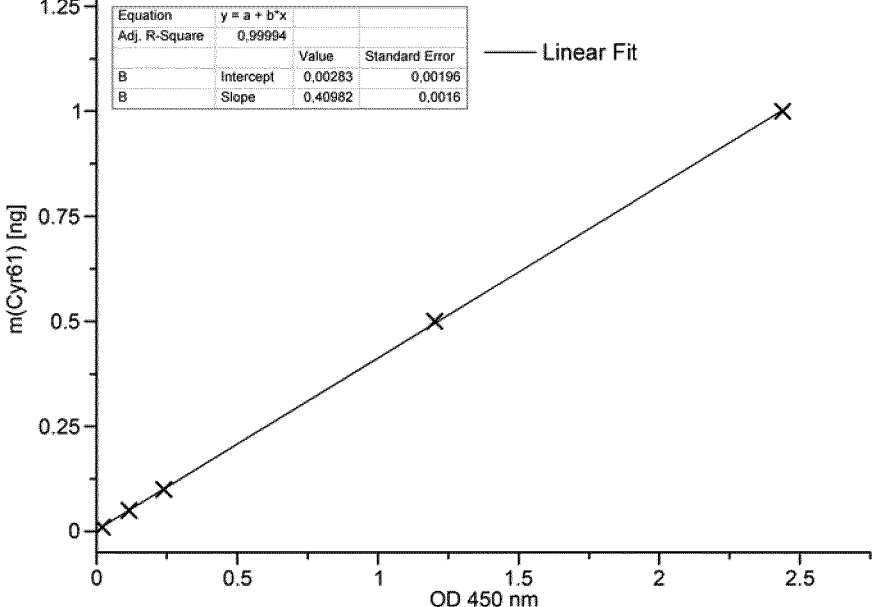

Next, the Cyr61 ELISA was applied to the analysis of plasma samples from healthy donors. The calibration curve is shown in FIG. 23 and had the form: as $y=0.40982x+0.00283$ (equation 4) with y as the protein amount of Cyr61 [ng], x as the signal intensity in the ELISA reader at 450 nm and the fixed value of 0.00283 as the intercept.

Figure 24:
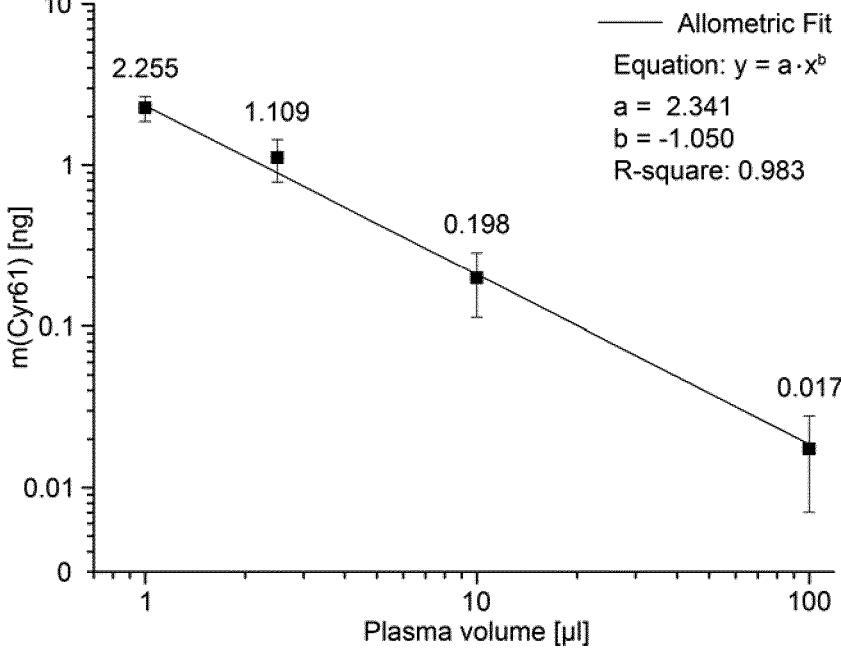

The analyses on plasma samples of female healthy individuals over the age of 50 years are shown in FIG. 24. These analyses showed that the Cyr61 values in plasma are low compared with the culture supernatant of MDA-231. In addition, the calculated Cyr61 amounts in the samples decreased with increased plasma amounts. One reason for this effect is a small remaining OD value after background subtraction, since the background subtraction is not perfect in all cases. Since this remaining small value is also multiplied during the conversion to nanogram per millilitre, this remaining value increases with decreasing sample volume.

For the analysis of plasma samples of breast cancer patients as well as of healthy control persons 2.5 µl of plasma were analyzed (FIG. 24). These analyses suggest the presence of a background value of 1.1 ng/ml Cyr61 that rather results from imperfect background subtraction than from true presence of Cyr61 in the samples. Further, these analyses suggested that the Cyr61 measurement result is close to zero when a large volume of plasma of healthy individuals is analyzed.

The detection limit of the Cyr61 ELISA was determined using plasma samples of healthy female individuals over the age of 50 years. Since for the analysis of breast cancer patients 2.5 µl of plasma were applied, the experiments shown in FIG. 25 were also performed using 2.5 µl of plasma. In this experiment, recombinant Cyr61 was spiked into plasma samples of healthy individuals and the detected OD value was compared with OD values of plasma without spiked Cyr61. These analyses showed that the probability of a correct discrimination of Cyr61 positive samples from negative samples decreased with decreasing amount of Cyr61. The lowest amount of Cyr61 that could be significantly (p=0.05; Student's t-test) discriminated from a negative sample was 1.3 pg Cyr61 (p=0.022), whereas 0.6 pg Cyr61 could not be significantly identified (p=0.299).

Figure 25:
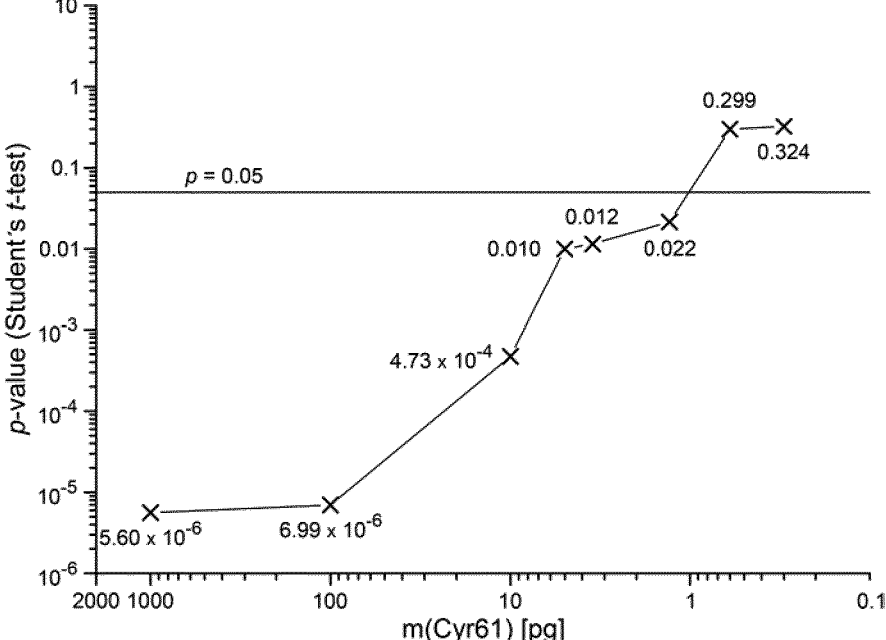

The application of 1.3 pg Cyr61 in 2.5 µl of plasma is a Cyr61 concentration of 520 pg/ml. In the case of 1.3 pg Cyr61, the calculated Cyr61 concentration was 1.707 ng/ml. For a plasma volume of 2.5 µl a false positive value of 1.109 ng/ml was determined (FIG. 25). Subtraction of this false positive value from the detected value yields the Cyr61 concentration present in the sample: 1.707 ng/ml–1.109 ng/ml=0.598 ng/ml. This is a deviation of 78 pg/ml or a mass 0.195 pg Cyr61 at the detection limit of 1.3 pg.

Cyr61 Stability in Plasma Samples

Figure 26:
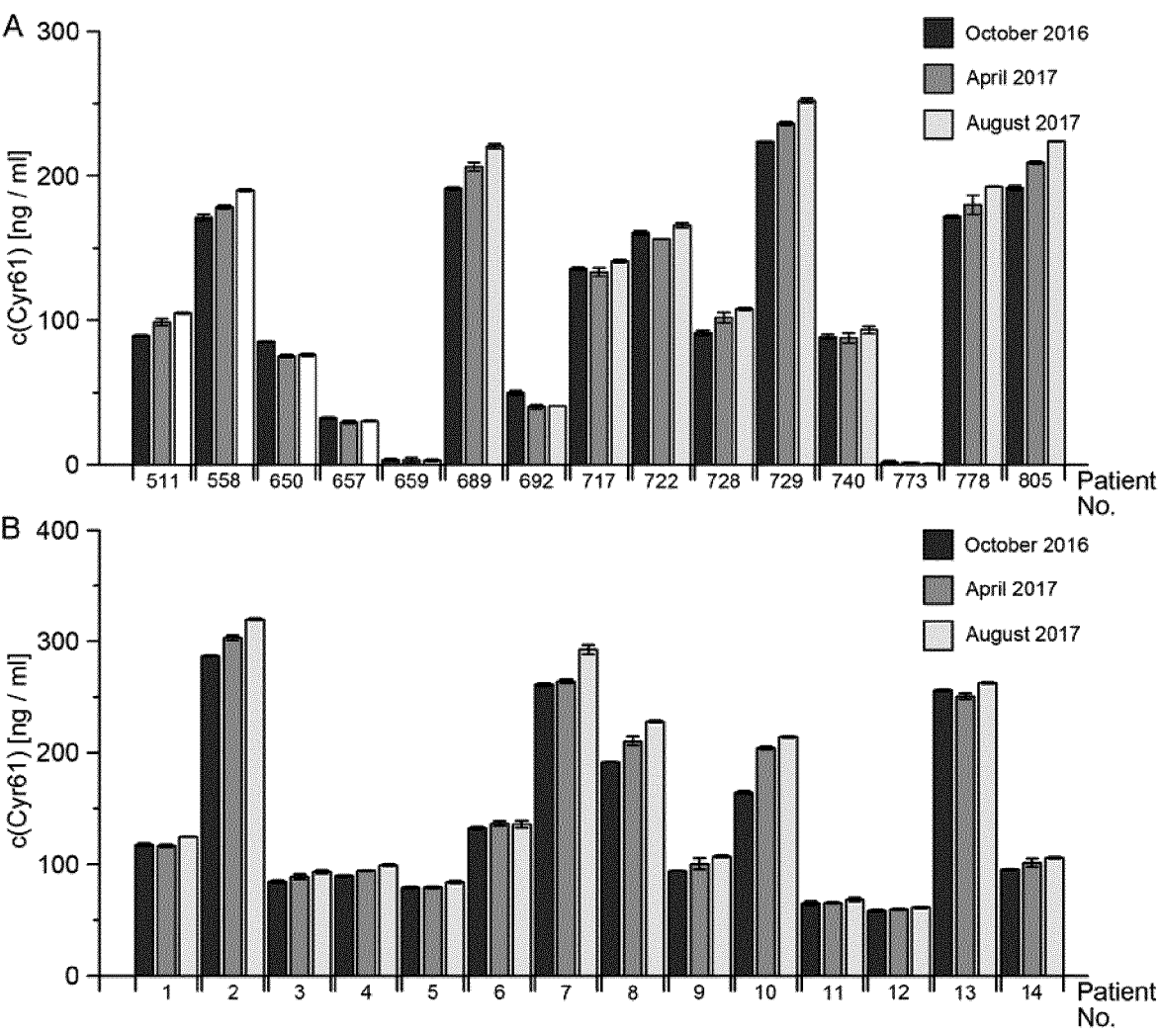

The stability of Cyr61 was analyzed in plasma samples of breast cancer patients. In addition, theses measurements provided first insights into the Cyr61 concentration in the plasma of breast cancer patients (FIG. 26). The first sample set comprised plasma samples of breast cancer patients with no visible signs of overt metastases (stage M0) which were acquired in the years 1998 and 1999 (FIG. 26A). We could not evaluate potential changes in the Cyr61 concentration from the time of sample acquisition to our first measurements. To identify such potential changes, a second sample set was analyzed. The second set consisted of fresh plasma samples from metastatic breast cancer patients at the time of diagnosis (M1, FIG. 26B) that were analyzed immediately after procurement of the blood samples in October 2016. All samples were stored at –80° C. and were thawed for the analysis of the Cyr61 concentration by application of 2.5 µl of plasma.

The first measurement for Cyr61 was performed in October 2016 and provided Cyr61 concentrations in the M0 breast cancer patients (n=15) from 1.5 to 223.6 ng/ml with an average value of 112.5±71.5 ng/ml. In case of the M1 breast cancer patients (n=14) the Cyr61 concentrations ranged from 58.3 ng/ml to 286.9 ng/ml with an average value of 141.1±78.1 ng/ml.

The Cyr61 concentration in freshly acquired plasma samples was determined at the time of acquisition (October 2016), in April 2017 and August 2017 (FIG. 26B). Overall, the Cyr61 concentration remained remarkably constant over time and was similar to the initial Cyr61 concentration (October 2016) in the subsequent measurements. The initial Cyr61 concentration in the samples that were acquired 1998 and 1999 (FIG. 26A) was unknown. Indeed, the Cyr61 concentrations determined in October 2016, April 2017 and August 2017 were similar in each sample for each time point. For the majority of the samples a slight increase of the Cyr61 concentrations was observed in the repeated measurements, which may be due to gradual advances in the handling of the ELISA over time.

These analyses suggested that Cyr61 is very stable in plasma samples at least for the first 10 months after procurement and Cyr61 levels are not affected by freeze-thaw cycles. The samples that were acquired in 1998 and 1999 showed a similar degree of stability like the freshly analyzed samples. Hence, due to the stability of Cyr61, it is conceivable that plasma samples might correctly reflect the Cyr61 concentration at the time of sample acquisition.

CONCLUSIONS

The established Cyr61 ELISA is suitable for the detection of Cyr61 from cell line samples (whole cell lysate and culture supernatants) as well from patient samples. The critical components of an ELISA—the two primary antibodies H2 and H78—showed specific binding to Cyr61 in these samples using recombinant human Cyr61 protein as a control. Notably, both antibodies provided similar quantitative results in Western Blots compared with the ELISA showing that we have established a very homogeneous and robust system that can be used in different applications.

Details about other commercial ELISAs are normally business secrecy, whereas the primary antibodies are described in our assay. The combination of a mouse monoclonal anti-Cyr61 antibody with a rabbit anti-Cyr61 antibody confers the assay the required specificity. In addition, the recognition sites of the two antibodies to Cyr61 are clearly separated, (aa 163-240 for H78 and aa 345-381 for H2) which allows the specific detection of Cyr61 with high sensitivity and with minimized steric hinderance.

For the ELISA, we applied the H2 antibody as the catching antibody that binds to the Cyr61 present in the sample. Using immunoprecipitation we could show that the H2 is able to catch approximately 100% of the Cyr61 in present in the sample.

Our ELISA shows a linear dynamic range over several orders of magnitude, e.g. from 1 to 1000 pg Cyr61, which allows the reliable quantification of Cyr61 from very dilute and concentrated samples in one single experiment. The detection limit of the ELISA is lower than 1.3 pg of Cyr61 in plasma samples. To our experience, this sensitivity is by far sufficient to analyze plasma samples from a variety of different cancers like breast, prostate, lung or liver cancer.

One interesting attribute, which is rarely addressed in other ELISAs, is the effect of false positive values that may originate from imperfect background subtraction in patient samples (see FIG. 24). We have addressed this effect for plasma samples and provide an equation that takes this effect into account. These investigations reduce the number of false positive results.

Further, we have analyzed the ELISA for compatibility with different substances potentially in the sample, like protease inhibitor cocktails, urea, sodium chloride, SDS and others (results not shown) which allowed us to design and assess the ELISA according to specific requirements of the sample.

Since our ELISA is designed from the described components, it is possible to prepare the exact amounts of required wells for one individual experiment, which increases the cost efficiency of the experiments. Moreover, it is possible to store the ELISA wells at –20° C. before or after incubation of the sample without loss of signal intensity, which increases the flexibility in the experimental design and further supports the design of larger experimental set-ups.

EXAMPLE 10 ANALYSES OF THE CYR61 LEVELS IN BLOOD PLASMA OF BREAST CANCER PATIENTS BY THE CYR61 ELISA

Since the proteome of blood samples differs from those of cancer cell lines, we investigated if the established Cyr61-ELISA can be applied to the analysis of blood samples. For the detection of soluble Cyr61 in the blood, the blood plasma was analyzed.

First, the Cyr61 status in the plasma of healthy control individuals was tested by Western Blot (FIG. 12C). Similar to the analyses on cell lines, this may provide information of unspecific binding of the anti-Cyr61 antibody. Since the application of 100 µl of blood plasma resulted in massive distortion of the SDS-gel bands, we applied a protein purification step for the samples analyzed here. To confirm that Cyr61 is recovered in this purification step, 100 ng of recombinant Cyr61 was spiked to one aliquot of the patient samples.

Only in the sample of donor #3 weak unspecific signals with a mass of approx. 40 kDa were detected. The other sections of the X-ray film did not show unspecific signals, suggesting that blood plasma of healthy persons shows only very low levels of soluble Cyr61 and that the anti-Cyr61 antibody specifically detects Cyr61 in the blood serum.

Figure 27:
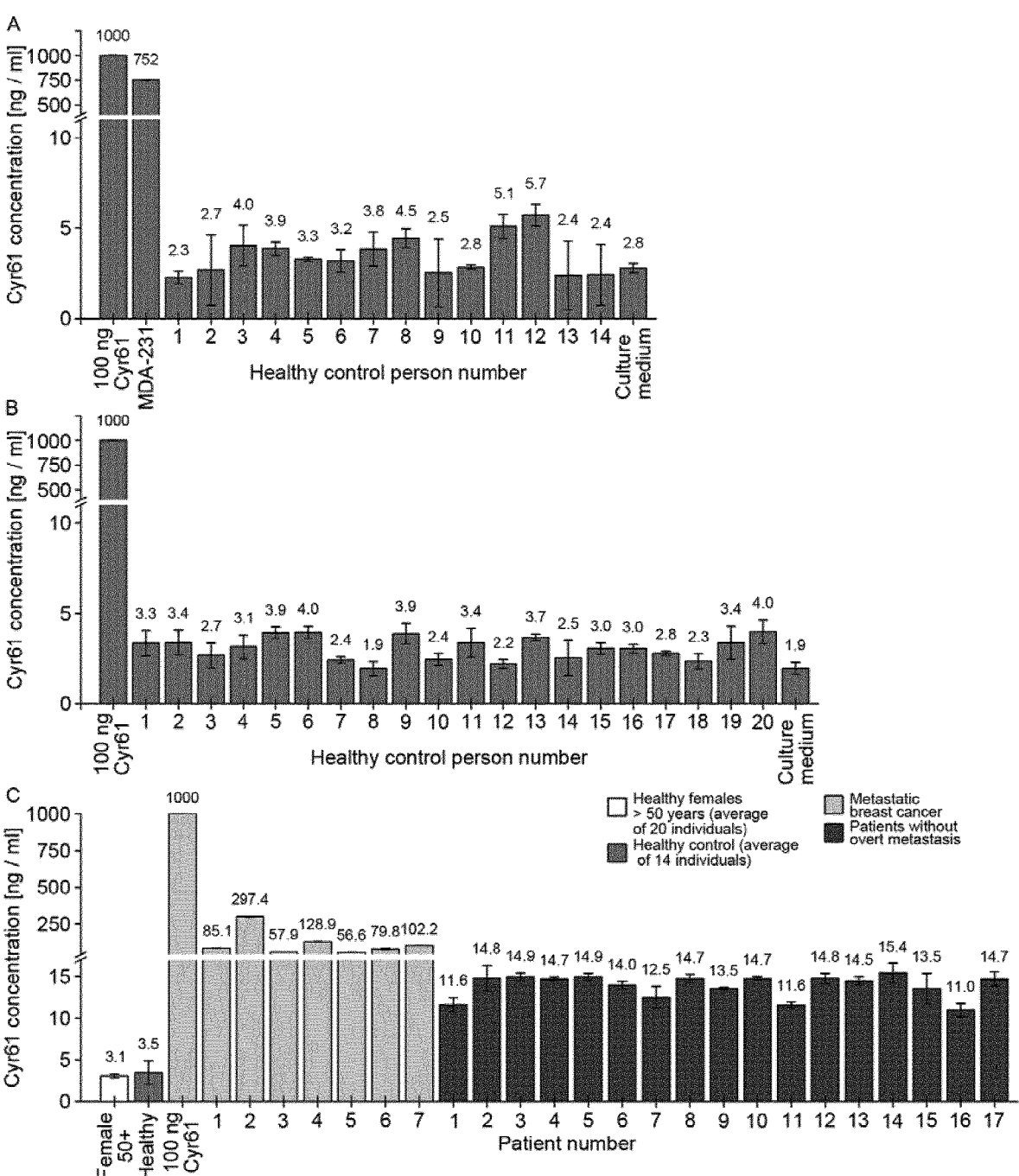

After confirmation of the specificity of the anti-Cyr61 antibody by Western Blot, the Cyr61-ELISA was applied as previously described to blood plasma samples (FIG. 27). For all assays made on human material, 100 µl of plasma were analyzed in triplicates and the values were calculated to the Cyr61 concentration [ng/ml]. The patient samples were analyzed without protein purification step. First, the plasma from 14 arbitrarily chosen (irrespective of sex, age . . . ; FIG. 27A) healthy individuals was analyzed. As reference value 100 ng of recombinant Cyr61 was analyzed.

Since the mayor protein present in blood plasma is albumin, we additionally analyzed cell culture medium containing 10% of purified fetal calf serum, which contains bovine albumin as major protein component. Hence, the obtained value of $2.78 \pm 0.26$ ng/ml for the cell culture medium might be regarded as an unspecific background value.

The calculated Cyr61 concentrations in the samples from the healthy control persons ranged from $2.27 \pm 0.35$ ng/ml to $5.71 \pm 0.60$ ng/ml. The average value of all 14 samples was $3.47 \pm 1.40$ ng/ml. Since breast cancer frequently occurs in women with an age over 50 years, we analyzed blood samples from 20 healthy women that were over 50 years of age at the time of blood sample acquisition (FIG. 27B). In this group, the Cyr61 concentrations in the plasma ranged from $1.93 \pm 0.39$ ng/ml to $3.98 \pm 0.66$ ng/ml. The average value of all 20 samples was $3.07 \pm 0.26$ ng/ml.

In analogous fashion, the Cyr61 values in plasma samples from metastatic breast cancer patients and from breast cancer patients without overt metastasis at the time of the diagnosis of the primary tumour (M0) were analyzed (FIG. 27C). The average Cyr61 value of the samples from the metastatic breast cancer patients (n=7) was $115.4 \pm 84.1$ ng/ml. The values ranged from $56.6 \pm 1.1$ ng/ml to $297.4 \pm 2.5$ ng in the individual patients. For the nonmetastatic (stage M0) cancer patients (n=17) an average value for Cyr61 of $13.9 \pm 0.49$ ng/ml was detected, and the values ranged from $11.0 \pm 0.8$ ng/ml to $15.4 \pm 1.2$ ng/ml in the individual patients.

The Cyr61 levels between the all analyzed healthy persons (n=35) and all analyzed cancer patients ($M_0$ and $M_1$; n=22) differed statistically significant ($p=1.36 \times 10^{-5}$). For the comparison of the non-metastatic ($M_0$; n=17) and meta-static patients ($M_1$; n=7) a statistically significant value of $p=3.70 \times 10^{-5}$ was obtained.

These analyses showed that blood plasma of breast cancer patients exhibited elevated Cyr61 values compared with the healthy controls and the Cyr61 values increased in the course of the metastatic progression.

The Cyr61 ELISA can be applied to the analysis of plasma samples from cancer patients. Plasma samples of healthy control persons—in particular female individuals with an age over 50 years—showed very low Cyr61 values. These values are comparable to the values of cell culture medium without tumour cells, which was analyzed as an unspecific control. Nevertheless, we have not performed a background subtraction for the analyses on plasma samples so that the actual values for human samples might be slightly lower than calculated.

Figure 28:
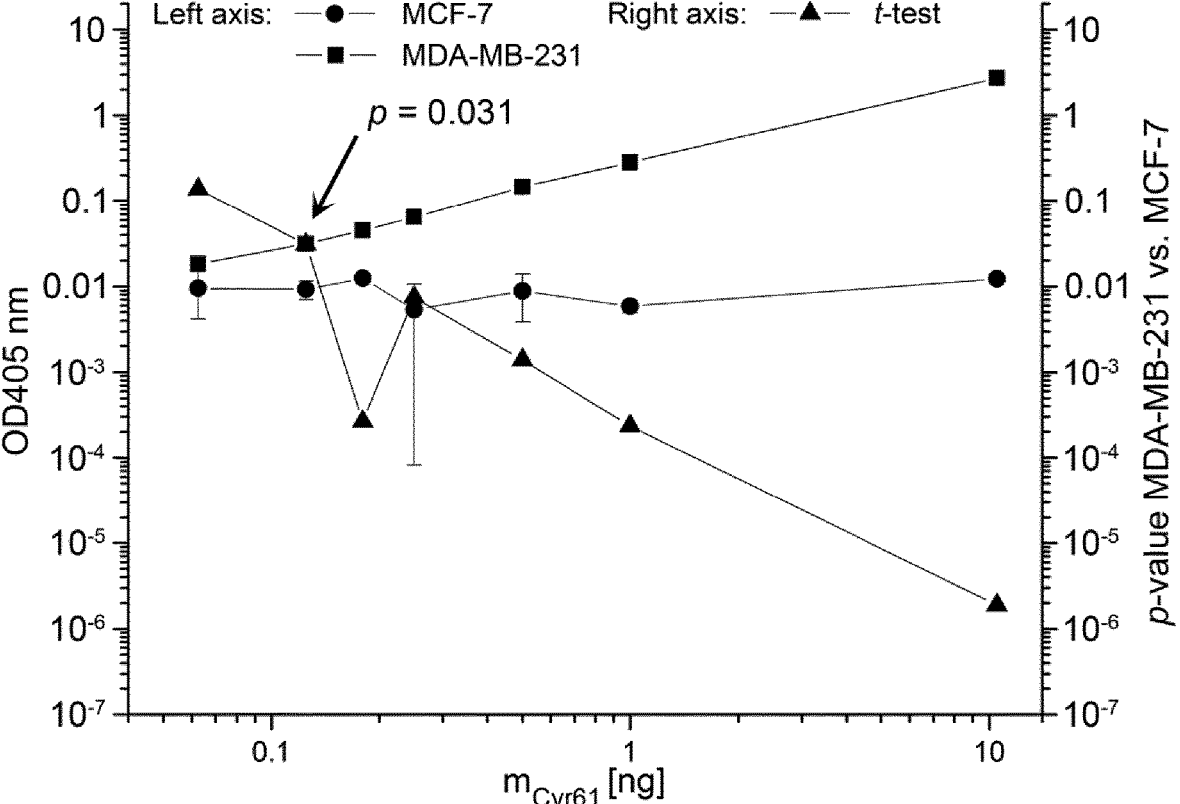

We recently modified the Cyr61 ELISA to a sandwich ELISA. The optimized protocol is described in the method section. An example of this assay obtained on the cell culture supernatants from MDA-MB-231 (positive control) and MCF-7 (negative control) is shown in FIG. 28. This assay allowed the detection of Cyr61 in the supernatant of MDA-MB-231 to a Cyr61 amount of 0.125 ng with statistical significance (p=0.031, Student's t-test). For these experiments, cell culture supernatant from MDA-MB-231 with a Cyr61 concentration of 1050 µg/ml was applied. The concentration was determined using recombinant Cyr61 as a standard. The cell culture supernatants of MDA-MB-231 and MCF-7 were applied in a dilution series. In case of the values obtained from MDA-MB-231 a calibration curve was derived. This calibration curve was applied to a sample of cell culture medium in which 0.5 ng of recombinant Cyr61 was spiked. Application of the calibration curve to the extinction of this sample provided a value of 0.48 ng Cyr61.

As a first application of this Cyr61 assay we compared samples of five breast cancer patients from the time of diagnosis and no signs of overt metastasis with five samples of healthy individuals. For the beast cancer patients we detected an average value of 10.3 ng/ml±9.2 ng/ml and for the healthy individuals a value of 1.0 ng/ml±0.4 ng/ml was observed.

For the detection of Cyr61 by ELISA, the mayor components are the anti-Cyr61 antibody (H78) rabbit polyclonal (Santa Cruz Biotechnology, Santa Cruz, USA), the anti-Cyr61 antibody, mouse monoclonal (clone 365108) from R & D Systems (Minneapolis, USA) and an ELISA reader (e.g. NanoQuant infinite M200 pro, Tecan, Mannedorf, Switzerland at wavelengths suitable for the individual substrate applied). Positive controls are cell culture supernatants from MDA-MB-231 or Hs578t or commercially available recombinant human Cyr61 (Abnova, Taipei, Taiwan). The values for the supernatants from these cell lines should range between 0.9-1.4 µl/ml. The cell culture supernatants should be kept at least for 48 h on the cells. Negative controls may be cell culture supernatants from MCF-7 or GI101 or fresh cell culture medium. An appropriate approach for the analysis of human plasma sample is the generation of a dilution series using recombinant Cyr61 that is spiked into blood plasma of healthy control persons which is compared with blood plasma alone. The Cyr61 concentrations in blood plasma usually range from 1 ng/ml (healthy persons), 10 ng/ml (breast cancer without metastasis) to 100 ng/ml (metastatic breast cancer).

Figure 33:
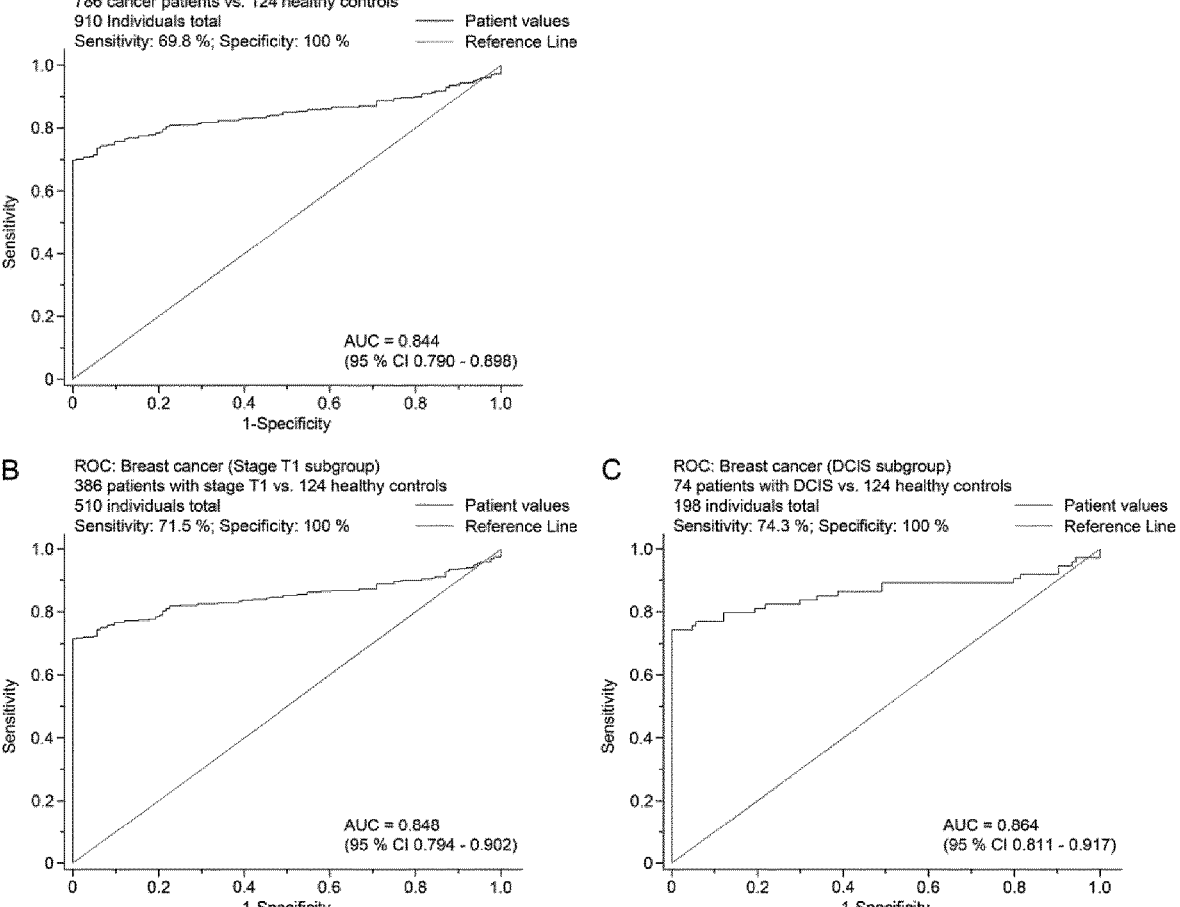

Next we investigated the Cyr61 concentration in plasma samples of breast cancer patients using the ELISA comprising the anti-Cyr61 antibodies H2 and H78 for Cyr61 detection (FIG. 24, FIG. 25). For the detection of soluble Cyr61 in the blood, the blood plasma was analyzed. Since breast cancer frequently occurs in women with an age over 50 years, we analyzed blood samples from healthy women that were over 50 years of age at the time of blood sample acquisition. We analyzed 2.5 µl of blood plasma from 786 breast cancer patients and 124 healthy women with an age over 50 years using our enzyme-linked immunosorbent assay (ELISA) specifically developed for detection of Cyr61 protein. Healthy women showed a Cyr61 concentration of 0.588±0.187 ng/ml, while breast cancer patients (n=786) had elevated Cyr61 concentrations of 25.6±41.3 ng/ml. Remarkably, patients with ductal carcinoma in situ (DCIS, n=74) or stage T1 breast cancer (n=386) showed already elevated Cyr61 levels (31.8±45.8 ng/ml and 29.0±44.3 ng/ml, respectively). Due to this distinct Cyr61 pattern between healthy controls and breast cancer patients, we subsequently determined the sensitivity and specificity of Cyr61 for the detection of breast cancer using ROC analysis (FIG. 33). For all breast cancer patients, we determined a sensitivity of 69.8% and a specificity of 100%. For patients with early stage (T1) invasive breast cancer, the sensitivity was 71.5% and the specificity was also 100%. Remarkably, our assay was also able to detect even ductal carcinoma (DCIS) in situ lesion of the breast with similar precision (sensitivity, 74.3%; specificity, 100%). These high specificities were due to the fact that all healthy controls were virtually negative for Cyr61.

EXAMPLE 11—CYR61 EXPRESSION IN SOLID TUMOR TISSUES OF BREAST CANCER PATIENTS

We assessed whether Cyr61 expression in the primary tumor is a determinant of tumor cell dissemination into the bone marrow. We performed immunostaining of 147 primary breast tumors (FIG. 3A, Table 2 in FIG. 4) and correlated the findings to the presence of DTC detected with our standardized assay (3). In total, 35 tumors (24%) displayed strong Cyr61 signals, 29 tumors (20%) displayed moderate signals, and 83 tumors (56%) showed weak or no Cyr61 signals. Interestingly, no significant correlation of the Cyr61 status in the primary tumor with the DTC status was found.

Figure 3:
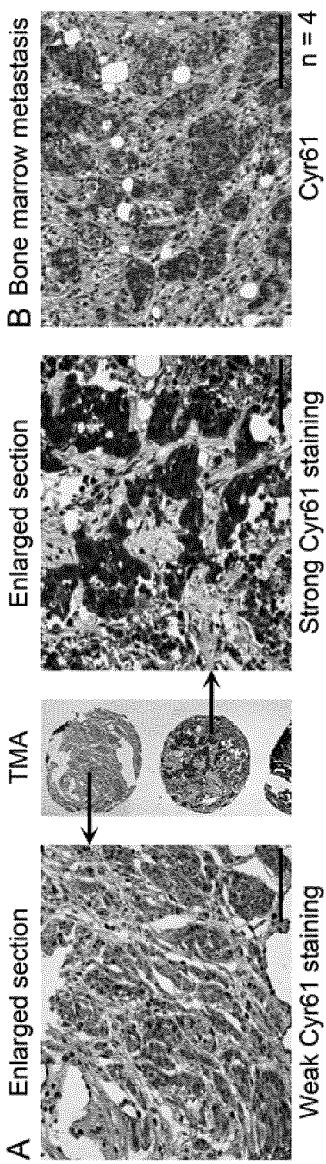
FIG. 3:
A: Cysteine-rich angiogenic inducer 61 (Cyr61) signals by immunohistochemical analysis on samples of a primary breast tumor tissue microarray (TMA). The centre of the image shows a section of the TMA and the enlarged sections left and on the right show representative staining patterns. The number of analyzed cases was 147.

Furthermore, Cyr61 staining was observed on bone metastases of breast cancer patients (FIG. 3B; n=4). The tumor cells were uniformly positive for Cyr61, whereas the surrounding normal tissue showed very weak staining or no signals at all. Unfortunately, the matched primary tumors from the same patients were not available.

EXAMPLE 12—CYR61 EXPRESSION IN CTC/DTC FROM CLINICAL SAMPLES

Subsequently, we analyzed Cyr61 expression in DTC and CTC freshly obtained from cancer patients. To assess the potential of Cyr61 as marker for tumor cells in bone marrow and blood, Cyr61 levels of breast cancer cells were compared with those of mononuclear blood or bone marrow cells from healthy volunteers (FIG. 29). In a first experiment we analyzed mononuclear blood cells by western blot (FIG. 29A) and found that these cells are negative for Cyr61. Next, cell lines were spiked as an internal positive control to mononuclear blood (MDA-231 or BC-M1) or bone marrow cells (MDA-231) from healthy volunteers. The Cyr61 signals in MDA-231 and BC-M1 were clearly distinct from the blood or bone marrow cells (FIG. 29B). Technical evaluation of the method on a small set of three bone marrow samples of DTC positive breast cancer patients revealed that few DTC show Cyr61 signals, whereas the majority of the DTC show very weak or no detectable Cyr61 signals (FIG. 29C).

Figure 30:
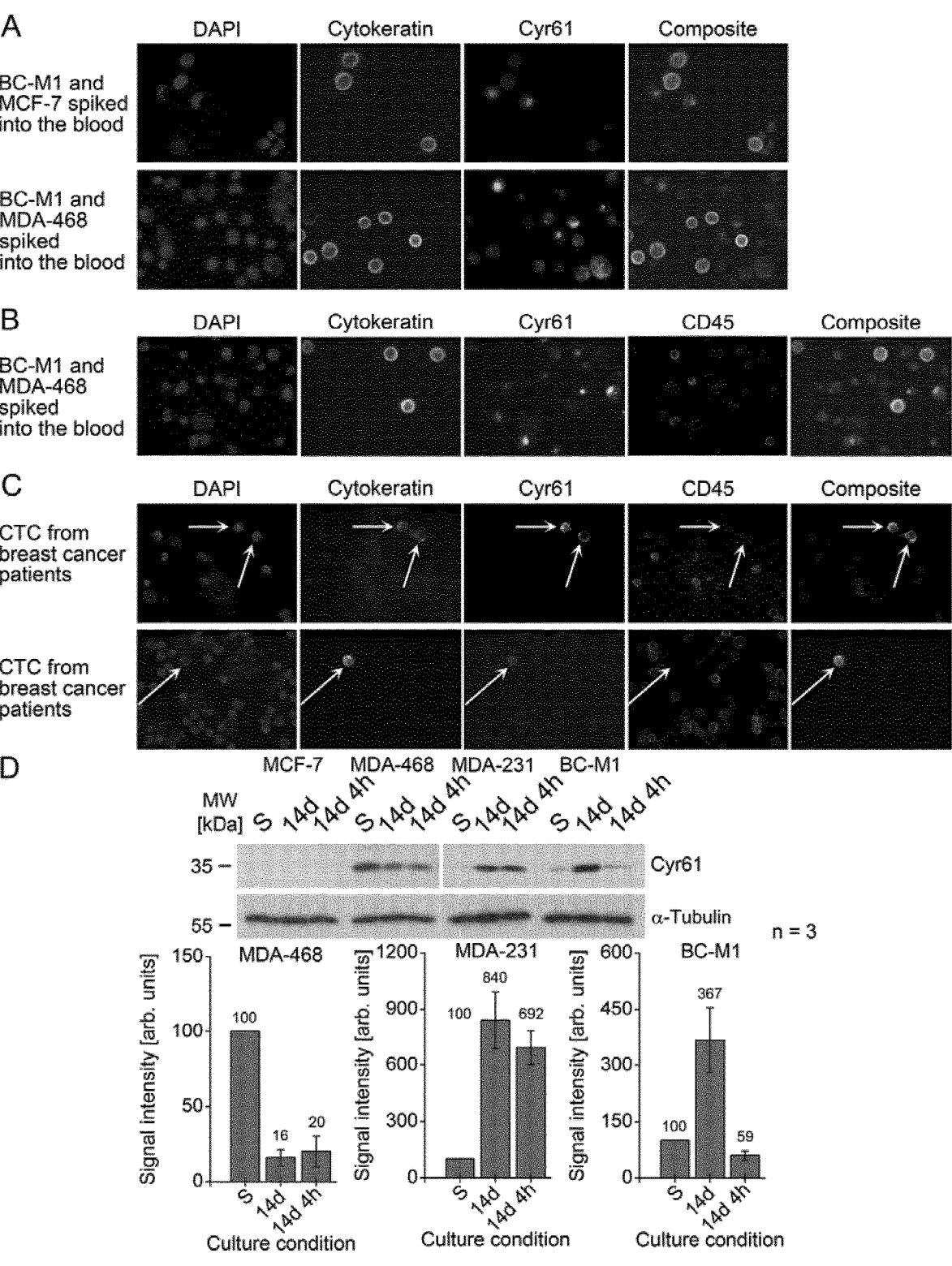
Figure 31:
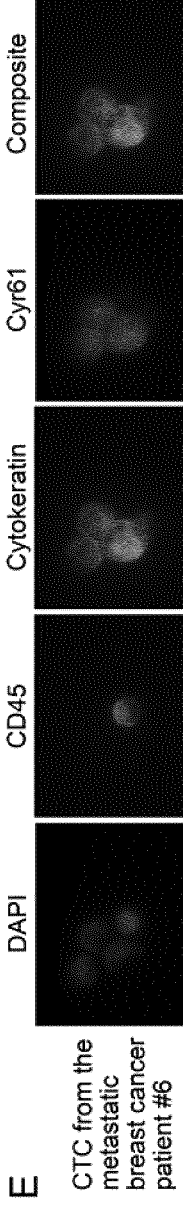

Sensitive Cyr61 detection was obtained by a novel label-free technique that enriches CTCs by their size and allows a reliable subsequent microscopic detection of even low Cyr61 signal intensities (FIG. 30). Tumor cells were detected by cytokeratin staining (FIG. 30A) and additional counterstaining of leukocytes with CD45 antibodies ensured assay specificity, even in the case when cytokeratin expression was weak (FIG. 30B) which is important to detect CTCs undergoing an EMT.

This assay was then applied to peripheral blood samples from 33 breast cancer patients. In total, CTC were detected in 8 cases and Cyr61-positive CTCs were found in three patients. From the 69 CTC of the three patients 17 cells (25%) were Cyr61-positive. Details of the Cyr61 analyses in CTC are provided in Table 3 of FIG. 32.

CTC with strong Cyr61 signals commonly showed a fragmented cytokeratin staining pattern with only distinct cytokeratin-positive cytoplasmic foci and diminished signal intensity (FIG. 30C upper panel). In contrast, Cyr61 weakly positive or Cyr61 negative CTC commonly showed a filamentous cytokeratin pattern with high signal intensity that spans through the entire cytoplasm (FIG. 30C lower panel).

To get closer insights into the dynamics of Cyr61 expression in DTC and CTC, we simulated the dissemination of tumor cells from hypoxic microenvironments into the blood stream. The half-life of CTC in the blood is approximately 1-2.4 h and after 4 h approximately one third of the CTCs is still detectable in the blood (35). The oxygen concentrations in larger blood vessels are around 10% of $O_2$. We therefore cultured cell lines under hypoxic (1% $O_2$) conditions for 14 days to simulate tumor hypoxia, followed by subjection of these cells to 10% $O_2$ for 4 h (FIG. 30D). The question was if CTC from hypoxic microenvironments reach secondary sites faster than the Cyr61 levels in CTC respond to the increased oxygen concentration in the blood.

The Cyr61 levels massively altered under persistent hypoxia compared with the standard culture conditions, in which MDA-231 and BC-M1 strongly induced Cyr61 and MDA-468 downregulated Cyr61. Under the reoxygenation conditions (1% $O_2$ for 14 days+4 h 10% $O_2$ vs. 14 days 1% $O_2$) MDA-468 and MDA-231 kept the Cyr61 levels nearly constant, suggesting that corresponding CTC phenotypes would reach secondary sites only with minor alterations in the Cyr61 levels. In contrast, BC-M1 down regulates Cyr61 in response to reoxygenation to 16% (1% $O_2$ for 14 days+4 h 10% $O_2$ vs. 14 days 1% $O_2$) suggesting that cells with a BC-M1 phenotype may be able to reach distant sites with other Cyr61 phenotypes than those they started their passage with.

The high diagnostic value of Cyr61 detection in patient samples is shown for a patient with metastatic breast cancer (patient 6). The analysis of soluble Cyr61 in the blood (FIG. 27C) and simultaneous analysis of Cyr61 in CTCs (FIG. 17) was carried out and showed that this patient had a high Cyr61 level of 79.8±4.5 ng/ml and Cyr61-positive CTCs in the blood.

EXAMPLE 13—DISCUSSION

Here we identified Cyr61 as a relevant protein that sensitively responds to microenvironmental stress conditions such as hypoxia and glucose starvation in disseminating cancer cells. By analysing clinical samples from breast cancer patients we documented the presence of Cyr61 in the blood plasma, in primary tumour cells, CTC, DTC and overt bone metastases.

In recent years the "liquid biopsy" analysis of circulating tumour cells or material (DNA, proteins or exosomes) released by tumor cells in the peripheral blood of cancer patients has made remarkable progress (37). In a recent study of Cohen et al. further remarkable progress by development of a new blood test that combines mutation analysis of circulating DNA with the determination of tumor-associated proteins in serum was reported (38). However, the detection rate of early stages of cancer—which represents the hallmark of cancer screening—remains a challenge. In total, only 43% of stage I tumors were positive. The rate was even lower in breast cancer samples, where the sensitivity over all stages reached only 33% (38). This is an significant challenge because it is known that early detection of cancer can reduce cancer related mortality (39).

In contrast, we found that Cyr61 concentrations in the blood plasma are already elevated in early stages of breast cancer compared with sex and age matched healthy control individuals. Our ELISA assay also shows superior performance compared to mammography as the current standard tool for breast cancer screening. For the DCIS subgroup, sensitivities of 58%-81% and specificities of 72%-79% using mammography were recently reported (40). Hence, analysis of only 2.5 µl of blood plasma is sufficient for our Cyr61 ELISA to discriminate between a "healthy" status and an early stage of breast cancer. The Cyr61 ELISA assay is a simple and inexpensive alternative to established liquid biopsy assays. In the future, the assay may be a useful tool which could complement and guide the use of mammography in women in breast cancer screening programs.

Cyr61 is a 42 kDa cytoplasmic protein that can be secreted to the extracellular space and increased Cyr61 levels can be already observed in early breast cancer without any signs of distant overt metastases. We could show that the detection of secreted Cyr61 in blood plasma is of potential diagnostic use for early detection and risk assessment of breast cancer (see below).

In cancer, Cyr61 is involved in differentiation, migration and in the induction of angiogenesis or control of cell proliferation. In breast cancer, elevated Cyr61 expression was reported to be associated with high invasiveness in cell lines and with formation of metastasis after injection of these cell lines in mice.

Indeed, proteins may be regulated under microenvironmental stress like hypoxia, which also affects the induction of mesenchymal attributes and tumor cell dissemination and metastasis. We therefore subjected the cell lines to 1% of $O_2$, which is the lower limit of the oxygen concentration in the bone marrow. In addition, 1% of $O_2$ sufficient to stabilize HIF-1α in most human cells. With the exception of BC-M1 and Hs578t all analyzed cell lines downregulated Cyr61 under these conditions. In BC-M1 and Hs578t, Cyr61 down-regulation was only observed upon strong stabilization of HIF-1α by $Co^{2+}$-treatment. This suggests that 1% of $O_2$ in not sufficient to induce a robust stabilization of HIF-1α and subsequent downregulation of Cyr61 in these cells. Hence, DTC with a phenotype of Hs578t and BC-M1 are able to maintain Cyr61 levels in the bone marrow microenvironment and are detectable by Cyr61 expression. This finding is of particular interest, since Hs578t and BC-M1 show a mesenchymal phenotype that is only weakly positive for epithelial marker proteins (12).

Moreover, we noticed a frequent coexpression of Cyr61 and PD-L1 in cell lines from tumour entities that disseminate either by haematogenous or by lymphatic spread. We have not yet investigated a functional relation of PD-L1 with Cyr61. Nevertheless, the coexpression of Cyr61 and PD-L1 suggests that Cyr61 positive cells are well protected from elimination by the immune cells. Hence, detection of strong Cyr61 expression in CTC or DTC from breast, prostate, lung as well as head and neck cancer patients might be an indication for cytoprotection from immune cell targeting. The elevated levels of Cyr61 and PD-L1 in a brain metastatic cell line of MDA-231 suggests that Cyr61 might not solely be implicated into the metastasis to the bone, but also to other distant sites, in particular the brain. Brain metastasis is of special interest in the therapy of breast cancer metastasis, since therapeutic antibodies like Herceptin are unable to pass the blood-brain barrier.

We know from our own experimental experience that Cyr61 detection by antibodies (Western Blot and immunocytochemistry) is by far more sensitive and robust than PD-L1 detection by antibodies. Hence, Cyr61 detection in CTC and DTC might also be a suitable surrogate marker for the capacity of CTC and DTC to escape from immune cell destruction.

All analyzed pancreatic cancer cell lines were positive for Cyr61, suggesting frequent expression of Cyr61 in pancreatic cancer. In particular, we found high Cyr61 levels in the pancreatic cancer cell line with mesenchymal attributes Panc1 and low Cyr61 levels in BxPC3 (epithelial phenotype). Unlike tumour entities like breast and prostate cancer, the metastatic spread frequently occurs via peritoneal dissemination in pancreatic cancer. In pancreatic cancer EMT and dissemination can be already occur at the inflammatory stage of pancreatitis, thus in a pre-malignant stage of pancreatic cancer. Hence, it is possible that Cyr61 is up-regulated during EMT at the stage of pancreatitis and that Cyr61 is suitable to detect pancreatic diseases already at the inflammatory stage.

To validate our in vitro studies, Cyr61 protein levels in clinical specimens were assessed by immunohistochemistry. Scoring staining intensity revealed that 24% of primary breast tumours exhibited a strong Cyr61 expression, which is similar to previous observations by other groups. Cyr61 expression was not correlated to the detection of DTC in bone marrow, which can be explained by the versatile regulation of Cyr61 depending on the actual microenvironmental conditions.

We subsequently focused on the expression of Cyr61 in disseminating cancer cells of breast cancer patients. To detect Cyr61 in CTC, sensitive multiplex immunostaining assays were developed, which allowed us to detect even tumor cells with low Cyr61 levels. We observed a marked heterogeneity of Cyr61 levels in CTCs both with regard to inter and intra-patient variability. This finding might reflect the fact that CTC are derived from various sites and may have encounter various microenvironmental conditions affecting Cyr61 expression. For cytokeratin detection in CTC/DTC, we applied here a sensitive and broad range pan-cytokeratin antibody cocktail. This cocktail is suitable to detect cytokeratin in the DTC cell lines with downregulated expression of cytokeratins typical for adenocarcinomas (12, 29). Interestingly, no Cyr61 positive/cytokeratin negative cells were found, supporting a previous finding that breast cancer cells with a complete lack of all cytokeratin proteins are very rare (32). It furthermore underlines the absence of Cyr61 in hematopoietic cells and points to the potential usefulness of Cyr61 as marker for CTC/DTC.

Our findings support the view that disseminating tumor cells can undergo a fluent transition from epithelial to mesenchymal characteristics but a complete conversion to a totally mesenchymal phenotype of adenocarcinoma cells might occur infrequently (if at all) in situ.

Taken together, the present findings support the view that Cyr61 expression in breast cancer cells might underlie diverse regulatory influences during the passage from the primary to the metastatic site, and cytoplasmic Cyr61 in the primary tumour is therefore no good indicator of the adaptive changes required for survival and metastatic outgrowth.

We observed that normal blood and bone marrow cells exhibit extremely low Cyr61 levels, which may allow us to further develop Cyr61 as detection marker for CTCs and DTC with mesenchymal attributes. These cells are frequently missed by current assays based on epithelial antigens, which may explain false-negative findings. Therefore, new markers for mCTC and mDTC are urgently needed. Cyr61 detection in tumour cells with mesenchymal attributes might support the identification of mCTC/mDTC.

Most importantly for future diagnostic use, the blood plasma of age-matched healthy persons displayed very low levels of secreted Cyr61 detected with the Cyr61 ELISA as compared to significantly higher values in breast cancer patients. This important finding suggests that elevated Cyr61 levels in the blood plasma are an attribute of breast cancer cells.

On all analyzed cell lines we found that the amount of secreted Cyr61 is proportional to the amount of cytoplasmic Cyr61. Therefore, it is plausible that cell lines of cancer entities that are positive for cytoplasmic Cyr61 like lung, prostate, head and neck or pancreatic cancer also secrete Cyr61. Since the arbitrarily collected healthy donor group displayed very low Cyr61 levels, we expect the detection of elevated Cyr61 levels in the blood plasma of cancer patients of other entities than breast cancer.

All analyzed plasma samples that were obtained from cancer patients at the time of diagnosis were Cyr61 positive, whereas we classified 56% of the primary tumours as Cyr61 weakly positive or negative on the tissue microarray array. One reason for this might be the different detection methods with different sensitivities for Cyr61 (Immunohistochemistry vs. ELISA). While the Cyr61 molecules are spread over the slide surface in case of IHC, the ELISA integrates the signals of all Cyr61 molecules in 100 µl of sample to one single OD value. This ELISA approach may increase the sensitivity leading to more Cyr61 positive measurements, but cannot discriminate between Cyr61 positive and Cyr61 negative single cells.

Moreover, tumour cells may secrete considerable amounts of Cyr61 into the extracellular space; in particular under conditions of persistent fluid exchange elevated amounts of Cyr61 are secreted. In patients, this would resemble to a situation where tumour cells are in proximity to blood vessels. This may lead to a constant withdrawal of Cyr61 and induction of Cyr61 secretion by the tumour cells. Under these conditions, nascent Cyr61 might be immediately secreted so that Cyr61 cannot accumulate within the cells. Hence, the sensitivity of the ELISA together with the Cyr61 secretion under liquid exchange conditions may allow the detection of Cyr61 in the blood plasma even when the tumour cells show low levels of Cyr61 or when tumour cell colonies are relatively small.

Therefore, ELISA-based detection of Cyr61 in blood plasma may be suitable for the early detection of breast cancer, which could help to reduce the number of mammographies in current screening programs of women over the age of 50 years. This would considerably reduce health costs and potential side effects caused by radiation. Moreover, we showed that CYR61 levels increase with tumour progression (i.e., higher values in M1 vs. Mo patients), indicating a potential use as blood-based marker to assess and monitor the risk of progression towards metastasis—the leading cause of cancer-related death—and monitor the efficacy of antimetastatic therapies (36).

REFERENCES

1. Pantel K, Brakenhoff R H. Dissecting the metastatic cascade. Nat Rev Cancer 2004; 4(6): 448-56.
2. Pantel K, Alix-Panabieres C, Riethdorf S. Cancer micrometastases. Nat Rev Clin Oncol 2009; 6(6): 339-51.
3. Janni W, Vogl F D, Wiedswang G, Synnestvedt M, Fehm T, Juckstock J, et al. Persistence of disseminated tumor cells in the bone marrow of breast cancer patients predicts increased risk for relapse—a European pooled analysis. Clin Cancer Res 2011; 17(9): 2967-76.
4. Yu M, Bardia A, Wittner B S, Stott S L, Smas M E, Ting D T, et al. Circulating breast tumor cells exhibit dynamic changes in epithelial and mesenchymal composition. Science 2013; 339(6119):580-4.
5. Alix-Panabieres & Pantel, Challenges in Circulating Tumor Cell Research, Nature Reviews, vol. 14, 2014, 623-631.
6. US 2004/0086504.
7. US 2011/0189700.
8. Sun et al., Involvement of Cyr61 in Growth, Migration and Metastasis of Prostate Cancer Cells, British Journal of Cancer, vol. 99, 2008, 1656-1667.
9. Lin et al., Elevated Expression of Cyr61 Enhances Peritoneal Dissemination of Gastric Cancer Cells Through Integrin α2β1, The Journal of Biological Chemistry, vol. 282, 2007, 34594-34604.
10. Bendas & Borsick, Cancer Cell Adhesion and Metastasis, Selectins, Integrins and the Inhibitory Potential of Heparins, International Journal of Cell Biology, vol. 2012, 1-10.
11. Pantel K, Dickmanns A, Zippelius A, Klein C, Shi J, Hoechtlen-Vollmar W, et al. Establishment of micrometastatic carcinoma cell lines: a novel source of tumor cell vaccines. J Natl Cancer Inst 1995; 87(15):1162-8.
12. Bartkowiak K, Effenberger K E, Harder S, Andreas A, Buck F, Peter-Katalinic J, et al. Discovery of a novel unfolded protein response phenotype of cancer stem/progenitor cells from the bone marrow of breast cancer patients. J Proteome Res 2010; 9(6): 3158-68.
13. Pollari S, Kakonen S M, Edgren H, et al. Enhanced serine production by bone metastatic breast cancer cells stimulates osteoclastogenesis. Breast Cancer Res Treat 2012; 125: 421-430.
14. Peyruchaud O, Winding B, Pecheur I, et al. Early detection of bone metastases in a murine model using fluorescent human breast cancer cells: application to the use of the bisphosphonate zoledronic acid in the treatment of osteolytic lesions. J Bone Miner Res 2001; 16: 2027-2034.
15. Dittmar T, Husemann A, Schewe Y, Nofer J R, Niggemann B, Zanker K S, et al. Induction of cancer cell migration by epidermal growth factor is initiated by specific phosphorylation of tyrosine 1248 of c-erbB-2 receptor via EGFR. FASEB J 2002; 16(13):1823-5.
16. Lehtinen L, Vainio P, Wikman H, Reemts J, Hilvo M, Issa R, et al. 15-Hydroxyprostaglandin dehydrogenase associates with poor prognosis in breast cancer, induces epithelial-mesenchymal transition, and promotes cell migration in cultured breast cancer cells. J Pathol 2012; 226(4):674-86.

17. Bartkowiak K, Wieczorek M, Buck F, Harder S, Moldenhauer J, Effenberger K E, et al. Two-dimensional differential gel electrophoresis of a cell line derived from a breast cancer micrometastasis revealed a stem/progenitor cell protein profile. J Proteome Res 2009; 8(4):2004-14.

18. Neuhoff V, Arold N, Taube D, et al. Improved staining of proteins in polyacrylamide gels including isoelectric focusing gels with clear background at nanogram sensitivity using Coomassie Brilliant Blue G-250 and R-250. *Electrophoresis* 1988; 9: 255-262.

19. Kohlbacher O, Reinert K, Gropl C, et al. TOPP—the OpenMS proteomics pipeline. *Bioinformatics* 2007; 23: e191-197.

20. Sturm M, Bertsch A, Gropl C, et al. OpenMS—an open-source software framework for mass spectrometry. *BMC Bioinformatics* 2008; 9: 163.

21. Geer L Y, Markey S P, Kowalak J A, et al. Open mass spectrometry search algorithm. *J Proteome Res* 2004; 3: 958-964.

22. Fenyo D, Beavis R C. A method for assessing the statistical significance of mass spectrometry-based protein identifications using general scoring schemes. *Anal Chem* 2003; 75: 768-774.

23. Nahnsen S, Bertsch A, Rahnenfuhrer J, et al. Probabilistic consensus scoring improves tandem mass spectrometry peptide identification. *J Proteome Res* 2011; 10: 3332-3343.

24. Yuan Y, Hilliard G, Ferguson T, et al. Cobalt inhibits the interaction between hypoxia-inducible factor-alpha and von Hippel-Lindau protein by direct binding to hypoxia-inducible factor-alpha. *J Biol Chem* 2003; 278: 15911-15916.

25. Mazel M, Jacot W, Pantel K, Bartkowiak K, Topart D, Cayrefourcq L, Rossille D, Maudelonde T, Fest T, Alix-Panabières C. Frequent expression of PD-L1 on circulating breast cancer cells. Mol Oncol. 2015 Jun. 9. doi: 10.1016/j.molonc.2015.05.009. [Epub ahead of print].

26. Barsoum I B, Smallwood C A, Siemens D R, et al. A mechanism of hypoxia-mediated escape from adaptive immunity in cancer cells. Cancer Res 2014; 74: 665-674.

27. Yachida S, Iacobuzio-Donahue C A. The pathology and genetics of metastatic pancreatic cancer. Arch Pathol Lab Med. 2009 March; 133(3):413-22.

28. Rhim A D, Mirek E T, Aiello N M, Maitra A, Bailey J M, McAllister F, Reichert M, Beatty G L, Rustgi A K, Vonderheide R H, Leach S D, Stanger B Z. EMT and dissemination precede pancreatic tumor formation. Cell. 2012 Jan. 20; 148(1-2):349-61.

29. Effenberger K E, Borgen E, Eulenburg C Z, Bartkowiak K, Grosser A, Synnestvedt M, et al. Detection and clinical relevance of early disseminated breast cancer cells depend on their cytokeratin expression pattern. Breast Cancer Res Treat 2011; 125(3):729-38.

30. Dery M A, Jodoin J, Ursini-Siegel J, Aleynikova O, Ferrario C, Hassan S, et al. Endoplasmic reticulum stress induces PRNP prion protein gene expression in breast cancer. Breast Cancer Res 2013; 15(2):R22.

31. Braun S, Vogl F D, Naume B, Janni W, Osborne M P, Coombes R C, et al. A pooled analysis of bone marrow micrometastasis in breast cancer. N Engl J Med 2005; 353(8):793-802.

32. Willipinski-Stapelfeldt B, Riethdorf S, Assmann V, Woelfle U, Rau T, Sauter G, et al. Changes in Cytoskeletal Protein Composition Indicative of an Epithelial-Mesenchymal Transition in Human Micrometastatic and Primary Breast Carcinoma Cells. Clin Cancer Res 2005; 11(22):8006-14.

33. Bartkowiak, K., Kwiatkowski, M., Buck, F., Gorges, T. M., et al., Disseminated Tumor Cells Persist in the Bone Marrow of Breast Cancer Patients through Sustained Activation of the Unfolded Protein Response. Cancer Res 2015, 75, 5367-5377.

34. Vellon, L., Menendez, J. A. and Lupu, R. (2005) AlphaV-beta3 integrin regulates heregulin (HRG)-induced cell proliferation and survival in breast cancer. Oncogene, 24, 3759-3773.

35. Meng, S., Tripathy, D., Frenkel, E. P., Shete, S., Naftalis, E. Z., Huth, J. F., Beitsch, P. D., Leitch, M., Hoover, S., Euhus, D., Haley, B., Morrison, L., Fleming, T. P., Herlyn, D., Terstappen, L. W., Fehm, T., Tucker, T. F., Lane, N., Wang, J. and Uhr, J. W. (2004) Circulating tumor cells in patients with breast cancer dormancy. Clin Cancer Res, 10, 8152-8162.

36. Bidard, F. C., Peeters, D. J., Fehm, T., Nole, F., Gisbert-Criado, R., Mavroudis, D., Grisanti, S., Generali, D., Garcia-Saenz, J. A., Stebbing, J., Caldas, C., Gazzaniga, P., Manso, L., Zamarchi, R., de Lascoiti, A. F., De Mattos-Arruda, L., Ignatiadis, M., Lebofsky, R., van Laere, S. J., Meier-Stiegen, F., Sandri, M. T., Vidal-Martinez, J., Politaki, E., Consoli, F., Bottini, A., Diaz-Rubio, E., Krell, J., Dawson, S. J., Raimondi, C., Rutten, A., Janni, W., Munzone, E., Caranana, V., Agelaki, S., Almici, C., Dirix, L., Solomayer, E. F., Zorzino, L., Johannes, H., Reis-Filho, J. S., Pantel, K., Pierga, J. Y. and Michiels, S. (2014) Clinical validity of circulating tumour cells in patients with metastatic breast cancer: a pooled analysis of individual patient data. *Lancet Oncol,* 15, 406-414

37. Bardelli A and Pantel K. Liquid Biopsies, What We Do Not Know (Yet). Cancer Cell. 2017; 31(2):172-179]

38. J. D. Cohen et al., Science 10.1126/science.aar3247 (2018)]

39. Heidi Ledford. Simple blood test detects eight different kinds of cancer. Nature. 18 Jan. 2018]

40. Aminololama-Shakeri S et al. Can Radiologists Predict the Presence of Ductal Carcinoma In Situ and Invasive Breast Cancer? AJR Am J Roentgenol. 2017; April; 208(4): 933-939]

The invention claimed is:

1. Method of detecting breast cancer or breast cancer cells from a liquid biopsy and treating a subject, said method comprising:

(a) detecting in a liquid sample comprising cells obtained from the subject the presence of circulating tumor cells and/or disseminating tumor cells and the presence of cell surface associated Cyr61 in the liquid sample by ELISA, immunocytochemistry, or mass spectrometry; and (b) administering an effective amount of an anti-cancer drug to the subject, wherein the liquid sample is selected from blood, and/or bone marrow aspirate.

2. The method of claim 1, wherein the ELISA is a sandwich ELISA using two different anti-human Cyr61 antibodies binding to distinct Cyr61 epitopes.

3. The method of claim 2, wherein the distinct Cyr61 epitopes bound by the different anti-human Cyr61 antibodies are at least 50 amino acids apart, or at least 75, 85 or 100 amino acids apart.

4. The method of claim 1, wherein the detection of the presence of cell surface associated Cyr61 comprises detecting the level of Cyr61 in the liquid sample.

5. The method of claim 4, further comprising:
(c) comparing the level of Cyr61 in the liquid sample to the level of Cyr61 in a reference sample.
6. The method of claim 5, wherein the reference sample is:
(i) a sample of healthy women over fifty years of age; or
(ii) an age- and sex-matched reference sample.
7. The method of claim 1, further comprising a differential diagnosis by detecting said circulating tumor cells and/or disseminating tumor cells characterized as expressing cell surface associated Cyr61 and epithelial cytokeratins, and having lack of expression of leukocyte marker CD45 before administering said anticancer drug to said subject.
8. The method of claim 7, wherein the method additionally comprises the detection of HIF-1 alpha and/or PD-L1 as a marker of said circulating tumor cells and/or disseminating tumor cells in the liquid sample.
9. The method of claim 4 for the diagnosis or differential diagnosis of cancer, wherein the diagnosis is a differential diagnosis of the metastatic potential of a breast cancer cell based on said level of Cyr61 in the liquid sample.

10. The method of claim 4 for the diagnosis or differential diagnosis of cancer, wherein the diagnosis is a differential diagnosis of an early cancer inflammatory condition based on said level of Cyr61 in the liquid sample.
11. The method of claim 1, wherein said circulating tumor cells and/or disseminating tumor cells are detected in said sample based on lack of expression of CD45.
12. The method of claim 1, wherein said circulating tumor cells and/or disseminating tumor cells are detected in said sample based on detecting expression of cytokeratins.
13. The method of claim 1, wherein said detecting step (a) comprises contacting the cells or homogenate thereof in the sample with an anti-Cyr61 antibody and with at least one further antibody selected from the group consisting of an anti-cytokeratin antibody and an anti-CD45 antibody.
14. The method of claim 13, wherein the presence of cell associated Cyr61 tumor cells and/or cell associated Cyr61 disseminating tumor cells are detected after said contacting step.

* * * * *